US007935786B2

(12) United States Patent
Larsen

(10) Patent No.: US 7,935,786 B2
(45) Date of Patent: May 3, 2011

(54) PHARMACOLOGICALLY ACTIVE PEPTIDE CONJUGATES HAVING A REDUCED TENDENCY TOWARDS ENZYMATIC HYDROLYSIS

(75) Inventor: Bjarne Due Larsen, Roskilde (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 11/807,159

(22) Filed: May 25, 2007

(65) Prior Publication Data

US 2007/0293418 A1 Dec. 20, 2007

Related U.S. Application Data

(63) Continuation of application No. 11/007,772, filed on Dec. 7, 2004, now Pat. No. 7,414,107, which is a continuation of application No. 09/341,590, filed as application No. pct/dk99/00118 on Jul. 12, 1999, now abandoned.

(30) Foreign Application Priority Data

Mar. 9, 1998 (DK) .......................................... 0317/98
Mar. 9, 1999 (WO) ...................... PCT/DK99/00118

(51) Int. Cl.
C07K 14/00 (2006.01)
(52) U.S. Cl. ........ 530/324; 530/325; 530/326; 530/327; 530/328
(58) Field of Classification Search ........... 530/324–328
See application file for complete search history.

(56) References Cited

U.S. PATENT DOCUMENTS

| 4,018,754 | A | | 4/1977 | Inouye et al. |
| 4,081,434 | A | | 3/1978 | Li |
| 4,096,237 | A | * | 6/1978 | Li ................................. 436/542 |
| 4,288,627 | A | | 9/1981 | Kubicek |
| 4,457,864 | A | | 7/1984 | Hruby et al. |
| 4,485,039 | A | | 11/1984 | Hruby et al. |
| 4,542,124 | A | | 9/1985 | Huffman et al. |
| 4,707,468 | A | | 11/1987 | Yoshino et al. |
| 4,724,229 | A | | 2/1988 | Ali |
| 4,833,125 | A | | 5/1989 | Neer et al. |
| 4,847,240 | A | | 7/1989 | Ryser et al. |
| 5,021,550 | A | | 6/1991 | Zeiger |
| 5,194,586 | A | | 3/1993 | Maeda et al. |
| 5,330,971 | A | | 7/1994 | Wells et al. |
| 5,376,530 | A | * | 12/1994 | De The et al. .................... 435/6 |
| 5,512,473 | A | | 4/1996 | Brent et al. |
| 5,545,719 | A | | 8/1996 | Shashoua |
| 5,625,048 | A | | 4/1997 | Tsien et al. |
| 5,646,120 | A | | 7/1997 | Sumner-Smith et al. |
| 5,652,122 | A | | 7/1997 | Frankel et al. |
| 5,679,641 | A | | 10/1997 | Melief et al. |
| 5,688,760 | A | | 11/1997 | Kemp et al. |
| 5,716,614 | A | | 2/1998 | Katz et al. |
| 5,723,129 | A | | 3/1998 | Potter et al. |
| 5,731,408 | A | | 3/1998 | Hadley et al. |
| 5,831,001 | A | | 11/1998 | Twist et al. |
| 5,968,513 | A | | 10/1999 | Gallo et al. |
| 5,985,829 | A | | 11/1999 | Harris et al. |
| 6,113,896 | A | | 9/2000 | Lazarus et al. |
| 6,126,939 | A | | 10/2000 | Eisenbach-Schwartz et al. |
| 6,962,902 | B2 | * | 11/2005 | Balasubramanium et al. ... 514/9 |
| 7,008,925 | B1 | | 3/2006 | Szardenings |
| 7,176,282 | B1 | | 2/2007 | Holm et al. |
| 7,662,782 | B2 | | 2/2010 | Szardenings et al. |
| 2006/0063699 | A1 | | 3/2006 | Larsen |
| 2007/0004905 | A1 | | 1/2007 | Holm et al. |
| 2007/0027086 | A1 | | 2/2007 | Szardenings et al. |
| 2009/0069242 | A1 | | 3/2009 | Jonassen |

FOREIGN PATENT DOCUMENTS

| EP | 0700995 | 3/1996 |
| WO | WO 91/17243 | 11/1991 |
| WO | WO 91/19735 | 12/1991 |
| WO | WO 95/11988 | 5/1995 |
| WO | WO 95/13085 | 5/1995 |
| WO | WO 96/22067 | 7/1996 |
| WO | WO 97/24445 | 7/1997 |
| WO | WO 98/03192 | 1/1998 |
| WO | WO 98/08871 | 3/1998 |
| WO | WO 98/11126 | 3/1998 |
| WO | WO 98/22577 | 5/1998 |
| WO | WO 98/28427 | 7/1998 |
| WO | WO 98/52614 | 11/1998 |
| WO | WO 99/46283 | 9/1999 |
| WO | WO 99/57148 | 11/1999 |
| WO | WO 01/04156 | 1/2001 |
| WO | WO 01/36980 | 5/2001 |
| WO | WO 01/90140 | 11/2001 |

OTHER PUBLICATIONS

English Abstract of Syskov (Bioorg Khim 10(5), 618-625, 1984).*
Amendment filed Sep. 18, 2009, in U.S. Appl. No. 09/341,590 (filed Jul. 13, 1999).*
Barany et al., "Solid-phase peptide synthesis: a silver anniversary report," *Int. J. Pept. Protein Res.* 30(6):705-739 (1987).
Burger et al., "The combination of lysine polypeptides with tobacco mosaic virus," *J. Biol. Chem.* 193(1):13-22 (1951).
Cameron et al., "Feedback Control in Organic Synthesis. A System for Solid Phase Peptide Synthesis with True Automation," *J. Chem. Soc., Chem. Commun.* 4:270-272 (1987).
Chou et al., "Empirical Predictions of Protein Conformation," *Ann. Rev. Biochem.* 47:251-276 (1978).
Docherty et al., "Inactivation of herpes simplex virus types 1 and 2 by synthetic histidine peptides," *Antimicrob. Agents Chemother.* 31(10):1562-1566 (1987).
Duguay et al., "Mutational analysis of the insulin-like growth factor I prohormone processing site," *J. Biol. Chem.* 270(29):17566-17574 (1995).

(Continued)

*Primary Examiner* — David Lukton
(74) *Attorney, Agent, or Firm* — Kristina Bieker-Brady; Clark & Elbing LLP

(57) ABSTRACT

The invention is directed to a pharmacologically active peptide conjugate having a reduced tendency towards enzymatic cleavage comprising a pharmacologically active peptide sequence (X) and a stabilising peptide sequence (Z) of 4-20 amino acid residues covalently bound to X.

26 Claims, No Drawings

OTHER PUBLICATIONS

Fawell et al., "Tat-mediated delivery of heterologous proteins into cells," *Proc. Natl. Acad. Sci. U.S.A.* 91(2):664-668 (1994).

Greene et al., "Enkephalin analog prodrugs: assessment of in vitro conversion, enzyme cleavage characterization and blood-brain barrier permeability," *J. Pharm. Exp. Ther.* 277(3):1366-1375 (1996).

Howells, "Proenkephalin biosynthesis in the rat," *NIDA Res. Monogr.* 70:43-65 (1986).

Kent, "Chemical Synthesis of Peptides and Proteins," *Ann. Rev. Biochem.* 57:957-989 (1988).

Larsen et al., "Incomplete Fmoc Deprotection in Solid-phase Synthesis of Peptides," *Int. J. Peptide Protein Res.* 43:1-9 (1994).

Larsen et al., "The Merrifield Peptide Synthesis Studied by Near-Infrared Fourier-Transform Raman Spectroscopy,"*J. Am. Chem. Soc.* 115:6247-6253 (1993).

Mascotti et al., "Thermodynamics of single-stranded RNA binding to oligolysines containing tryptophan," *Biochemistry.* 31:8932-8946 (1992).

Meldal et al., "Multiple column peptide synthesis, Part 2 (1,2)," *Int. J. Peptide Protein Res.* 41:250-260 (1993).

Merrifield, "Solid Phase Synthesis," *Science* 232:341-347 (1986).

Noguchi et al., "Dipeptides as inhibitors of the gelation of sickle hemoglobin," *Mol Pharmacol.* 28:40-44 (1985).

Prokai et al., "Peptide delivery into the central nervous system: invasive, physiological and chemical approaches," *Exp. Opin. Ther. Patents* 7(3):233-245 (1997).

Rao et al., "Molecular cloning, sequence analysis and translation of proenkephalin mRNA from rat heart," *Regul. Pept.* 40:397-408 (1992).

Rapp et al., "Prediction and Prevention of Peptide Conformations during Synthesis," *Peptides: Chemistry, Structure and Biology*: 40-43 (1994).

Rosen et al., "Isolation and characterization of the rat proenkephalin gene," *J Biol Chem.* 259:14309-14313 (1984).

Sai et al., "Absorptive-mediated endocytosis of a basic peptide in enterocyte-like Caco-2 cells," *Am. J. Physiol.* 275(3):G514-G520 (1998).

Shimohigashi et al., "Sensitivity of opioid receptor-like receptor ORL1 for chemical modification on nociceptin, a naturally occurring nociceptive peptide," *J Biol Chem.* 271: 23642-23645 (1996).

Steiner et al., "The new enzymology of precursor processing endoproteases," *J. Biol. Chem.* 267(33):23435-23438 (1992).

Tamai et al., "Drug delivery through the blood-brain barrier," *Adv. Drug Delivery Rev.* 19(3):401-424 (1996).

Tamai et al., "Structure-internalization relationship for adsorptive-mediated endocytosis of basic peptides at the blood-brain barrier," *J. Pharmacol. Exp. Ther.* 280(1):410-415 (1997).

Tamiya et al., "Effect of synthetic Lys-Trp on adenosine triphosphatase activity of carp and rabbit myosin Bs," *Comp Biochem Physiol B.* 75:23-25 (1983).

Thomas et al., "Structure-activity relationships of a series of [D-Ala2]deltorphin I and II analogues; in vitro blood-brain barrier permeability and stability,"*J. Pharmacol. Exp. Ther.* 281(2):817-825 (1997).

Wakamiya et al., "Design and synthesis of peptides passing through the blood-brain barrier," *Bull. Chem. Soc. Jpn.* 71:699-709 (1998).

Zhou et al., "Peptide and protein drugs, I. Therapeutic applications, absorption and parental administration," *Int. J. Pharm.* 75:97-115 (1991).

English translation of the Abstract of FR 2708938, published Feb. 17, 1995.

Abstract of Larsen et al., "Structural Inducing Probes (SIP)- Blow New Hope Into the General Use of Peptides as Drugs," *Peptides*Proceedings of the European Peptide Symposium 26th (2000).

Adan et al., "Identification of Antagonists for Melanocortin MC3, MC4 and MC5 Receptors," *Eur. J. Pharmacol.*269:331-337 (1994).

Bagutti et al., "[111In]-DTPA-Labeled Analogues of Alpha-Melanocyte-Stimulating Hormone for Melanoma Targeting: Receptor Binding *In Vitro and in Vivo*," Int. J. Cancer 58:749-755 (1994).

Barrett et al., "Cloning and Expression of a New Member of the Melanocyte-Stimulating Hormone Receptor Family," *J. Mol. Endocrinol.* 12:203-213 (1994).

Bedford et al., "Amino Acid Structure and 'Difficult Sequences' in Solid Phase Peptide Synthesis," *Int. J. Peptide Protein Res.*40:300-307 (1992).

Bhardwaj et al., "Pro-Opiomelanocortin-Derived Peptides Induce IL-10 Production in Human Monocytes," J. Immunol. 156:2517-2521 (1996).

Boyfield et al., "Comparison of Agonist Potencies at Human Dopamine D2 and D3 Receptors, Expressed in the Same Cell Line, Using the Cytosensor Microphysiometer," Biochem. Soc. Trans. 24:57S (1996).

Campbell, "Lipofection Reagents Prepared by a Simple Ethanol Injection Technique," *Biotechniques*18:1027-1032 (1995).

Canevari et al., "Bispecific Antibody Targeted T Cell Therapy of Ovarian Cancer: Clinical Results and Future Directions," *J. Hematother.*4:423-427 (1995).

Catania et al., "The Neuropeptide Alpha-MSH Has Specific Receptors on Neutrophils and Reduces Chemotaxis in Vitro," *Peptides*17:675-679 (1996).

Chen et al., "A Colorimetric Assay for Measuring Activation of Gs- and Gq-Coupled Signaling Pathways," Anal. Biochem. 226:349-354 (1995).

Chhajlani et al., "Molecular Cloning and Expression of the Human Melanocyte Stimulating Hormone Receptor cDNA," *FEBS Lett.* 309:417-420 (1992).

Chhajlani et al., "Molecular Cloning of a Novel Human Melanocortin Receptor," Biochem. Biophys. Res. Commun. 195:866-873 (1993).

Chhajlani, "Distribution of cDNA for Melanocortin Receptor Subtypes in Human Tissues," Biochem. Mol. Biol. Int 38:73-80 (1996).

Chluba-de Tapia et al., "Induction of Constitutive Melanogenesis in Amelanotic Mouse Melanoma Cells by Transfection of the Human Melanocortin-1 Receptor Gene," J. Cell Sci. 109:2023-2030 (1996).

Christensen et al., "Neuropharmacological Aspects of Hypothalamic Peptides and Alpha-MSH," *Current Studies of Hypothalamic Function*1:182-191 (1978).

Cone et al., "The Melanocortin Receptors: Agonists, Antagonists, and the Hormonal Control of Pigmentation," *Recent Prog. Horm. Res.*51:287-317 (1996).

Desarnaud et al., "Molecular Cloning, Functional Expression and Pharmacological Characterization of a Mouse Melanocortin Receptor Gene," Biochem. J. 299:367-373 (1994).

Datta et al., "Alpha-Melanocyte-Stimulating Hormone and Behavior," *Neurosci. Biobehay. Rev.*6:297-310 (1982).

De Wied et al., "Neuropeptides Derived From Pro-Opiocortin: Behavioral, Physiological, and Neurochemical Effects," Physiol Rev. 62:976-1059 (1982).

De Wildt et al., "Effect of Gamma 2-Melanocyte-Stimulating Hormone on Cerebral Blood Flow in Rats," J. Cardiovasc. Pharmacol. 25:898-905 (1995).

Eberle, "Structure-Activity Relationships of the Melanotropins," In *The Melanotropins: Chemistry, Physiology and Mechanisms of Action*, 333-379 (1988).

Ehrlich, "DNA Cloning in Bacillus Subtilis," *Proc. Natl. Acad. Sci. U.S.A.* 75:1433-1436 (1978).

Fan et al., "Role of Melanocortinergic Neurons in Feeding and the Agouti Obesity Syndrome," *Nature*385:165-168 (1997).

Fathi et al., "Cloning, Expression, and Tissue Distribution of a Fifth Melanocortin Receptor Subtype," Neurochem. Res. 20:107-113 (1995).

Feng et al., "Effects of Preoptic Microinjections of Alpha-MSH On Fever and Normal Temperature Control in Rabbits," Brain Res. Bull. 18:473-477 (1987).

Friedman, "The Alphabet of Weight Control," *Nature*385:119-120 (1997).

Fukuta et al. "Insulin Fragments as a Carrier for Peptide Delivery Across the Blood-Brain Barrier," Pharm. Res. 11:1681-1688 (1994).

Gantz et al., "Molecular Cloning of a Novel Melanocortin Receptor," J. Biol. Chem. 268:8246-8250 (1993).

Gantz et al., "Molecular Cloning, Expression, and Gene Localization of a Fourth Melanocortin Receptor," J. Biol. Chem. 268:15174-15179 (1993).

Gantz et al., "Molecular Cloning, Expression, and Characterization of a Fifth Melanocortin Receptor," *Biochem. Biophys. Res. Commun.* 200:1214-1220 (1994).

Garrud et al., "Pituitary-Adrenal Hormones and Extinction of Rewarded Behavior in the Rat," Physiol. Psychol. 112:109-119 (1974).

Gilbert et al., "Useful Proteins From Recombinant Bacteria," Sci. Am. 242:74-94 (1980).

Gonindard et al., "The Administration of an Alpha-MSH Analogue Reduces the Serum Release of IL-1 Alpha and TNF Alpha Induced by the Injection of a Sublethal Dose of Lipopolysaccharides in the BALB/c Mouse," Pigment Cell Res.9:148-153 (1996).

Griffon et al., "Molecular Cloning and Characterization of the Fifth Melanocortin Receptor," Biochem. Biophys. Res. Commun. 200:1007-1014 (1994).

Gruber et al., "ACTH-(4-10) Through Gamma-MSH: Evidence for a New Class of Central Autonomic Nervous System-Regulating Peptides," Am. J. Physiol. 257:681-694 (1989).

Guo et al., "3'-End-Forming Signals of Yeast mRNA," Mol. Cell Biol.15:5983-5990 (1995).

Hartmeyer et al., "Human Dermal Microvascular Endothelial Cells Express the Melanocortin Receptor Type 1 and Produce Increased Levels of IL-8 Upon Stimulation With Alpha-Melanocyte-Stimulating Hormone," J. Immunol. 159:1930-1937 (1997).

Hiltz et al., "Anti-Inflammatory Activity of Alpha-MSH(11-13) Analogs: Influences of Alteration in Stereochemistry," Peptides12:767-771 (1991).

Hnatowich et al., "ACTH Receptors in Nervous Tissue. High Affinity Binding-Sequestration of [125I]Phe2,Nle4 ACTH 1-24 in Homogenates and Slices From Rat Brain," Can. J. Physiol. Pharmacol.67:568-576 (1989).

Hol et al., "Protection by an ACTH4-9 Analogue Against the Toxic Effects of Cisplatin and Taxol on Sensory Neurons and Glial Cells in Vitro," J. Neurosci. Res.39:178-185 (1994).

Hruby et al., "Cyclic Lactam Alpha-Melanotropin Analogues of Ac-Nle4-cyclo[Asp5, D-Phe7,Lys10] AlphaMelanocyte-Stimulating Hormone-(4-10)-NH2 With Bulky Aromatic Amino Acids at Position 7 Show High Antagonist Potency and Selectivity at Specific Melanocortin Receptors," J. Med. Chem.38:3454-3461 (1995).

Klein et al., "Pressor and Cardioaccelerator Effects of Gamma MSH and Related Peptides," Life Sci.36:769-775 (1985).

Knittel et al., "Structure-Activity Studies of Highly Potent Cyclic [Cys4,Cys10]Melanotropin Analogues," J. Med Chem.26:125-129 (1983).

Krchnak et al., "Aggregation of Resin-Bound Peptides Using Solid-Phase Peptide Synthesis," Int. J. Peptide Protein Res.42:450-454 (1993).

Kullmann, "Proteases as Biocatalysts for the Synthesis of Model Peptides," Enzymatic Peptide Synthesis7:41-59 (1987).

Labbéet al., "Molecular Cloning of a Mouse Melanocortin 5 Receptor Gene Widely Expressed in Peripheral Tissues," Biochemistry 33:4543-4549 (1994).

Larsen et al., "Sequence-Assisted Peptide Synthesis (SAPS)," J. Peptide Res.52:470-476 (1998).

Lichtensteiger et al., "Pre- and Postnatal Ontogeny of [125I]Nle4,D-Phe7-Alpha-MSH Binding Sites in Rat Brain," Ann. N.Y. Acad. Sci. 680:652-654 (1993).

Lin et al., "A Gamma-Melanocyte Stimulating Hormone-Like Peptide Causes Reflex Natriuresis After Acute Unilateral Nephrectomy," Hypertension10:619-627 (1987).

Lipton et al., "Anti-Inflammatory Actions of the Neuroimmunomodulator Alpha-MSH," Immunol.Today 18:140-145 (1997).

Liu et al., "Orthogonal Ligation of Unprotected Peptide Segments Through Pseudoproline Formation for the Synthesis of HIV-1 Protease Analogs," J. Chem. Soc.118:307-312 (1996).

Low et al., "Receptors for the Melanocortin Peptides in the Central Nervous System," Curr. Opin. Endocr. Diab.79 (1994).

Luger et al., "The Role of Alpha-Melanocyte-Stimulating Hormone in Cutaneous Biology," J. Investig. Dermatol. Symp. Proc.2:87-93 (1997).

Luger et al., "The Proopiomelanocortin System in Cutaneous Neuroimmunomodulation: An Introductory Overview," Ann. N Y Acad. Sci.885:xi-xiv (1999).

Luger et al., "Alpha-MSH Related Peptides: a New Class of Anti-Inflammatory and Immunomodulating Drugs," Ann. Rheum Dis. 66:iii52-iii55 (2007).

Mountjoy et al., "The Cloning of a Family of Genes that Encode the Melanocortin Receptors," Science 257:1248-1251 (1992).

Mountjoy et al., "Localization of the Melanocortin-4 Receptor (MC4-R) in Neuroendocrine and Autonomic Control Circuits in the Brain," Mol. Endocrinol.8:1298-1308 (1994).

Mukherji et al., "Immunobiology and Immunotherapy of Melanoma," Curr. Opin. Oncol.7:175-184 (1995).

Murphy et al., "Genetic Construction, Expression, and Melanoma-Selective Cytotoxicity of a Diphtheria Toxin-Related Alpha-Melanocyte-Stimulating Hormone Fusion Protein," Proc. Natl. Acad. Sci.U.S.A. 83:8258-8262 (1986).

Nordstedt et al., "A Modification of a Protein-Binding Method for Rapid Quantification of cAMP in Cell-Culture Supernatants and Body Fluid," Anal. Biochem.189:231-234 (1990).

O'Donahue et al., "Comparison of Biological and Behavioral Activities of Alpha- and Gamma Melanocyte Stimulating Hormones," Peptides2:101-104 (1981).

O'Donahue et al., "The Opiomelanotropinergic Neuronal and Endocrine Systems," Peptides3:353-395 (1982).

O'Hare et al., "Polymeric Drug-Carriers Containing Doxorubicin and Melanocyte-Stimulating Hormone: In Vitro and In Vivo Evaluation Against Murine Melanoma," J. Drug Target. 1:217-229 (1993).

Patel et al., "Peptide Targeting and Delivery Across the Blood-Brain Barrier Utilizing Synthetic Triglyceride Esters: Design, Synthesis, and Bioactivity," Bioconjug. Chem.8:434-441 (1997).

Prokai-Tatrai et al., "Brain-Targeted Delivery of a Leucine-Enkephalin Analogue by Retrometabolic Design," J. Med. Chem. 39:4775-4782 (1996).

Prusis et al., "A Three Dimensional Model for the Interaction of MSH With the Melanocortin-1 Receptor," Biochem. Biophys. Res. Commun.210:205-210 (1995).

Rajora et al., "Alpha-MSH Modulates Local and Circulating Tumor Necrosis Factor-Alpha in Experimental Brain Inflammation," J. Neurosci.17:2181-2186 (1997).

Rajora et al., "Alpha-MSH Modulates Experimental Inflammatory Bowel Disease," Peptides18:381-385 (1997).

Riedle et al., "In Vivo Activation and Expansion of T Cells by a Bi-Specific Antibody Abolishes Metastasis Formation of Human Melanoma Cells in SCID Mice," Int. J. Cancer. 75:908-918 (1998).

Rizzi et al., "Pharmacological Characterization of the Novel Nociceptin/Orphanin FQ Receptor Ligand, ZP120: in Vitro and in Vivo Studies in Mice," Br. J. Pharmacol.137:369-374 (2002).

Romanos et al., "Foreign Gene Expression in Yeast: a Review," Yeast8:423-488 (1992).

Roselli-Rehfuss et al., "Identification of a Receptor for Gamma Melanotropin and Other Proopiomelanocortin Peptides in the Hypothalamus and Limbic System," Proc. Natl. Acad. Sci.U.S.A. 90:8856-8860 (1993).

Saito et al., "Vector-Mediated Delivery of 125I-Labeled Beta-Amyloid Peptide a Beta 1-40 Through the Blood-Brain Barrier and Binding to Alzheimer Disease Amyloid of the A Beta 1-40/Vector Complex," Proc. Natl. Acad. Sci.U.S.A. 92:10227-10231 (1995).

Sawyer et al., "4-Norleucine, 7-D-Phenylalanine-Alpha-Melanocyte-Stimulating Hormone: a Highly Potent Alpha-Melanotropin With Ultralong Biological Activity," Proc. Natl. Sci.U.S.A. 77:5754-5758 (1980).

Sawyer et al., "[half-Cys4,half-Cys10]-Alpha-Melanocyte-Stimulating Hormone: A Cyclic Alpha-Melanotropin Exhibiting Superagonist Biological Activity," Proc. Natl. Acad. Sci.U.S.A. 79:1751-1755 (1982).

Schiöth et al., "Characterisation of Melanocortin Receptor Subtypes by Radioligand Binding Analysis," Eur. J. Pharmacol.288:311-317 (1995).

Schiöth et al., "Expression of Functional Melanocortin 1 Receptors in Insect Cells," Biotchem. Biophys. Res. Commun.221:807-814 (1996).

Schiöth et al., "Major Pharmacological Distinction of the ACTH Receptor From Other Melanocortin Receptors," Life Sci.59:797-801 (1996).

Schiöth et al., "Binding of Cyclic and Linear MSH Core Peptides to the Melanocortin Receptor Subtypes," Eur. J. Pharmacol.319:369-373 (1997).

Schiöth et al., "Selective Properties of C- and N-Terminals and Core Residues of the Melanocyte-Stimulating Hormone on Binding to the Human Melanocortin Receptor Subtypes," *Eur. J. Pharmacol.* 349:359-366 (1998).

Siegrist et al., "Melanocortins and Their Implications in Melanoma," *Trends Endocrinol. Metab.* 6:115-120 (1995).

Simpson et al., "Regulation of the Synthesis of Steroidogenic Enzymes in Adrenal Cortical Cells by ACTH," *Ann. Rev. Physiol.* 50:427-440 (1988).

Solca et al., "B16-G4F Mouse Melanoma Cells: an MSH Receptor-Deficient Cell Clone," *FEBS Lett.* 322:177-180 (1993).

Star et al., "Evidence of Autocrine Modulation of Macrophage Nitric Oxide Synthase by Alpha-Melanocyte-Stimulating Hormone," *Proc. Natl. Acad. Sci.* U.S.A. 92:8016-8020 (1995).

English Translation of Syskov et al., "Structural-Functional Organization of ACTH: Synthesis and Properties of Analogues of the ACTH-(11-24)-Tetradeca- and ACTH-(1-24)-Tetracosapeptides Containing Hexa(Amino Acids) in Place of the Natural ACTH 19-24 Sequence of Amino Acids," *Bioorganischeskaya Khimiya* 10:618-625 (1984). (4 pages).

Szardenings et al., "Phage Display Selection on Whole Cells Yields a Peptide Specific for Melanocortin Receptor 1," *J. Biol. Chem.* 272:27943-27948 (1997).

Szardenings et al., "New Highly Specific Agonistic Peptides for Human Melanocortin MC(1) Receptor," *Peptides* 21:239-243 (2000).

Tatro et al., "Specific Receptors for Alpha-Melanocyte-Stimulating Hormone Are Widely Distributed in Tissues of Rodents," *Endocrinology* 121:1900-1907 (1987).

Tatro et al., "Interaction of an Alpha-Melanocyte-Stimulating Hormone-Diphtheria Toxin Fusion Protein With Melanotropin Receptors in Human Melanoma Metastases," *Can. Res.* 52:2545-2548 (1992).

Tatro et al., "Heterogeneity of Brain Melanocortin Receptors Suggested by Differential Ligand Binding in Situ," *Brain Res.* 635:148-158 (1994).

Thielemans, "Immunotherapy with Bispecific Antibodies," *Verh. K. Acad. Geneeskd Belg.* 57:229-248 (1995).

Thörnwall et al., "Immunohistochemical Detection of the Melanocortin 1 Receptor in Human Testis, Ovary and Placenta Using Specific Monoclonal Antibody," *Horm. Res.* 48:215-218 (1997).

Toth, "A Novel Chemical Approach to Drug Delivery: Lipidic Amino Acid Conjugates," *J. Drug Target* 2:217-239 (1994).

Vanetti et al., "Molecular Cloning of a Bovine MSH Receptor Which Is Highly Expressed in the Testis," *FEBS Lett.* 348:268-272 (1994).

Wiegant et al., "Intracerebroventricular ACTH Activates the Pituitary-Adrenal System: Dissociation From a Behavioral Response," *Life Sci.* 25:1791-1796 (1979).

Wikberg, "Melanocortin Receptors: Perspectives for Novel Drugs," *Eur. J. Pharmacol.* 375:295-310 (1999).

Wong et al., "A Potential Mechanism of Local Anti-Inflammatory Action of Alpha-Melanocyte-Stimulating Hormone Within the Brain: Modulation of Tumor Necrosis Factor-Alpha Production by Human Astrocytic Cells," *Neuroimmunomodulation* 4:37-41 (1997).

Wu et al., "Central Nervous System Pharmacologic Effect in Conscious Rats After Intravenous Injection of a Biotinylated Vasoactive Intestinal Peptide Analog Coupled to a Blood-Brain Barrier Drug Delivery System," *J. Pharmacol. Exp. Ther.* 279:77-83 (1996).

Xia et al., "Expression of Melanocortin 1 Receptor in Periaqueductal Gray Matter," *Neuroreport* 6:2193-2196 (1995).

Xia, "Immunological Localisation of Melanocortin 1 Receptor on the Cell Surface of WM266-4 Human Melanoma Cells," *Cancer Lett.* 98:157-162 (1996).

Zlokovic, "Cerebrovascular Permeability to Peptides: Manipulations of Transport Systems at the Blood-Brain Barrier," *Pharm. Res.* 12:1395-1406 (1995).

European Search Report for EP 07010570.5, completed on Oct. 10, 2008.

European Search Report for EP 07021432.5, completed on Apr. 1, 2009.

Reply to Communication for EP 07010570.5, filed on Jan. 11, 2010.

* cited by examiner

SEQUENCE LISTING

```
<160> NUMBER OF SEQ ID NOS: 134

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Pen

<400> SEQUENCE: 1

Tyr Xaa Gly Phe Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
```

<223> OTHER INFORMATION: Xaa = D-Pen

<400> SEQUENCE: 2

Tyr Xaa Gly Phe Cys Arg Pro Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Pen
<220> FEATURE:
<221> NAME/KEY: MISC_FEATURE
<222> LOCATION: (5)..(5)
<223> OTHER INFORMATION: Xaa = D-Pen

<400> SEQUENCE: 3

Tyr Xaa Gly Phe Xaa Phe
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Pen

<400> SEQUENCE: 4

Tyr Xaa Gly Phe Cys Phe
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Pen
<220> FEATURE:
<221> NAME/KEY: MISC_FEATURE
<222> LOCATION: (5)..(5)
<223> OTHER INFORMATION: Xaa = D-Pen

<400> SEQUENCE: 5

Tyr Xaa Gly Phe Xaa Arg Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Pen

<400> SEQUENCE: 6

```
Tyr Xaa Gly Phe Cys Arg Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Pen
<220> FEATURE:
<221> NAME/KEY: MISC_FEATURE
<222> LOCATION: (5)..(5)
<223> OTHER INFORMATION: Xaa = D-Pen

<400> SEQUENCE: 7

Tyr Xaa Gly Phe Xaa Phe Ala
1               5

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Trp Ala Gly Gly Asp Ala Ser Gly Glu Lys Glu Lys Glu Lys Glu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Trp Ala Gly Gly Asp Ala Ser Gly Glu Glu Glu Glu Glu Glu Glu
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Tyr Gly Gly Phe Leu Glu Glu Glu Glu Glu Glu
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Tyr Gly Gly Phe Leu Lys Lys Lys Lys Lys Lys
1               5                   10

<210> SEQ ID NO 12
<211> LENGTH: 5
<212> TYPE: PRT
```

```
<213> ORGANISM: Homo sapiens

<400> SEQUENCE: 12

Tyr Gly Gly Phe Leu
1               5

<210> SEQ ID NO 13
<211> LENGTH: 9
<212> TYPE: PRT
<213> ORGANISM: Homo sapiens

<400> SEQUENCE: 13

Cys Tyr Ile Gln Asn Cys Pro Leu Gly
1               5

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Ile Glu Gly Pro Thr Leu Arg Gln Trp Leu Ala Ala Arg Ala
1               5                   10

<210> SEQ ID NO 15
<211> LENGTH: 14
<212> TYPE: PRT
<213> ORGANISM: Homo sapiens

<400> SEQUENCE: 15

Ala Leu Leu Glu Thr Tyr Cys Ala Thr Pro Ala Lys Ser Glu
1               5                   10

<210> SEQ ID NO 16
<211> LENGTH: 12
<212> TYPE: PRT
<213> ORGANISM: Homo sapiens

<400> SEQUENCE: 16

Gly Tyr Gly Ser Ser Ser Arg Arg Ala Pro Gln Thr
1               5                   10

<210> SEQ ID NO 17
<211> LENGTH: 18
<212> TYPE: PRT
<213> ORGANISM: Homo sapiens

<400> SEQUENCE: 17

Tyr Phe Asn Lys Pro Thr Gly Tyr Gly Ser Ser Ser Arg Arg Ala Pro
1               5                   10                  15

Gln Thr

<210> SEQ ID NO 18
<211> LENGTH: 8
<212> TYPE: PRT
<213> ORGANISM: Homo sapiens

<400> SEQUENCE: 18

Ser Arg Val Ser Arg Arg Ser Arg
1               5

<210> SEQ ID NO 19
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 19

Tyr Ser Arg Val Ser Arg Arg Ser Arg
1               5

<210> SEQ ID NO 20
<211> LENGTH: 16
<212> TYPE: PRT
<213> ORGANISM: Homo sapiens

<400> SEQUENCE: 20

Asp Val Ser Thr Pro Pro Thr Val Leu Pro Asp Asn Phe Pro Arg Tyr
1               5                   10                  15

<210> SEQ ID NO 21
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Trp
<220> FEATURE:
<221> NAME/KEY: MISC_FEATURE
<222> LOCATION: (5)..(5)
<223> OTHER INFORMATION: Xaa = D-Phe

<400> SEQUENCE: 21

His Xaa Ala Trp Xaa Lys
1               5

<210> SEQ ID NO 22
<211> LENGTH: 9
<212> TYPE: PRT
<213> ORGANISM: Homo sapiens

<400> SEQUENCE: 22

Val Gln Gly Glu Glu Ser Asn Asp Lys
1               5

<210> SEQ ID NO 23
<211> LENGTH: 13
<212> TYPE: PRT
<213> ORGANISM: Homo sapiens

<400> SEQUENCE: 23

Ile Leu Asn Gly Ile Asn Asn Tyr Lys Asn Pro Lys Leu
1               5                   10

<210> SEQ ID NO 24
<211> LENGTH: 11
<212> TYPE: PRT
<213> ORGANISM: Homo sapiens

<400> SEQUENCE: 24

Leu Thr Phe Lys Phe Tyr Met Pro Lys Lys Ala
1               5                   10

<210> SEQ ID NO 25
<211> LENGTH: 39
<212> TYPE: PRT
<213> ORGANISM: Heloderma suspectum
```

```
<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 26
<211> LENGTH: 39
<212> TYPE: PRT
<213> ORGANISM: Heloderma horridum

<400> SEQUENCE: 26

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 27
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Cys (Acm)
<220> FEATURE:
<221> NAME/KEY: MISC_FEATURE
<222> LOCATION: (12)..(12)
<223> OTHER INFORMATION: Xaa = Cys (Acm)

<400> SEQUENCE: 27

Xaa Met His Ile Glu Ser Leu Asp Ser Tyr Thr Xaa
1               5                   10

<210> SEQ ID NO 28
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = D-Phe

<400> SEQUENCE: 28

Xaa Pro Arg Pro Gly Gly Gly Gly Asn Gly Asp Phe Glu Glu Ile Pro
1               5                   10                  15

Glu Glu Tyr Leu
            20

<210> SEQ ID NO 29
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Xaa = D-Phe

<400> SEQUENCE: 29

Xaa Pro Arg Pro Gly Gly Gly Asn Gly Asp Phe Glu Glu Ile Pro
1               5                   10                  15

Glu Tyr Leu

<210> SEQ ID NO 30
<211> LENGTH: 53
<212> TYPE: PRT
<213> ORGANISM: Homo sapiens
<220> FEATURE:
<221> NAME/KEY: DISULFID
<222> LOCATION: (37)..(53)
<223> OTHER INFORMATION: Disulfide bridge between positions 37 and 53

<400> SEQUENCE: 30

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 31
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (2)..(13)
<223> OTHER INFORMATION: disulfide bridge between positions 2 and 13
<220> FEATURE:
<221> NAME/KEY: MISC_FEATURE
<222> LOCATION: (4)..(4)
<223> OTHER INFORMATION: Xaa =cyclohexyl-Ala

<400> SEQUENCE: 31

Met Cys His Xaa Gly Gly Arg Met Asp Arg Ile Ser Cys Tyr Arg
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: MISC_FEATURE
<222> LOCATION: (4)..(4)
<223> OTHER INFORMATION: Xaa = D-Phe

<400> SEQUENCE: 32

Xaa Asp His Xaa Arg Trp Lys
1               5

<210> SEQ ID NO 33
<211> LENGTH: 28
<212> TYPE: PRT
<213> ORGANISM: Artificial Sequence
```

```
<220> FEATURE:
<223> OTHER INFORMATION: Synthetic

<400> SEQUENCE: 33

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25

<210> SEQ ID NO 34
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (1)..(6)
<223> OTHER INFORMATION: Disulfide bridge between positions 1 and 6
<220> FEATURE:
<221> NAME/KEY: MISC_FEATURE
<222> LOCATION: (8)..(8)
<223> OTHER INFORMATION: Xaa = Orn

<400> SEQUENCE: 34

Cys Phe Ile Gln Asn Cys Pro Xaa Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DISULFID
<222> LOCATION: (2)..(7)
<223> OTHER INFORMATION: Disulfide bridge between positions 2 and 7
<220> FEATURE:
<221> NAME/KEY: MISC_FEATURE
<222> LOCATION: (4)..(4)
<223> OTHER INFORMATION: Xaa = D-Trp
<220> FEATURE:
<221> NAME/KEY: MISC_FEATURE
<222> LOCATION: (8)..(8)
<223> OTHER INFORMATION: Xaa = Thr-ol

<400> SEQUENCE: 35

Xaa Cys Phe Xaa Lys Thr Cys Xaa
1               5

<210> SEQ ID NO 36
<211> LENGTH: 37
<212> TYPE: PRT
<213> ORGANISM: Homo sapiens
<220> FEATURE:
<221> NAME/KEY: DISULFID
<222> LOCATION: (2)..(7)
<223> OTHER INFORMATION: disulfide bridge between positions 2 and 7

<400> SEQUENCE: 36

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
```

<210> SEQ ID NO 37
<211> LENGTH: 4
<212> TYPE: PRT
<213> ORGANISM: Homo sapiens

<400> SEQUENCE: 37

Tyr Pro Trp Phe
1

<210> SEQ ID NO 38
<211> LENGTH: 4
<212> TYPE: PRT
<213> ORGANISM: Homo sapiens

<400> SEQUENCE: 38

Tyr Pro Phe Phe
1

<210> SEQ ID NO 39
<211> LENGTH: 17
<212> TYPE: PRT
<213> ORGANISM: Homo sapiens

<400> SEQUENCE: 39

Phe Gly Gly Phe Thr Gly Ala Arg Lys Ser Ala Arg Lys Leu Ala Asn
1               5                   10                  15

Gln

<210> SEQ ID NO 40
<211> LENGTH: 13
<212> TYPE: PRT
<213> ORGANISM: Homo sapiens

<400> SEQUENCE: 40

Asp Arg Val Tyr Ile His Pro Phe His Leu Val Ile His
1               5                   10

<210> SEQ ID NO 41
<211> LENGTH: 12
<212> TYPE: PRT
<213> ORGANISM: Homo sapiens

<400> SEQUENCE: 41

Tyr Arg Gln Ser Met Asn Asn Phe Gln Gly Leu Arg
1               5                   10

<210> SEQ ID NO 42
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa = Hyp

<400> SEQUENCE: 42

Gly Pro Xaa Gly Ala Gly
1               5

<210> SEQ ID NO 43
<211> LENGTH: 13
<212> TYPE: PRT

```
<213> ORGANISM: Bos sp.

<400> SEQUENCE: 43

Ile Leu Pro Trp Lys Trp Pro Trp Trp Pro Trp Arg Arg
1               5                   10

<210> SEQ ID NO 44
<211> LENGTH: 13
<212> TYPE: PRT
<213> ORGANISM: Homo sapiens

<400> SEQUENCE: 44

Gly Phe Gln Glu Ala Tyr Arg Arg Phe Tyr Gly Pro Val
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Glp

<400> SEQUENCE: 45

Xaa Glu Arg Pro Pro Leu Gln Gln Pro Pro His Arg Asp
1               5                   10

<210> SEQ ID NO 46
<211> LENGTH: 14
<212> TYPE: PRT
<213> ORGANISM: Homo sapiens
<220> FEATURE:
<221> NAME/KEY: DISULFID
<222> LOCATION: (2)..(13)
<223> OTHER INFORMATION: disulfide bridge between positions 2 and 13

<400> SEQUENCE: 46

Pro Cys Lys Asn Phe Phe Trp Lys Thr Phe Ser Ser Cys Lys
1               5                   10

<210> SEQ ID NO 47
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = D-Bhg

<400> SEQUENCE: 47

Xaa Leu Asp Ile Ile Trp
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = D-Dip

<400> SEQUENCE: 48
```

```
Xaa Leu Asp Ile Ile Trp
1               5
```

<210> SEQ ID NO 49
<211> LENGTH: 12
<212> TYPE: PRT
<213> ORGANISM: Artificial Sequence
<220> FEATURE:
<223> OTHER INFORMATION: Synthetic

<400> SEQUENCE: 49

```
His His Leu Gly Gly Ala Lys Gln Ala Gly Asp Val
1               5                   10
```

<210> SEQ ID NO 50
<211> LENGTH: 13
<212> TYPE: PRT
<213> ORGANISM: Homo sapiens

<400> SEQUENCE: 50

```
Asn Val Ile Gln Ile Ser Asn Asp Leu Glu Asn Leu Arg
1               5                   10
```

<210> SEQ ID NO 51
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Boc-Arg
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (5)..(5)
<223> OTHER INFORMATION: Xaa = D-Pro
<220> FEATURE:
<221> NAME/KEY: MISC_FEATURE
<222> LOCATION: (7)..(7)
<223> OTHER INFORMATION: Xaa = Nle

<400> SEQUENCE: 51

```
Xaa Ala Xaa Phe Xaa Pro Xaa
1               5
```

<210> SEQ ID NO 52
<211> LENGTH: 4
<212> TYPE: PRT
<213> ORGANISM: Homo sapiens

<400> SEQUENCE: 52

```
Tyr Pro Trp Gly
1
```

<210> SEQ ID NO 53
<211> LENGTH: 5
<212> TYPE: PRT
<213> ORGANISM: Homo sapiens

<400> SEQUENCE: 53

```
Thr Arg Ser Ala Trp
1               5
```

```
<210> SEQ ID NO 54
<211> LENGTH: 14
<212> TYPE: PRT
<213> ORGANISM: Homo sapiens

<400> SEQUENCE: 54

Asp Arg Val Tyr Ile His Pro Phe His Leu Val Ile His Asn
1               5                   10

<210> SEQ ID NO 55
<211> LENGTH: 4
<212> TYPE: PRT
<213> ORGANISM: Artificial Sequence
<220> FEATURE:
<223> OTHER INFORMATION: Synthetic

<400> SEQUENCE: 55

Lys Lys Lys Lys
1

<210> SEQ ID NO 56
<211> LENGTH: 5
<212> TYPE: PRT
<213> ORGANISM: Artificial Sequence
<220> FEATURE:
<223> OTHER INFORMATION: Synthetic

<400> SEQUENCE: 56

Lys Lys Lys Lys Lys
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 57

Xaa Lys Lys Lys Lys
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 58

Lys Xaa Lys Lys Lys
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (3)..(3)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 59

Lys Lys Xaa Lys Lys
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 60

Lys Lys Lys Xaa Lys
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 61

Lys Lys Lys Lys Xaa
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic

<400> SEQUENCE: 62

Lys Lys Lys Lys Lys Lys
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 63

Xaa Lys Lys Lys Lys Lys
1               5

<210> SEQ ID NO 64
<211> LENGTH: 6
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 64

Lys Xaa Lys Lys Lys Lys
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 65

Lys Lys Xaa Lys Lys Lys
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 66

Lys Lys Lys Xaa Lys Lys
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 67

Lys Lys Lys Lys Xaa Lys
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa = Ala, Leu, Ser, Thr, Tyr, Asn, Gln, Asp,
```

```
            Glu, Arg, His, Met, Orn, Dbu, or DPr

<400> SEQUENCE: 68

Lys Lys Lys Lys Lys Xaa
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 69

Xaa Xaa Lys Lys Lys Lys
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (3)..(3)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 70

Xaa Lys Xaa Lys Lys Lys
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (4)..(4)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 71

Xaa Lys Lys Xaa Lys Lys
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (5)..(5)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 72

Xaa Lys Lys Lys Xaa Lys
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (6)..(6)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 73

Xaa Lys Lys Lys Lys Xaa
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 74

Lys Xaa Xaa Lys Lys Lys
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (4)..(4)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 75

Lys Xaa Lys Xaa Lys Lys
1               5

<210> SEQ ID NO 76
```

```
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (5)..(5)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 76

Lys Xaa Lys Lys Xaa Lys
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (6)..(6)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 77

Lys Xaa Lys Lys Lys Xaa
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 78

Lys Lys Xaa Xaa Lys Lys
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (5)..(5)
<223> OTHER INFORMATION: Xaa = Ala, Leu, Ser, Thr, Tyr, Asn, Gln, Asp,
      Glu, Arg, His, Met, Orn, Dbu, or DPr
```

```
<400> SEQUENCE: 79

Lys Lys Xaa Lys Xaa Lys
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (6)..(6)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 80

Lys Lys Xaa Lys Lys Xaa
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(5)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 81

Lys Lys Lys Xaa Xaa Lys
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa = Ala, Leu, Ser, Thr, Tyr, Asn, Gln, Asp,
      Glu, Arg, His, Met, Orn, Dbu, or DPr
<220> FEATURE:
<221> NAME/KEY: MISC_FEATURE
<222> LOCATION: (6)..(6)
<223> OTHER INFORMATION: Xaa = Ala, Leu, Ser, Thr, Tyr, Asn, Gln, Asp,
      Glu, Arg, His, Met, Orn, Dbu, or DPr

<400> SEQUENCE: 82

Lys Lys Lys Xaa Lys Xaa
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(6)
<223> OTHER INFORMATION: Xaa = Ala, Leu, Ser, Thr, Tyr, Asn, Gln, Asp,
```

-continued

Glu, Arg, His, Met, Orn, Dbu, or DPr

<400> SEQUENCE: 83

Lys Lys Lys Lys Xaa Xaa
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic

<400> SEQUENCE: 84

Lys Glu Lys Glu Lys Glu
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic

<400> SEQUENCE: 85

Glu Lys Glu Lys Glu Lys
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic

<400> SEQUENCE: 86

Lys Lys Lys Glu Glu Glu
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic

<400> SEQUENCE: 87

Glu Glu Glu Lys Lys Lys
1               5

<210> SEQ ID NO 88
<211> LENGTH: 50
<212> TYPE: PRT
<213> ORGANISM: Artificial Sequence
<220> FEATURE:
<223> OTHER INFORMATION: Synthetic

<400> SEQUENCE: 88

Tyr Ala Asp Ala Ile Phe Thr Asn Ser Tyr Arg Lys Val Leu Gly Gln
1              5                    10                 15

Leu Ser Ala Arg Lys Leu Leu Gln Asp Ile Met Ser Arg Gln Gln Gly
            20                    25                    30

Glu Ser Asn Gln Glu Arg Gly Ala Arg Ala Arg Leu Lys Lys Lys
        35                    40                    45

Lys Lys
   50

```
<210> SEQ ID NO 89
<211> LENGTH: 50
<212> TYPE: PRT
<213> ORGANISM: Artificial Sequence
<220> FEATURE:
<223> OTHER INFORMATION: Synthetic

<400> SEQUENCE: 89

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu Glu Glu Glu Glu
        35                  40                  45

Glu Glu
    50

<210> SEQ ID NO 90
<211> LENGTH: 40
<212> TYPE: PRT
<213> ORGANISM: Artificial Sequence
<220> FEATURE:
<223> OTHER INFORMATION: Synthetic

<400> SEQUENCE: 90

Lys Lys Lys Lys Lys Lys Ser Val Ser Glu Ile Gln Leu Met His Asn
1               5                   10                  15

Leu Gly Lys His Leu Asn Ser Met Glu Arg Val Glu Trp Leu Arg Lys
            20                  25                  30

Lys Leu Gln Asp Val His Asn Phe
        35                  40

<210> SEQ ID NO 91
<211> LENGTH: 40
<212> TYPE: PRT
<213> ORGANISM: Artificial Sequence
<220> FEATURE:
<223> OTHER INFORMATION: Synthetic

<400> SEQUENCE: 91

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Lys Lys Lys Lys Lys Lys
        35                  40

<210> SEQ ID NO 92
<211> LENGTH: 36
<212> TYPE: PRT
<213> ORGANISM: Artificial Sequence
<220> FEATURE:
<223> OTHER INFORMATION: Synthetic

<400> SEQUENCE: 92

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys Lys
            20                  25                  30

Lys Lys Lys Lys
        35
```

```
<210> SEQ ID NO 93
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa = Cys(Acm) or Cys
<220> FEATURE:
<221> NAME/KEY: MISC_FEATURE
<222> LOCATION: (15)..(15)
<223> OTHER INFORMATION: Xaa = Cys(Acm) or Cys

<400> SEQUENCE: 93

Gly Gly Thr Tyr Ser Xaa His Phe Gly Pro Leu Thr Trp Val Xaa Lys
1               5                   10                  15

Pro Gln Gly Gly Lys Lys Lys Lys Lys Lys
            20                  25

<210> SEQ ID NO 94
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa = Cys (Acm) or Cys
<220> FEATURE:
<221> NAME/KEY: MISC_FEATURE
<222> LOCATION: (21)..(21)
<223> OTHER INFORMATION: Xaa = Cys (Acm) or Cys

<400> SEQUENCE: 94

Lys Lys Lys Lys Lys Lys Gly Gly Thr Tyr Ser Xaa His Phe Gly Pro
1               5                   10                  15

Leu Thr Trp Val Xaa Lys Pro Gln Gly Gly
            20                  25

<210> SEQ ID NO 95
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa = Cys (Acm) or Cys
<220> FEATURE:
<221> NAME/KEY: MISC_FEATURE
<222> LOCATION: (21)..(21)
<223> OTHER INFORMATION: Xaa = Cys (Acm) or Cys

<400> SEQUENCE: 95

Lys Lys Lys Lys Lys Lys Gly Gly Thr Tyr Ser Xaa His Phe Gly Pro
1               5                   10                  15

Leu Thr Trp Val Xaa Lys Pro Gln Gly Gly Lys Lys Lys Lys Lys Lys
            20                  25                  30

<210> SEQ ID NO 96
<211> LENGTH: 11
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Xaa = Aib
<220> FEATURE:
<221> NAME/KEY: MISC_FEATURE
<222> LOCATION: (3)..(3)
<223> OTHER INFORMATION: Xaa = 2-D-Nal
<220> FEATURE:
<221> NAME/KEY: MISC_FEATURE
<222> LOCATION: (4)..(4)
<223> OTHER INFORMATION: Xaa = D-Phe

<400> SEQUENCE: 96

Xaa His Xaa Xaa Lys Lys Lys Lys Lys Lys
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Synthetic

<400> SEQUENCE: 97

Tyr Gly Gly Phe Leu Lys Lys Glu Glu Glu Lys
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic

<400> SEQUENCE: 98

Tyr Gly Gly Phe Leu Lys Glu Glu Glu Glu Lys
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Synthetic

<400> SEQUENCE: 99

Tyr Gly Gly Phe Leu Lys Glu Lys Glu Lys Glu
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(11)
<223> OTHER INFORMATION: Xaa = Dpr

<400> SEQUENCE: 100

Tyr Gly Gly Phe Leu Xaa Xaa Xaa Xaa Xaa Xaa
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 101

Lys Lys Lys Lys Lys Lys Tyr Gly Gly Phe Leu
1               5                   10

<210> SEQ ID NO 102
<211> LENGTH: 17
<212> TYPE: PRT
<213> ORGANISM: Artificial Sequence
<220> FEATURE:
<223> OTHER INFORMATION: Synthetic

<400> SEQUENCE: 102

Lys Lys Lys Lys Lys Lys Tyr Gly Gly Phe Leu Lys Lys Lys Lys
1               5                   10                  15

Lys

<210> SEQ ID NO 103
<211> LENGTH: 16
<212> TYPE: PRT
<213> ORGANISM: Homo sapiens

<400> SEQUENCE: 103

Glu His Trp Ser Tyr Gly Leu Arg Pro Gly Lys Lys Lys Lys Lys
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = pGlu or Glu

<400> SEQUENCE: 104

Xaa His Trp Ser Tyr Gly Leu Arg Pro Gly Lys Glu Lys Glu Lys Glu
1               5                   10                  15

<210> SEQ ID NO 105
<211> LENGTH: 40
<212> TYPE: PRT
<213> ORGANISM: Artificial Sequence
<220> FEATURE:
<223> OTHER INFORMATION: Synthetic

<400> SEQUENCE: 105

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Lys Glu Lys Glu Lys Glu
                35                  40

<210> SEQ ID NO 106
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(11)
<223> OTHER INFORMATION: Xaa = Orn
```

```
<400> SEQUENCE: 106

Tyr Gly Gly Phe Leu Xaa Xaa Xaa Xaa Xaa Xaa
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(11)
<223> OTHER INFORMATION: Xaa =Dbu

<400> SEQUENCE: 107

Tyr Gly Gly Phe Leu Xaa Xaa Xaa Xaa Xaa Xaa
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(11)
<223> OTHER INFORMATION: Xaa = Dpr

<400> SEQUENCE: 108

Tyr Gly Gly Phe Leu Xaa Xaa Xaa Xaa Xaa Xaa
1               5                   10

<210> SEQ ID NO 109
<211> LENGTH: 15
<212> TYPE: PRT
<213> ORGANISM: Artificial Sequence
<220> FEATURE:
<223> OTHER INFORMATION: Synthetic

<400> SEQUENCE: 109

Tyr Gly Gly Phe Leu Lys Lys Lys Lys Lys Lys Lys Lys Lys
1               5                   10                  15

<210> SEQ ID NO 110
<211> LENGTH: 9
<212> TYPE: PRT
<213> ORGANISM: Homo sapiens

<400> SEQUENCE: 110

Trp Ala Gly Gly Asp Ala Ser Gly Glu
1               5

<210> SEQ ID NO 111
<211> LENGTH: 17
<212> TYPE: PRT
<213> ORGANISM: Artificial Sequence
<220> FEATURE:
<223> OTHER INFORMATION: Synthetic

<400> SEQUENCE: 111

Arg Pro Lys Pro Gln Gln Phe Phe Gly Leu Met Lys Lys Lys Lys
1               5                   10                  15

Lys

<210> SEQ ID NO 112
```

```
<211> LENGTH: 11
<212> TYPE: PRT
<213> ORGANISM: Homo sapiens

<400> SEQUENCE: 112

Arg Pro Lys Pro Gln Gln Phe Phe Gly Leu Met
1               5                   10

<210> SEQ ID NO 113
<211> LENGTH: 17
<212> TYPE: PRT
<213> ORGANISM: Artificial Sequence
<220> FEATURE:
<223> OTHER INFORMATION: Synthetic

<400> SEQUENCE: 113

Lys Lys Lys Lys Lys Lys Arg Pro Lys Pro Gln Gln Phe Phe Gly Leu
1               5                   10                  15

Met

<210> SEQ ID NO 114
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa = Aib
<220> FEATURE:
<221> NAME/KEY: MISC_FEATURE
<222> LOCATION: (9)..(9)
<223> OTHER INFORMATION: Xaa = 2-D-Nal
<220> FEATURE:
<221> NAME/KEY: MISC_FEATURE
<222> LOCATION: (10)..(10)
<223> OTHER INFORMATION: Xaa = D-Phe

<400> SEQUENCE: 114

Lys Lys Lys Lys Lys Lys Xaa His Xaa Xaa Lys
1               5                   10

<210> SEQ ID NO 115
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = pGlu

<400> SEQUENCE: 115

Xaa His Trp Ser Tyr Gly Leu Arg Pro Gly
1               5                   10

<210> SEQ ID NO 116
<211> LENGTH: 16
<212> TYPE: PRT
<213> ORGANISM: Artificial Sequence
<220> FEATURE:
<223> OTHER INFORMATION: Synthetic

<400> SEQUENCE: 116

Lys Lys Lys Lys Lys Lys Gln His Trp Ser Tyr Gly Leu Arg Pro Gly
1               5                   10                  15

<210> SEQ ID NO 117
<211> LENGTH: 20
```

```
<212> TYPE: PRT
<213> ORGANISM: Artificial Sequence
<220> FEATURE:
<223> OTHER INFORMATION: Synthetic

<400> SEQUENCE: 117

Gly Gly Thr Tyr Ser Cys His Phe Gly Pro Leu Thr Trp Val Cys Lys
1               5                   10                  15

Pro Gln Gly Gly
            20

<210> SEQ ID NO 118
<211> LENGTH: 30
<212> TYPE: PRT
<213> ORGANISM: Homo sapiens

<400> SEQUENCE: 118

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 119
<211> LENGTH: 34
<212> TYPE: PRT
<213> ORGANISM: Homo sapiens

<400> SEQUENCE: 119

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 120
<211> LENGTH: 11
<212> TYPE: PRT
<213> ORGANISM: Artificial Sequence
<220> FEATURE:
<223> OTHER INFORMATION: Synthetic

<400> SEQUENCE: 120

Tyr Gly Gly Phe Leu Lys Glu Glu Glu Lys Lys
1               5                   10

<210> SEQ ID NO 121
<211> LENGTH: 11
<212> TYPE: PRT
<213> ORGANISM: Homo sapiens

<400> SEQUENCE: 121

Tyr Gly Gly Phe Leu Glu Glu Lys Glu Glu Glu
1               5                   10

<210> SEQ ID NO 122

<400> SEQUENCE: 122

000

<210> SEQ ID NO 123
<211> LENGTH: 6
<212> TYPE: PRT
<213> ORGANISM: Artificial Sequence
<220> FEATURE:
```

-continued

```
<223> OTHER INFORMATION: Synthetic
<220> FEATURE:
<221> NAME/KEY: MISC_FEATURE
<222> LOCATION: (2)..(2)
<223> OTHER INFORMATION: Xaa = D-Trp
<220> FEATURE:
<221> NAME/KEY: MISC_FEATURE
<222> LOCATION: (3)..(3)
<223> OTHER INFORMATION: Xaa = (nMe) - Phe
<220> FEATURE:
<221> NAME/KEY: MISC_FEATURE
<222> LOCATION: (4)..(4)
<223> OTHER INFORMATION: Xaa = D-Trp

<400> SEQUENCE: 123

Arg Xaa Xaa Xaa Leu Met
1               5

<210> SEQ ID NO 124
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(15)
<223> OTHER INFORMATION: Xaa = Lys or is absent

<400> SEQUENCE: 124

Lys Lys Lys Lys Xaa Xaa Xaa Xaa Xaa Xaa Xaa Xaa Xaa Xaa Xaa
1               5                   10                  15

<210> SEQ ID NO 125
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: This sequence includes 2 to 7 repeating units
      of (Lys-Xaa)
<220> FEATURE:
<221> NAME/KEY: MISC_FEATURE
<222> LOCATION: (2)..(2)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, or
      Met
<220> FEATURE:
<221> NAME/KEY: MISC_FEATURE
<222> LOCATION: (4)..(4)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, or
      Met
<220> FEATURE:
<221> NAME/KEY: MISC_FEATURE
<222> LOCATION: (5)..(5)
<223> OTHER INFORMATION: Xaa = Lys or is absent
<220> FEATURE:
<221> NAME/KEY: MISC_FEATURE
<222> LOCATION: (6)..(6)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
<221> NAME/KEY: MISC_FEATURE
<222> LOCATION: (7)..(7)
<223> OTHER INFORMATION: Xaa = Lys or is absent
<220> FEATURE:
<221> NAME/KEY: MISC_FEATURE
<222> LOCATION: (8)..(8)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
```

```
<221> NAME/KEY: MISC_FEATURE
<222> LOCATION: (9)..(9)
<223> OTHER INFORMATION: Xaa = Lys or is absent
<220> FEATURE:
<221> NAME/KEY: MISC_FEATURE
<222> LOCATION: (10)..(10)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
<221> NAME/KEY: MISC_FEATURE
<222> LOCATION: (11)..(11)
<223> OTHER INFORMATION: Xaa = Lys or is absent
<220> FEATURE:
<221> NAME/KEY: MISC_FEATURE
<222> LOCATION: (12)..(12)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
<221> NAME/KEY: MISC_FEATURE
<222> LOCATION: (13)..(13)
<223> OTHER INFORMATION: Xaa = Lys or is absent
<220> FEATURE:
<221> NAME/KEY: MISC_FEATURE
<222> LOCATION: (14)..(14)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent

<400> SEQUENCE: 125

Lys Xaa Lys Xaa Xaa Xaa Xaa Xaa Xaa Xaa Xaa Xaa Xaa Xaa
1               5                   10

<210> SEQ ID NO 126
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: This sequence includes 2 to 7 repeating units
      of (Xaa-Lys)
<220> FEATURE:
<221> NAME/KEY: MISC_FEATURE
<222> LOCATION: (1)..(1)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, or
      Met
<220> FEATURE:
<221> NAME/KEY: MISC_FEATURE
<222> LOCATION: (3)..(3)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, or
      Met
<220> FEATURE:
<221> NAME/KEY: MISC_FEATURE
<222> LOCATION: (5)..(5)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
<221> NAME/KEY: MISC_FEATURE
<222> LOCATION: (6)..(6)
<223> OTHER INFORMATION: Xaa = Lys or is absent
<220> FEATURE:
<221> NAME/KEY: MISC_FEATURE
<222> LOCATION: (7)..(7)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
<221> NAME/KEY: MISC_FEATURE
<222> LOCATION: (8)..(8)
<223> OTHER INFORMATION: Xaa = Lys or is absent
<220> FEATURE:
<221> NAME/KEY: MISC_FEATURE
```

```
<222> LOCATION: (9)..(9)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
<221> NAME/KEY: MISC_FEATURE
<222> LOCATION: (10)..(10)
<223> OTHER INFORMATION: Xaa = Lys or is absent
<220> FEATURE:
<221> NAME/KEY: MISC_FEATURE
<222> LOCATION: (11)..(11)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
<221> NAME/KEY: MISC_FEATURE
<222> LOCATION: (12)..(12)
<223> OTHER INFORMATION: Xaa = Lys or is absent
<220> FEATURE:
<221> NAME/KEY: MISC_FEATURE
<222> LOCATION: (13)..(13)
<223> OTHER INFORMATION: Xaa = Ser, Thr, Tyr, Asn, Gln, Asp, Glu, Arg,
      His, Orn, 2,4-diaminobutanoic acid, 2,3-diaminopropanoic acid, Met
      or is absent
<220> FEATURE:
<221> NAME/KEY: MISC_FEATURE
<222> LOCATION: (14)..(14)
<223> OTHER INFORMATION: Xaa = Lys or is absent

<400> SEQUENCE: 126

Xaa Lys Xaa Lys Xaa Xaa Xaa Xaa Xaa Xaa Xaa Xaa Xaa Xaa
1               5                   10

<210> SEQ ID NO 127
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(14)
<223> OTHER INFORMATION: Xaa = Lys or is absent
<220> FEATURE:
<221> NAME/KEY: MISC_FEATURE
<222> LOCATION: (15)..(15)
<223> OTHER INFORMATION: Xaa = Ser, Thr, Tyr, Asn, Gln, Asp, Glu, Arg,
      His, or Met
<220> FEATURE:
<221> NAME/KEY: MISC_FEATURE
<222> LOCATION: (16)..(28)
<223> OTHER INFORMATION: Xaa = Ser, Thr, Tyr, Asn, Gln, Asp, Glu, Arg,
      His, Met or is absent

<400> SEQUENCE: 127

Lys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 128
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ser, Thr, Tyr, Asn, Gln, Asp, Glu, Arg,
      His, or Met.
<220> FEATURE:
<221> NAME/KEY: MISC_FEATURE
<222> LOCATION: (2)..(14)
<223> OTHER INFORMATION: Xaa = Ser, Thr, Tyr, Asn, Gln, Asp, Glu, Arg,
```

```
        His, Met or is absent
<220> FEATURE:
<221> NAME/KEY: MISC_FEATURE
<222> LOCATION: (16)..(28)
<223> OTHER INFORMATION: Xaa = Lys or is absent

<400> SEQUENCE: 128

Xaa Xaa Xaa Xaa Xaa Xaa Xaa Xaa Xaa Xaa Xaa Xaa Xaa Xaa Lys Xaa
1               5                   10                  15

Xaa Xaa Xaa Xaa Xaa Xaa Xaa Xaa Xaa Xaa Xaa Xaa
            20                  25

<210> SEQ ID NO 129
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala, Leu, Ser, Thr, Tyr, Asn, Gln, Asp,
      Glu, Arg, His, Met, Orn, 2,3-diaminopropanoic acid or
      2,4-diaminobutanoic acid
<220> FEATURE:
<221> NAME/KEY: MISC_FEATURE
<222> LOCATION: (3)..(5)
<223> OTHER INFORMATION: Xaa = Lys or is absent
<220> FEATURE:
<221> NAME/KEY: MISC_FEATURE
<222> LOCATION: (6)..(6)
<223> OTHER INFORMATION: Xaa = Ala, Leu, Ser, Thr, Tyr, Asn, Gln, Asp,
      Glu, Arg, His, Met, Orn, 2,3-diaminopropanoic acid, or
      2,4-diaminobutanoic acid.
<220> FEATURE:
<221> NAME/KEY: MISC_FEATURE
<222> LOCATION: (7)..(9)
<223> OTHER INFORMATION: Xaa = Ala, Leu, Ser, Thr, Tyr, Asn, Gln, Asp,
      Glu, Arg, His, Met, Orn, 2,3-diaminopropanoic acid,
      2,4-diaminobutanoic acid or is absent

<400> SEQUENCE: 129

Xaa Lys Xaa Xaa Xaa Xaa Xaa Xaa Xaa
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: Xaa = Ala, Leu, Ser, Thr, Tyr, Asn, Gln, Asp,
      Glu, Arg, His, Met, Orn, 2,3-diaminopropanoic acid or
      2,4-diaminobutanoic acid
<220> FEATURE:
<221> NAME/KEY: MISC_FEATURE
<222> LOCATION: (3)..(5)
<223> OTHER INFORMATION: Xaa = Ala, Leu, Ser, Thr, Tyr, Asn, Gln, Asp,
      Glu, Arg, His, Met, Orn, 2,3-diaminopropanoic acid,
      2,4-diaminobutanoic acid or is absent
<220> FEATURE:
<221> NAME/KEY: MISC_FEATURE
<222> LOCATION: (7)..(9)
<223> OTHER INFORMATION: Xaa = Lys or is absent

<400> SEQUENCE: 130

Xaa Xaa Xaa Xaa Xaa Lys Xaa Xaa Xaa
1               5

<210> SEQ ID NO 131
```

```
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = Lys or is absent
<220> FEATURE:
<221> NAME/KEY: MISC_FEATURE
<222> LOCATION: (5)..(7)
<223> OTHER INFORMATION: Xaa = Ala, Leu, Ser, Thr, Tyr, Asn, Gln, Asp,
      Glu, Arg, His, Met, Orn, 2,3-diaminopropanoic acid,
      2,4-diaminobutanoic acid or is absent
<220> FEATURE:
<221> NAME/KEY: MISC_FEATURE
<222> LOCATION: (8)..(9)
<223> OTHER INFORMATION: Xaa = Ala, Leu, Ser, Thr, Tyr, Asn, Gln, Asp,
      Glu, Arg, His, Met, Orn, 2,3-diaminopropanoic acid or
      2,4-diaminobutanoic acid

<400> SEQUENCE: 131

Lys Xaa Xaa Xaa Xaa Xaa Xaa Xaa Xaa
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ala, Leu, Ser, Thr, Tyr, Asn, Gln, Asp,
      Glu, Arg, His, Met, Orn, 2,3-diaminopropanoic acid, or
      2,4-diaminobutanoic acid
<220> FEATURE:
<221> NAME/KEY: MISC_FEATURE
<222> LOCATION: (2)..(4)
<223> OTHER INFORMATION: Xaa = Ala, Leu, Ser, Thr, Tyr, Asn, Gln, Asp,
      Glu, Arg, His, Met, Orn, 2,3-diaminopropanoic acid,
      2,4-diaminobutanoic acid or is absent
<220> FEATURE:
<221> NAME/KEY: MISC_FEATURE
<222> LOCATION: (6)..(8)
<223> OTHER INFORMATION: Xaa = Lys or is absent
<220> FEATURE:
<221> NAME/KEY: MISC_FEATURE
<222> LOCATION: (9)..(9)
<223> OTHER INFORMATION: Xaa = Ala, Leu, Ser, Thr, Tyr, Asn, Gln, Asp,
      Glu, Arg, His, Met, Orn, 2,3-diaminopropanoic acid, or
      2,4-diaminobutanoic acid

<400> SEQUENCE: 132

Xaa Xaa Xaa Xaa Lys Xaa Xaa Xaa Xaa
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = Lys or is absent
<220> FEATURE:
<221> NAME/KEY: MISC_FEATURE
<222> LOCATION: (5)..(6)
<223> OTHER INFORMATION: Xaa = Ala, Leu, Ser, Thr, Tyr, Asn, Gln, Asp,
      Glu, Arg, His, Met, Orn, 2,3-diaminopropanoic acid, or
      2,4-diaminobutanoic acid
<220> FEATURE:
```

```
<221> NAME/KEY: MISC_FEATURE
<222> LOCATION: (7)..(9)
<223> OTHER INFORMATION: Xaa = Ala, Leu, Ser, Thr, Tyr, Asn, Gln, Asp,
      Glu, Arg, His, Met, Orn, 2,3-diaminopropanoic acid,
      2,4-diaminobutanoic acid or is absent

<400> SEQUENCE: 133

Lys Xaa Xaa Xaa Xaa Xaa Xaa Xaa Xaa
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: Xaa = Ala, Leu, Ser, Thr, Tyr, Asn, Gln, Asp,
      Glu, Arg, His, Met, Orn, 2,3-diaminopropanoic acid,
      2,4-diaminobutanoic acid or is absent
<220> FEATURE:
<221> NAME/KEY: MISC_FEATURE
<222> LOCATION: (4)..(5)
<223> OTHER INFORMATION: Xaa = Ala, Leu, Ser, Thr, Tyr, Asn, Gln, Asp,
      Glu, Arg, His, Met, Orn, 2,3-diaminopropanoic acid, or
      2,4-diaminobutanoic acid
<220> FEATURE:
<221> NAME/KEY: MISC_FEATURE
<222> LOCATION: (7)..(9)
<223> OTHER INFORMATION: Xaa = Lys or is absent

<400> SEQUENCE: 134

Xaa Xaa Xaa Xaa Xaa Lys Xaa Xaa Xaa
1               5
```

PHARMACOLOGICALLY ACTIVE PEPTIDE CONJUGATES HAVING A REDUCED TENDENCY TOWARDS ENZYMATIC HYDROLYSIS

CROSS-REFERENCE TO RELATED APPLICATIONS

This application is Continuation of U.S. Utility application Ser. No. 11/007,772 filed Dec. 7, 2004 now U.S. Pat. No. 7,414,107, which is a Continuation of U.S. Utility application Ser. No. 09/341,590, filed Jul. 12, 1999 now abandoned, which claims priority under 35 U.S.C. §371 from international application PCT/DK99/00118, filed Mar. 9, 1999, which claims priority from Danish Patent Application No. 0317/98, filed Mar. 9, 1998.

BACKGROUND OF THE INVENTION

There exist a large number of pharmacologically active peptides, e.g., naturally occurring in man or in animals, or synthetic analogues of such peptides. An illustrative example of such a peptide is the analgetically active peptide enkephalin that has given rise to a vast number of synthetic analogues. However, due to precisely their peptic nature, the routes of administration thereof have been rather limited. Thus, peptides are rapidly and very effectively degraded by enzymes, generally with half-lives in the range of minutes. Proteases and other proteolytic enzymes are ubiquitous, particularly in the gastro-intestinal tract, and therefore peptides are usually susceptible to degradation in multiple sites upon oral administration, and to some extent in the blood, the liver, the kidney, and the vascular endothelia. Furthermore, a given peptide is usually susceptible to degradation at more than one linkage within the backbone; each locus of hydrolysis is mediated by a certain protease. Even if such obstacles are overcome, for neuropeptides in particular, difficulties have been encountered in their transport across the blood-brain barrier.

There have been a number of attempts to protect peptides against premature degradation (reviewed in Prokai, 1997, Exp. Opin. Ther. Patent 7:233-245, Tamai et al., 1996, Adv. Drug Delivery Rev. 19:401-424 and Zhou et al., 1991, Int. J. Pharm. 75:97-115). One approach includes osmotically altering the blood-brain barrier by infusion of hypertonic solutions of mannitol, arabinose, lactamide, saline, urea, glycerol and radiographic contrast agents. However, there could be toxic side effects.

Another approach involves the use of protease inhibitors (reviewed in Zhou et al., 1991, Int. J. Pharm. 75:97-115). This approach has yielded mixed results.

A third approach has involved the use of absorption enhancers in peptide formulations (reviewed in Zhou et al., 1991, Int. J. Pharm. 75:97-115). Examples include fatty acids and bile salts. However, varying results have been obtained regarding efficacies, and the value of a particular enhancer is dependent on the route of administration used.

Another approach for enhancing the absorption of peptides involves chemically modifying the peptide by, for example, attaching a liphophilic moiety. It has also been found that attaching a pyroglutamyl residue at the N-terminal end can render a compound relatively resistant to hydrolysis. Tamai et al., 1996, Adv. Drug Delivery Rev. 19:401-404, discloses that E2078, a dynorphin analog, was chemically modified to make it more stable to enzyme degradation by adding an N-methyl group at the amino-terminus of Arg and replacing D-Leu with L-Leu and adding ethylamine at the carboxy-terminal.

A different approach involves the formation of chimeric peptides. This approach involves coupling the peptide that is not normally transported through the blood-brain barrier to peptide or protein "vectors" that undergo receptor-mediated or adsorptive-mediated transcytosis.

WO 98/22577 discloses a method for increasing the resistance of a "core protein" to proteolytic degradation by linking or inserting a "stabilizing polypeptide" having the formula $[(Gly_a)X(Gly_b)Y(Gly_c)Z]n$. X, Y, and Z may be alanine, serine, valine, isoleucine, leucine, methionine, phenylalanine, proline, and threonine.

U.S. Pat. No. 5,545,719 discloses molecules comprising protein fragments homologous to an active region of protein fragments capable of stimulating nerve growth (neuronotrophic proteins such as epidermal growth factor, tubulin, nerve growth factor, laminin, fibronectin, NCAM and ependymin) no greater than 80 amino acids long connected to a secondary molecule which can be a second protein fragment derived from the original protein, from another protein or from a non-proteinaceous moiety. This secondary molecule facilitates the transport of the peptide across the blood-brain barrier. It is stated in column 3, lines 3-7, "Upon entering the central nervous system, prodrug can remain intact or the chemical linkage between the carrier and the protein fragment may be hydrolyzed thereby separating the carrier from the fragment to release the nerve growth-stimulating fragment." A preferred method for facilitating the coupling of the secondary molecule to the protein fragment is via one or more basic amino acids, preferably a pair of Lys residues, an Arg residue, or Arg-Lys.

Fawell et al., 1994, Proc. Natl. Acad. Sci. USA 91: 664-668 discloses chemically crosslinking various Tat peptide fragments to B-galactosidase, RNase A, and domain III of *Pseudomonas* exotoxin A. These included Tat-(37-72), Tat-(37-58) and Tat-(47-58). All of these peptides appeared to promote uptake of galactosidase, RNase A, and domain III into cells. It was stated that this is the basic region of Tat. Conjugates containing poly (L-lysine) or poly (L-arginine) were not taken up by the cells.

WO 97/24445 discloses fusion proteins of albumin and growth hormone or variants thereof. It is stated in the specification that variants of albumin should have the oncotic, ligand-binding, and non-immunogenic properties of full-length albumin and that variants of growth hormone should have its non-immunogenicity and ability to bind and activate the growth hormone receptor. Further, it is stated that the albumin variant will be at least 100 amino acids long and that the growth hormone variant should have growth hormone activity and will generally have at least 10 amino acids.

WO98/28427 discloses an Fc-OB fusion protein. Fc is an immunoglobulin fragment and OB is leptin. It has been found that such conjugates are more stable than OB alone. The Fc fragment is 378 amino acids in length. The Fc fragment can be conjugated directly or via a linker to OB or an OB fragment.

Another approach involves preparing peptide analogs with increased stability and/or activity by adding a peptide tail. Greene et al., J. Pharm. Exp. Therap. 277:1366-1375, discloses results of studies with various enkephalin analog prodrugs of [D-Pen$^2$, D-Pen$^5$] enkephalin (DPDPE) and [D-Pen$^2$, L-Cys$^5$] enkephalin (DPLCE) (SEQ ID NO: 1), specifically DPLCE-Arg-Pro-Ala (SEQ ID NO: 2), DPDPE-Phe (SEQ ID NO: 3), DPLCE-Phe (SEQ ID NO: 4), DPDPE-Arg-Gly (SEQ ID NO: 5), DPLCE-Arg-Gly (SEQ ID NO: 6), DPDPE-Phe-Ala-NH—C$_6$H$_{13}$ (SEQ ID NO: 7), DPDPE-Phe-Ala-CONH$_2$ (SEQ ID NO: 7). The half-lives of most of the analogs, except for DPDPE-Arg-Gly are less than the parent compounds. It is stated on page 1372, column 2 that "the ideal CNS-targeted prodrug would have a long half-life in the serum and a short half-life in the brain." U.S. Pat. No. 4,724,229 discloses vasopressin antagonists, which have a tripeptide side chain having three basic amino acids, such as arginine, lysine, or ornithine that have potent antagonistic activity. U.S. Pat. No. 4,542,124, discloses vasopressin antagonists, which have a dipeptide side chain having two amino acids, one of which has potent vasopressin antagonistic activity.

In the international patent application PCT/DK97/00376 (Bjarne Due Larsen and Arne Holm), prodrugs of pharmacologically active peptides are described, wherein the pharmacologically active peptide is coupled at its C terminus to a peptide pre-sequence via a linker, the linker typically being an α-hydroxy carboxylic acid. These special peptide derivatives were found to have a prolonged half-life in the presence of proteolytic enzymes such as carboxypeptidase A, leucine aminopeptidase, pepsin A and α-chymotrypsin. In addition, PCT/DK97/00376 discloses (as reference compounds) four different peptides equipped with a peptide pre-sequence but without a linker, namely DSIP-(Lys-Glu)$_3$ (SEQ ID NO: 8), DSIP-(Glu)$_6$ (SEQ ID NO: 9), Leu-enkephalin-(Glu)$_6$ (SEQ ID NO: 10), and Leu-enkephalin-(Lys)$_6$ (SEQ ID NO: 11).

It is evident that there is a need for a peptide conjugate which contains a pharmacologically active peptide and a stabilising protein that is relatively simple to synthesize, retains its activity even without removing the stabilising peptide, is stable in plasma or serum and is relatively resistant to enzyme degradation. Therefore, it is an object of the invention to provide a peptide conjugate comprising a pharmacologically active peptide and stabilising peptide that is relatively resistant to enzyme degradation.

DETAILED DESCRIPTION OF THE INVENTION

Peptide Conjugates

In the present context, the term "amino acid residue" as used in connection with X means any naturally occurring or synthetic α, β, or γ-amino acid (whether in the L-form or the D-form) as well as side-chain modified amino acids such as modified tyrosines wherein the aromatic ring is further substituted with e.g., one or more halogens, sulfono groups, nitro groups etc., and/or the phenol group is converted into an ester group, etc, including side-chain protected amino acids, wherein the amino acid side-chains are protected in accordance with methods known to the person skilled in peptide chemistry, such as described in, e.g., M. Bodanszky and A. Bodanszky, "The Practice of Peptide Synthesis," 2. Ed, Springer-Verlag, 1994, and J. Jones, "The Chemical Synthesis of Peptides," Clarendon Press, 1991.

In the present context, the term "pharmacologically active peptide sequence" or "free peptide" as applied to X is intended to mean any peptide or peptide-containing structure, either naturally occurring or synthetic which is therapeutically or prophylactically active without the stabilising sequence Z covalently bound thereto. As defined herein, a peptide sequence is "therapeutically active" if it can be used for the treatment, remission, or attenuation of a disease state, physiological condition, symptoms or etiological indication(s) or evaluation or diagnosis thereof. A peptide sequence is "prophylactically active" if it can be used to prevent a disease state, physiological condition, symptoms or etiological indications. A pharmacologically active agent is also physiologically or biologically active. Pharmacological activity measures the effect of a substance (peptide) on physiological or biological systems in vitro, in vivo, or ex vivo and may be assayed using standard in vitro, in vivo, or ex vivo assays known in the art for a particular peptide or a peptide with a similar physiological function Peptides are utilised in a number of processes, e.g., cell-to-cell communication, some being present in the autonomic and central nervous system. Some of the latter peptides, and a number of other peptides, exert important effects on vascular and other smooth muscles. In a preferred embodiment, X has at the most 75 amino acid residues (or a structure corresponding to at the most 75 amino acid residues). Alternatively, X consists of at most 65, 60, 55, 53, 50, 45, 40, 35, 30, 25, 20, 15, or at the most 10 amino acid residues and consists of at least 2, preferably 5, and more preferably 10 amino acid residues.

In the present context, the pharmacologically active peptide sequence X can be any peptide which in its native form is present as the C-terminal free carboxylic acid, such as Leu-enkephalin (H-Tyr-Gly-Gly-Phe-Leu-OH) (SEQ ID NO: 12), or is present in its native form as a C-terminal amide, such as oxytocin (Cys-Tyr-Ile-Gln-Asn-Cys-Pro-Leu-Gly-NH$_2$) (SEQ ID NO: 13), or is present in its native form as a C-terminal ester. Furthermore, the pharmacologically active peptide may also contain other special structural features such as disulfide bridges as in the case insulin.

The pharmacologically active peptide may be selected from the group consisting of enkephalin, Leu-enkephalin (SEQ ID NO: 12), Met-enkephalin, angiotensin I, angiotensin II, vasopressin, endothelin, vasoactive intestinal peptide, neurotensin, endorphins, insulin, gramicidin, paracelsin, delta-sleep inducing peptide, gonadotropin-releasing hormone (SEQ ID NO: 115), human parathyroid hormone (1-34), truncated erythropoietin analogues described in Wrighton et al., 1996, Science 273:458-463), specifically EMP-1 (SEQ ID NO: 117), Atrial natriuretic peptide (ANP, ANF), human brain natriuretic peptide (hBNP), cecropin, kinetensin, neurophysins, elafin, guamerin, atriopeptin I, atriopeptin II, atriopeptin III, deltorphin I, deltorphin II, vasotocin, bradykinin, dynorphin, dynorphin A, dynorphin B, growth hormone release factor, growth hormone, growth hormone releasing peptide, oxytocin, calcitonin, calcitonin gene-related peptide, calcitonin gene-related peptide II, growth hormone releasing peptide, tachykinin, adrenocorticotropic hormone (ACTH), brain natriuretic polypeptide, cholecystokinin, corticotropin releasing factor, diazepam binding inhibitor fragment, FMRF-amide, galanin, gastric releasing polypeptide, gastric inhibitory polypeptide, gastrin, gastrin releasing peptide, glucagon, glucagon-like peptide-1, glucagon-like peptide-2, LHRH, melanin concentrating hormone, melanocyte stimulating hormone (MSH), alpha-MSH, morphine modulating peptides, motilin, neurokinin A, neurokinin B, neuromedin B, neuromedin C, neuromedin K, neuromedin N, neuromedin U, neuropeptide K, neuropeptide Y, pituitary adenylate cyclase activating polypeptide (PACAP), pancreatic polypeptide, peptide YY, peptide histidine-methionine amide (PHM), secretin, somatostatin, substance K, thyrotropin-releasing hormone (TRH), kyotorphin, melanostatin (MIF-1), thrombopoeitin analogs, in particular AF 12505 (Ile-Glu-Gly-Pro-Thr-Leu-Arg-Gln-Trp-Leu-Ala-Ala-Arg-Ala) (SEQ ID NO: 14), insulin-like growth factor I (57-70) (Ala-Leu-Leu-Glu-Thr-Tyr-Cys-Ala-Thr-Pro-Ala-Lys-Ser-Glu) (SEQ ID NO: 15), insulin-like growth factor 1 (30-41) (Gly-Tyr-Gly-Ser-Ser-Ser-Arg-Arg-Ala-Pro-Gln-Thr) (SEQ ID NO: 16), insulin-like growth factor 1 (24-41) (Tyr-Phe-Asn-Lys-Pro-Thr-Gly-Tyr-Gly-Ser-Ser-Ser-Arg-Arg-Ala-Pro-Gln-Thr) (SEQ ID NO: 17), insulin-like growth factor II (33-40) (Ser-Arg-Val-Ser-Arg-Arg-Ser-Arg) (SEQ ID NO: 18), insulin-like growth [tyro] factor II (33-40) (Tyr-Ser-Arg-Val-Ser-Arg-Arg-Ser-Arg) (SEQ ID NO: 19), insulin-like growth factor II (69-84) (Asp-Val-Ser-Thr-Pro-Pro-Thr-Val-Leu-Pro-Asp-Asn-Phe-Pro-Arg-Tyr) (SEQ ID NO: 20), growth hormone (GH)-releasing peptide-6 (GHRP-6) (His-DTrp-Ala-Trp-DPhe-Lys-NH2) (SEQ ID NO: 21), beta-Interleukin I (163-171) (Val-Gln-Gly-Glu-Glu-Ser-Asn-Asp-Lys) (SEQ ID NO: 22), beta-Interleukin II (44-56) (Ile-Leu-Asn-Gly-Ile-Asn-Asn-Tyr-Lys-Asn-Pro-Lys-Leu) (SEQ ID NO: 23), Interleukin II (60-70) (Leu-Thr-Phe-Lys-Phe-Tyr-Met-Pro-Lys-Lys-Ala) (SEQ ID NO: 24), exendin-4 (GLP-1 analog) (His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2) (SEQ ID NO: 25), exendin-3 (GLP-1 analog) (His-Ser-Asp-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser) (SEQ ID NO: 26), [Cys(Acm)20,31] epidermal growth factor (20-31) Cys(Acm)-Met-His-Ile-Glu-Ser-Leu-Asp-Ser-Tyr-Thr-Cys(Acm) (SEQ ID NO: 27), bivalirudin (Hirulog) (D-Phe-Pro-Arg-Pro-(Gly)4-Asn-Gly-Asp-Phe-Glu-Glu-Ile-Pro-Glu-Glu-Tyr-Leu) (SEQ ID NO: 28), hirulog-1 D-Phe-Pro-Arg-Pro-(Gly)4-Asn-Gly-Asp-Phe-Glu-Glu-Ile-Pro-Glu-Tyr-Leu (SEQ ID NO: 29), C-type natriuretic peptide (1-53) (CNP) (Asp-Leu-Arg-Val-Asp-Thr-Lys-Ser-Arg-Ala-Ala-Trp-Ala-Arg-Leu-Leu-Gln-Glu-His-Pro-Asn-Ala-Arg-Lys-Tyr-Lys-Gly-Ala-Asn-Lys-Lys-Gly-Leu-Ser-Lys-Gly-Cys-Phe-Gly-Leu-Lys-Leu-Asp-Arg-Ile-Gly-Ser-Met-Ser-Gly-Leu-Gly-Cys; Disulfide bridge: Cys37-Cys53) (SEQ ID NO: 30), "Mini ANP" (Met-Cys-His-cyclohexylAla-Gly-Gly-Arg-Met-Asp-Arg-Ile-Ser-Cys-Tyr-Arg, disulfide bridge Cys2-Cys13) (SEQ ID NO: 31), Melanotan-II (also known as MT-II, alpha-MSH4-10-NH2, or Ac-Nle4-Asp5-His6-D-Phe7-Arg8-Trp9-Lys10) (SEQ ID NO: 32), thymosin alpha1 (TA1) (Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn) (SEQ ID NO: 33), ornipressin (also known as 8-ornithine-vasopressin, (POR-8), [Phe2,Ile3,Orn8]vasopressin), Cys-Phe-Ile-Gln-Asn-Cys-Pro-Orn-Gly-NH$_2$, Disulfide bridge: Cys1-Cys6) (SEQ ID NO: 34), octreotide (201-995) (DPhe-Cys-Phe-DTrp-Lys-Thr-Cys-Thr-ol; disulfide bridge: Cys2-Cys7) (SEQ ID NO: 35), eptifibatide (INTEGRILIN), calcitonin gene-related peptide (CGRP) (Ala-Cys-Asp-Thr-Ala-Thr-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH$_2$; Disulfide bridge: Cys2-Cys7) (SEQ ID NO: 36), endomorphin-1 (Tyr-Pro-Trp-Phe-NH$_2$) (SEQ ID NO: 37); endomorphin-2 Tyr-Pro-Phe-Phe-NH$_2$ (SEQ ID NO: 38), nociceptin (also known as Orphanin FQ, Phe-Gly-Gly-Phe-Thr-Gly-Ala-Arg-Lys-Ser-Ala-Arg-Lys-Leu-Ala-Asn-Gln) (SEQ ID NO: 39), angiotensinogen (1-13) (Asp-Arg-Val-Tyr-Ile-His-Pro-Phe-His-Leu-Val-Ile-His) (SEQ ID NO: 40), adrenomodullin (1-12) (Tyr-Arg-Gln-Ser-Met-Asn-Asn-Phe-Gln-Gly-Leu-Arg) (SEQ ID NO: 41), antiarrhythmic peptide (AAP) (Gly-Pro-Hyp-Gly-Ala-Gly) (SEQ ID NO: 42), Antagonist G (Arg-DTrp-(nMe)Phe-DTrp-Leu-Met-NH$_2$) (SEQ ID NO: 123), indolicidin (Ile-Leu-Pro-Trp-Lys-Trp-Pro-Trp-Trp-Pro-Trp-Arg-Arg-NH$_2$) (SEQ ID NO: 43), osteocalcin (37-49) (Gly-Phe-Gln-Glu-Ala-Tyr-Arg-Arg-Phe-Tyr-Gly-Pro-Val) (SEQ ID NO: 44), cortistatin 29 (1-13) (Glp)-Glu-Arg-Pro-Pro-Leu-Gln-Gln-Pro-Pro-His-Arg-Asp) (SEQ ID NO: 45), cortistatin 14 (Pro-Cys-Lys-Asn-Phe-Phe-Trp-Lys-Thr-Phe-Ser-Ser-Cys-Lys; Disulfide bridge: Cys2-Cys 13) (SEQ ID NO: 46), PD-145065 (Ac-D-Bhg-Leu-Asp-Ile-Ile-Trp) (SEQ ID NO: 47), PD-142893 (Ac-D-Dip-Leu-Asp-Ile-Ile-Trp) (SEQ ID NO: 48), fibrinogen binding inhibitor peptide (His-His-Leu-Gly-Gly-Ala-Lys-Gln-Ala-Gly-Asp-Val) (SEQ ID NO: 49), leptin (93-105) (Asn-Val-Ile-Gln-Ile-Ser-Asn-Asp-Leu-Glu-Asn-Leu-Arg) (SEQ ID NO: 50), GR 83074 (Boc-Arg-Ala-DTrp-Phe-DPro-Pro-Nle-NH$_2$) (SEQ ID NO: 51), Tyr-W-MIF-1 (Tyr-Pro-Trp-Gly-NH$_2$) (SEQ ID NO: 52), parathyroid hormone related peptide (107-111) (Thr-Arg-Ser-Ala-Trp) (SEQ ID NO: 53), angiotensinogen (1-14) (Asp-Arg-Val-Tyr-Ile-His-Pro-Phe-His-Leu-Val-Ile-His-Asn) (SEQ ID NO: 54), Leupeptin (Ac-Leu-Leu-Arg-CHO), and any modified or truncated analogue thereof.

It is well known that many pharmacologically active peptides also exert their desired pharmaceutical effect when present in a modified or truncated form. In the case of, for example, insulin, porcine insulin differs from human insulin by only one amino acid residue, the B30 amino acid in porcine insulin being Ala and the B30 amino acid in human insulin being Thr. Despite this difference, porcine insulin has been used as an effective diabetes drug for many years. In a similar way it has been found that the essential features for activity in the heptadecapeptide porcine gastrin I are all contained in the C-terminal tetrapeptide and that essentially all pharmaceutical effects of neurotensin are associated with the C-terminal hexapeptide. Furthermore, pharmacologically active peptides, wherein one or more amide bonds have been modified, e.g., reduced, often exhibit a similar or even enhanced pharmaceutical activity; for example the Cys$^2$ ψ[CH$_2$NH]Tyr$^3$ analogue of somatostatin was found to be an even more potent growth hormone releasing agent than somatostatin itself, and also the transition state analogue Leu$^{10}$ψ [CH(OH)CH$_2$]Val$^{11}$ of angiotensin has been found to show strong inhibitory effect against the aspartic acid protease renin. Thus, the term "modified or truncated analogue thereof" is intended to mean such peptides are modified by changing and/or deleting one or more amino acid residues in the sequence of the native peptide, including modification of the side-chain, stereochemistry, and backbone in the individual amino acid residues, such as changing one or more peptide bonds (—C(=O)—NH—) into reduced forms such as CH(OH)—N—), (—CH$_2$—N—), and other peptide bond mimetics such as (—C(=O)—N(CH$_3$)—), (—C(=O)—O), (—C(=O)—CH$_2$—), (—CH=CH—), (—PO$_2$—NH—), (SO—CH$_2$—), (SO$_2$—N—), etc.

This being said, it should be understood that the peptide sequence X in question should preferably comprise at least one peptide bond (preferably at least two peptide bonds (this naturally does not apply for a dipeptide)) susceptible to enzymatic degradation in order to fully take advantage of the present invention.

In the present context, the term "$C_{1-6}$-alkyl" used alone or as part of another group designates a straight, branched or cyclic saturated hydrocarbon group having from one to six carbon atoms, such as methyl, ethyl, n-propyl, isopropyl, n-butyl, isobutyl, sec.butyl, tert.butyl, n-pentyl, n-hexyl, cyclohexyl, etc.

In the present context, the term "$C_{2-6}$-alkenyl" designates a hydrocarbon group having from two to six carbon atoms, which may be straight, branched, or cyclic and may contain one or more double bonds, such as vinyl, allyl, 1-butenyl, 2-butenyl, isobutenyl, 1-pentenyl, 2-pentenyl, 4-pentenyl, 3-methyl-1-butenyl, 2-hexenyl, 5-hexenyl, cyclohexenyl, 2,3-dimethyl-2-butenyl etc., which may have cis and/or trans configuration.

The term "aryl" is intended to mean an aromatic, carbocyclic group such as phenyl or naphtyl.

The term "heteroaryl" includes 5- or 6-membered aromatic monocyclic heterocyclic groups containing 1-4 heteroatoms selected from nitrogen, oxygen and sulphur, such as pyrrolyl, furyl, pyrazolyl, imidazolyl, oxazolyl, isoxazolyl, thiazolyl, isothiazolyl, oxadizolyl, oxazolyl, isoxazolyl, thiazolyl, isothiazolyl, oxadiazolyl, thiadiazolyl, triazolyl, pyridyl, and aromatic bicyclic heterocyclic groups containing 1-6 heteroatoms selected from nitrogen, oxygen and sulphur, such as quinolinyl.

The term "halogen" includes fluorine, chlorine, bromine, and iodine.

The peptide sequence Z is the part of the peptide conjugate responsible for introduction and/or stabilisation of a certain secondary structure into the molecule, which will render the compound more stable towards degradation by proteases. It is believed that Z needs to include at least 4 amino acid residues in order to introduce such a stabilising structural element. On the other hand it is also believed that a sequence of more than around 20 amino acid residues will not improved the stability further. Thus, Z is typically a peptide sequence of 4-20 amino acid residues, e.g., in the range of 4-15, more preferably in the range of 4-10 in particular in the range of 4-7 amino acid residues, e.g., of 4, 5, 6 or 7 amino acid residues. When Z is conjugated to X, the half-life of said peptide conjugate when treated with carboxypeptidase A or leucine aminopeptidase in about 50 mM phosphate buffer solution at about pH 7.4 at about 37° C. or in plasma or serum is at least about 2, preferably at least about 3, such as at least about 5, more preferably at least about 7, such as at least about 9, e.g., at least about 10 more than the half-life of X when not conjugated to Z. Furthermore, when the pharmacologically active peptide X is not orally absorbed, the conjugate is orally absorbed.

Each of the amino acid residues in the peptide sequence Z are independently selected from Ala, Leu, Ser, Thr, Tyr, Asn, Gln, Asp, Glu, Lys, Arg, His, Met, Orn, and amino acids of the formula I as defined herein such as diaminobutanoic acid or diaminopropanoic acid. Preferably, the amino acid residues are selected from Ser, Thr, Tyr, Asn, Gln, Asp, Glu, Lys, Arg, His, Orn, and Met, more preferably from Glu, Lys, and Met, especially Lys. The above-mentioned amino acids may have either D- or L-configuration, but preferably the above-mentioned amino acids have an L-configuration. As the pharmacologically active peptide sequence X usually consists exclusively of L-amino acids, it must be expected, in order to preserve a possible stabilising helix structure of the entire peptide conjugate, that a peptide sequence Z consisting only or principally of L-amino acids will be advantageous compared to a peptide sequence Z consisting only or principally of D-amino acids. Furthermore, it is envisaged that a peptide sequence Z consisting only or principally of D-amino acids may exert toxicological effects due to the resistance of D-peptides and D-amino acids towards biodegradation.

Thus, illustrative examples of the peptide sequence Z are: Lys-Lys-Lys-Lys (SEQ ID NO: 55), Xaa-Lys-Lys-Lys, Lys-Xaa-Lys-Lys, Lys- Lys-Xaa-Lys, Lys-Lys-Lys-Xaa ,Xaa-Xaa-Lys-Lys, Xaa-Lys-Xaa-Lys, Xaa-Lys- Lys-Xaa, Lys-Xaa-Xaa-Lys, Lys-Xaa-Lys-Xaa, Lys-Lys-Xaa-Xaa, Xaa-Xaa-Xaa- Lys, Xaa-Xaa-Lys-Xaa, Xaa-Lys-Xaa-Xaa, Lys-Xaa-Xaa-Xaa, Xaa-Xaa-Xaa-Xaa, Lys-Lys-Lys-Lys-Lys (SEQ ID NO: 56), Xaa-Lys-Lys-Lys-Lys (SEQ ID NO: 57), Lys-Xaa-Lys-Lys-Lys (SEQ ID NO: 58), Lys-Lys-Xaa-Lys-Lys (SEQ ID NO: 59), Lys-Lys-Lys-Xaa-Lys (SEQ ID NO: 60), Lys-Lys-Lys-Lys-Xaa (SEQ ID NO: 61), Xaa-Xaa-Lys-Lys-Lys, Xaa-Lys-Xaa-Lys-Lys, Xaa-Lys-Lys-Xaa-Lys, Xaa-Lys- Lys-Lys-Xaa, Lys-Xaa-Xaa-Lys-Lys, Lys-Xaa-Lys-Xaa-Lys, Lys-Xaa-Lys-Lys- Xaa, Lys-Lys-Xaa-Xaa-Lys, Lys-Lys-Xaa-Lys-Xaa, Lys-Lys-Lys-Xaa-Xaa, Lys-Xaa-Xaa-Xaa-Xaa, Xaa-Lys-Xaa-Xaa-Xaa, Xaa-Xaa-Lys-Xaa-Xaa, Xaa-Xaa-Xaa-Lys-Xaa, Xaa-Xaa-Xaa-Xaa-Lys, Xaa-Xaa-Xaa-Xaa-Xaa, Lys-Xaa-Lys, Xaa-Xaa-Xaa-Lys-Lys, Lys-Xaa-Xaa-Xaa, Xaa-Lys- Xaa-Xaa-Xaa, Xaa-Xaa-Lys-Xaa-Xaa, Xaa-Xaa-Xaa-Lys, Xaa-Xaa-Xaa-Xaa- Lys, Xaa-Xaa-Xaa-Xaa-Xaa, Lys-Lys-Lys-Lys-Lys-Lys (SEQ ID NO: 62), Xaa-Lys-Lys-Lys-Lys-Lys (SEQ ID NO: 63), Lys-Xaa-Lys-Lys-Lys-Lys (SEQ ID NO: 64), Lys-Lys-Xaa-Lys-Lys-Lys (SEQ ID NO: 65), Lys-Lys-Lys-Xaa-Lys-Lys (SEQ ID NO: 66), Lys-Lys-Lys-Lys-Xaa-Lys (SEQ ID NO: 67), Lys-Lys-Lys-Lys- Lys-Xaa (SEQ ID NO: 68), Xaa-Xaa-Lys-Lys-Lys-Lys (SEQ ID NO: 69), Xaa- Xaa-Lys-Lys-Lys (SEQ ID NO: 70), Xaa-Lys-Lys-Xaa-Lys-Lys (SEQ ID NO: 71), Xaa-Lys-Lys-Lys-Xaa-Lys (SEQ ID NO: 72), Xaa-Lys-Lys-Lys-Lys-Xaa (SEQ ID NO: 73), Lys-Xaa-Xaa-Lys-Lys-Lys (SEQ ID NO: 74), Lys-Xaa-Lys- Xaa-Lys-Lys (SEQ ID NO: 75), Lys-Xaa-Lys-Lys-Xaa-Lys (SEQ ID NO: 76), Lys-Xaa-Lys-Lys-Lys-Xaa (SEQ ID NO: 77), Lys-Lys-Xaa-Xaa-Lys-Lys (SEQ ID NO: 78), Lys-Lys-Xaa-Lys-Xaa-Lys (SEQ ID NO: 79 ), Lys-Lys-Xaa-Lys-Lys-Xaa (SEQ ID NO: 80), Lys-Lys-Lys-Xaa-Xaa-Lys (SEQ ID NO: 81), Lys-Lys-Lys- Xaa-Lys-Xaa (SEQ ID NO: 82), Lys-Lys-Lys-Lys-Xaa-Xaa (SEQ ID NO: 83), Xaa-Xaa-Xaa-Lys-Lys-Lys, Xaa-Xaa-Lys-Xaa-Lys-Lys, Xaa-Xaa-Lys-Lys-Xaa- Lys, Xaa-Xaa-Lys-Lys-Lys-Xaa, Xaa-Lys-Xaa-Xaa-Lys-Lys, Xaa-Lys-Xaa-Lys- Xaa-Lys, Xaa-Lys-Xaa-Lys-Lys-Xaa, Xaa-Lys-Lys-Xaa-Xaa-Lys, Xaa-Lys-Lys- Xaa-Lys-Xaa, Xaa-Lys-Lys-Lys-Xaa-Xaa, Lys-Xaa-Xaa-Xaa-Lys-Lys, Lys-Xaa-Xaa-Lys-Xaa-Lys, Lys-Xaa-Xaa-Lys-Lys-Xaa, Lys-Xaa-Lys-Xaa-Xaa-Lys, Lys-Xaa-Lys-Xaa-Lys-Xaa, Lys- Xaa-Lys-Lys-Xaa-Xaa, Lys-Lys-Xaa-Xaa-Lys-Xaa, Lys-Xaa-Lys-Xaa-Xaa-Lys, Lys-Lys-Xaa-Xaa-Xaa-Lys, Lys-Lys-Xaa-Xaa-Lys-Xaa, Lys-Lys-Xaa-Xaa-Xaa-Lys, Lys-Xaa-Xaa-Xaa-Lys- Lys, Lys-Lys-Xaa-Xaa-Xaa-Xaa, Lys-Xaa-Lys-Xaa-Xaa-Xaa, Lys-Xaa-Xaa-Lys- Xaa-Xaa, Lys-Xaa-Xaa-Xaa-Lys-Xaa, Lys-Xaa-Xaa-Xaa-Xaa-Lys, Xaa-Lys-Lys- Xaa-Xaa-Xaa, Xaa-Lys-Xaa-Lys-Xaa-Xaa, Xaa-Lys-Xaa-Xaa-Lys-Xaa, Xaa-Lys- Xaa-Xaa-Xaa-Lys, Xaa-Xaa-Lys-Lys-Xaa-Xaa, Xaa-Xaa-Lys-Xaa-Lys-Xaa, Xaa-Xaa-Lys-Xaa-Xaa-Lys, Xaa- Xaa-Lys-Xaa-Xaa-Lys, Xaa-Xaa-Xaa-Lys-Lys-Xaa, Xaa-Xaa-Xaa-Lys-Xaa-Lys, Xaa-Xaa-Xaa-Xaa-Lys-Lys, Lys-Xaa-Xaa-Xaa-Xaa-Xaa, Xaa-Lys-Xaa-Xaa-Xaa-Xaa, Xaa-Xaa-Lys-Xaa-Xaa-Xaa, Xaa-Xaa-Xaa-Lys-Xaa-Xaa, Xaa-Xaa-Xaa-Xaa-Lys-Xaa, Xaa-Xaa-Xaa-Xaa-Xaa-Lys, Xaa-Xaa-Xaa-Xaa-Xaa-Xaa wherein each Xaa is independently selected from the group consisting of Ala, Leu, Ser, Thr, Tyr, Asn, Gln, Asp, Glu, Arg, His, Met, Orn, and amino acids of the formula I as defined herein, e.g., Dbu or Dpr.

The stabilising peptide sequence Z may in one embodiment, have an overall charge in the range from about 0 to +15, preferably in the range from 0 to +10, e.g., from 0 to +8, in particular from about 0 to +6, such as from about 0 to +4, e.g., from 0 to +3, at pH 7. Without being bound by any specific theory, it is envisaged that the non-negative charge at the stabilising peptide sequence Z may also to some extend facilitate transportation to and over cell membranes which possess a negative potential at the extracellular site. Thus, in order to secure a non-negative overall charge on the stabilising peptide sequence Z, the peptide sequence Z preferably comprises at least one Lys amino acid residue, more preferably at least two Lys amino acid residues, such as at least three Lys amino acid residues, e.g., at least four Lys amino acid residues, even more preferably at least five Lys amino acid residues, such as at least six Lys amino acid residues.

As indicated above, the amino acid residues of Z may of course all be different or all be identical. However, in interesting embodiments of the present invention, the amino acid residues in Z are selected from two or three different amino acids, or are identical amino acids. Examples of suitable peptide sequences, wherein the amino acid residues in Z are identical are e.g., (Lys)$_n$, wherein n is an integer in the range from 4 to 15 (SEQ ID NO: 124), preferably in the range from 4 to 10, such as in the range from 4 to 8, e.g., in the range from about 4 to 6, e.g., Lys$_4$ (SEQ ID NO: 55), Lys$_5$ (SEQ ID NO: 56), or Lys$_6$ (SEQ ID NO: 62). Examples of suitable peptide sequences, wherein the amino acid residues in Z are selected from about two different amino acids are e.g., (Lys-Xaa)$_m$ or (Xaa-Lys)$_m$, wherein m is an integer in the range from about 2 to 7 (SEQ ID NOS: 125 and 126, respectively), preferably in the range from 2 to 5, such as in the range from 2 to 4, e.g., 3, and Xaa is independently selected from the group consisting of Ser, Thr, Tyr, Asn, Gln, Asp, Glu, Arg, His, Orn, 2,4-diaminobutanoic acid, 2,3-diaminopropanoic acid and Met. More preferably such peptide sequences are e.g., (Lys-Xaa)$_3$ or (Xaa-Lys)$_3$, wherein Xaa is as defined above, such as (Lys-Glu)$_3$ (SEQ ID NO: 84) or (Glu-Lys)$_3$ (SEQ ID NO: 85). Other examples of suitable peptide sequences, wherein the amino acid residues in Z are selected from about two amino acid residues are e.g., Lys$_p$-Xaa$_q$ or Xaa$_p$-Lys$_q$, wherein p and q are integers in the range from 1 to 14 (SEQ ID NOS: 127 and 128, respectively), with the proviso that p+q is in the range from 4 to 15, preferably in the range from 4 to 10, such as in the range from 4 to 8, e.g., in the range from 4 to 6, e.g., 4, 5 or 6, and Xaa is independently selected from the group consisting of Ser, Thr, Tyr, Asn, Gln, Asp, Glu, Arg, His and Met. More preferably such peptide sequences are e.g., Lys$_3$-Xaa$_3$ or Xaa$_3$-Lys$_3$, wherein Xaa is as defined above, such as Lys$_3$-Glu$_3$ (SEQ ID NO: 86) or Glu$_3$-Lys$_3$ (SEQ ID NO: 87).

Examples of suitable peptide sequences, wherein the amino acid residues in Z are selected from three different amino acids are e.g., Xaa$^1$-(Lys)$_x$-(Xaa$^2$)$_y$ (SEQ ID NO: 129), Xaa$^1$-(Xaa$^2$)$_x$-(Lys)$_y$ (SEQ ID NO: 130), (Lys)$_x$-(Xaa$^2$)$_y$-Xaa$^1$ (SEQ ID NO: 131), (Xaa$^1$)$_x$-(Lys)$_y$-Xaa$^2$ (SEQ ID NO: 132), (Lys)$_x$-Xaa$^1$-(Xaa$^2$)$_y$ (SEQ ID NO: 133), (Xaa$^1$)$_x$-Xaa$^2$-(Lys)$_y$ (SEQ ID NO: 134), Xaa$^1$-Lys-Xaa$^2$-Lys, Xaa$^1$-Lys-Xaa$^2$-Lys-Xaa$^2$, Xaa$^1$-Lys-Xaa$^2$-Lys-Xaa$^2$-Lys, Xaa$^1$-Xaa$^2$-Lys-Xaa$^2$, Xaa$^1$-Xaa$^2$-Lys-Xaa$^2$-Lys, Xaa$^1$-Xaa$^1$-Lys-Xaa$^2$-Lys-Xaa$^2$, Lys-Xaa$^2$-Lys-Xaa$^1$, Lys-Xaa$^2$-Lys-Xaa$^2$-Xaa$^1$, Lys-Xaa$^2$-Lys-Xaa$^2$-Lys-Xaa$^1$, Xaa$^2$-Lys-Xaa$^2$-Xaa$^1$, Xaa$^2$-Lys-Xaa$^2$-Lys-Xaa$^1$, Xaa$^2$-Lys-Xaa$^1$-Lys-Xaa$^2$-Xaa$^1$, etc., wherein x and y are integers in the range from about 1 to 4 with the proviso that x+y is at the most 5, and Xaa$^1$ and Xaa$^2$ is independently selected from about the group consisting of Ala, Leu, Ser, Thr, Tyr, Asn, Gln, Asp, Glu, Arg, His, Met, Orn, 2,3-diaminopropanoic acid, 2,4-diaminobutanoic acid and amino acids of the formula I as defined herein.

With respect to the peptide sequence Z, it is envisaged that the specific amino acid residues mentioned as constituents of the peptide sequence Z, i.e. Ala, Leu, Ser, Thr, Tyr, Asn, Gln, Asp, Glu, Lys, Arg, His, Met, Orn, 2,3-diaminopropanoic acid (Dpr), 2,4-diaminobutanoic acid (Dbu) and amino acid residues of the formula I as defined herein, are amino acid residues which, due to their sterical arrangement around the α-carbon atom, and probably also due to a specific electronic configuration, have certain preferences for participating in, or even stabilising or initiating, helix-like structures. The Chou-Fasman approach (Chou, P. Y. & Fasman, G. D. *Ann. Rev. Biochem.* 47, 251-276 (1978)) is one attempt to quantify (empirically) the likelihood for a specific amino acid residue to be involved in an α-helix structure (expressed as the "Conformational parameter P$_α$"). Chou and Fasman's studies and related studies have, however, shown that amino acid residues which have a low parameter P$_α$, may be found in α-helices, but of course not as often as amino acid residues having a higher P$_α$. Thus, in the peptide sequence Z, it is considered possible to include a small proportion of amino acid residues which are not among the amino acid residues selected above as constituents of Z, and still obtain the desired effect from the peptide sequence Z, in that the selected amino acid residues are believed to compensate for any negative or neutral effect of such an alternative amino acid residue.

In a specific embodiment, Z is (Dbu)$_n$ or (Dpr)$_n$, wherein n is an integer in the range from about 4 to 15, preferably in the range from about 4 to 10, such as in the range from about 4 to 8, e.g., in the range from about 4 to 6. In a most specific embodiment, Z is Dpr$_6$.

Thus, in embodiments that are within the scope of the present invention, it may be realistic to include up to 25% of amino acid residues which are not among the amino acids preferred as constituents of Z. ("25% percent" refers to the number of amino acid residues, i.e. no alternative amino acid residues are allowed in di- and tripeptides, up to one alternative amino acid residue is allowed in tetra-, penta-, hexa-, and heptapeptides, up to two alternative amino acid residues are allowed in octapeptides, etc.). Such alternative amino acid residues may be selected from Val, Ile, Pro, Phe, Gly, Trp, as well as N-methyl amino acid residues, however, preferably not Pro, Gly and N-methyl amino acid residues. Moreover, the C-terminal of Z may be in the form of the free acid, the amide, or an ester, e.g., methyl ester, ethyl ester, benzyl ester, etc., depending on the type of solid support material and cleavage conditions used in connection with the syntheses of the peptide conjugates as will be clear to the person skilled in the art. The N-terminal may be in the form of the free amine or a lactam.

The stabilising peptide sequence Z may be bound to the C-terminal or the N-terminal of the pharmacologically active peptide sequence, X, or two peptide sequences may be bound individually to both the C- and N-terminal of X. In case the native pharmacologically active peptide X possesses a free C-terminal carboxylic acid (as in the case of Leu-enkephalin), the peptide sequence Z may be attached to either the C-terminal of the peptide X or to the N-terminal of the peptide X, or the C- and N-terminal of X may both be bound to each individual peptide sequence Z. Alternatively, Z may be bound to the nitrogen atom on the side chain of lysine, histidine or arginine or a carbonyl function on the side chain of glutamic acid or aspartic acid anywhere within the peptide sequence X. In one embodiment, Z may be attached to X within the sequence and to the N- an/or C-terminal of X. Whether the sequence should be attached to the peptide sequence X at its C-terminal, at its N-terminal, or both, or within the peptide sequence X depends on the specific peptide X and the pharmaceutical function that said peptide X exerts and can be easily determined by the person skilled in the art. In some cases, the biological or physiological activity may depend crucially on the negative charge at the C-terminal of the pharmacologically active peptide X. Accordingly, in such cases, the activities and consequently pharmacological effect of X may be obstructed by blocking the negative charge on the C-terminal of the pharmacologically active peptide X and it may therefore be advantageous to attach the peptide sequence Z to the N-terminal of the peptide X. In a similar way, in cases where the pharmacologically active peptide X is present in its native form as a C-terminal amide (such as oxytocin), it may be advantageous to attach the stabilising peptide sequence Z to the N-terminus of the peptide X if it is believed that the amide group has an important pharmacological function. Thus, it should be understood that any peptide sequences corresponding to pharmacologically active peptides X having a free C-terminal carboxyl group as well as peptides corresponding to pharmacologically active peptides X having a C-terminal amide or ester group may be used in the peptide conjugates of the invention. However, in an interesting embodiment of the invention the peptide sequence Z is attached to the C-terminal of the pharmacologically active peptide X (whether X in its native form is a free carboxylic acid, an amide or an ester).

It should be understood that the peptide conjugates of the invention might also be in the form of a salt thereof. Salts include pharmaceutically acceptable salts, such as acid addition salts and basic salts. Examples of acid addition salts are hydrochloride salts, sodium salts, calcium salts, potassium salts, etc. Examples of basic salts are salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are; e.g., those described in "Remington's Pharmaceutical Sciences" 17. Ed. Alfonso R. Gennaro (Ed.), Mark Publishing Company, Easton, Pa., U.S.A., 1985 and more recent editions, and in Encyclopedia of Pharmaceutical Technology.

In a most specific embodiment, the peptide conjugate is selected from the group consisting of

```
                                        (SEQ ID NO: 88)
H-Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser Arg-Gln-Gln-Gly-Glu-Ser-Asn-Gln-

Glu-Arg-Gly-Ala-Arg-Ala-Arg-Leu-Lys₆-NH₂

(GHRH(1-44)(Human)-Lys₆-NH₂);

(SEQ ID NO: 89)
H-Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser Arg-Gln-Gln-Gly-Glu-Ser-Asn-Gln-

Glu-Arg-Gly-Ala-Arg-Ala-Arg-Leu-Glu₆-NH₂

GHRH(1-44)(Human)-Glu₆-NH₂);

(SEQ ID NO: 90)
H-Lys₆-Ser-Val-Ser-Glu-Ile-Gln-Leu-Met-His-Asn-

Leu-Gly-Lys-His-Leu-Asn-Ser-Met-Glu-Arg-Val-Glu-

Trp-Leu-Arg-Lys-Lys-Leu-Gln-Asp-Val-His-Asn-Phe-

OH (Lys₆-PTH(1-34)(Human)-OH);

(SEQ ID NO: 91)
H-Ser-Val-Ser-Glu-Ile-Gln-Leu-Met-His-Asn-Leu-Gly-

Lys-His-Leu-Asn-Ser-Met-Glu-Arg-Val-Glu-Trp-Leu-

Arg-Lys-Lys-Leu-Gln-Asp-Val-His-Asn-Phe-Lys₆-OH (PTH(1-34)(Human)-Lys₆-OH);

(SEQ ID NO: 92)
H-His-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Lys-Gly-Arg-Lys₆-OH (GLP-1-(7-36)(Human)-Lys₆-OH);
```

```
-continued
                                        (SEQ ID NO: 93)
H-Gly-Gly-Thr-Tyr-Ser-Cys(Acm)-His-Phe-Gly-Pro- Leu-Thr-Trp-Val-Cys(Acm)-Lys-Pro-Gln-Gly-Gly-Lys₆-

OH (EMP-1-Lys₆-OH);

(SEQ ID NO: 94)
H-Lys₆-Gly-Gly-Thr-Tyr-Ser-Cys(Acm)-His-Phe-Gly-

Pro-Leu-Thr-Trp-Val-Cys(Acm)-Lys-Pro-Gln-Gly-Gly-

OH (Lys₆-EMP-1-OH);

(SEQ ID NO: 95)
H-Lys₆-Gly-Gly-Thr-Tyr-Ser-Cys(Acm)-His-Phe-Gly-

Pro-Leu-Thr-Trp-Val-Cys(Acm)-Lys-Pro-Gln-Gly-Gly-

Lys₆-OH (Lys₆-EMP-1-Lys₆-OH);

(SEQ ID NO: 96)
H-Aib-His-2-D-Nal-D-Phe-Lys-(Lys)₆-NH₂

(GHRP-(Lys)₆-NH₂);

(SEQ ID NO: 97)
H-Tyr-Gly-Gly-Phe-Leu-Lys-Lys-Glu-Glu-Glu-Lys--OH (Leu-enkephalin-Lys-Lys-Glu-Glu-Glu-Lys-OH);

(SEQ ID NO: 98)
H-Tyr-Gly-Gly-Phe-Leu-Lys-Glu-Glu-Glu-Lys--OH (Leu-enkephalin-Lys-Glu-Glu-Glu-Lys-OH);

(SEQ ID NO: 99)
H-Tyr-Gly-Gly-Phe-Leu-Lys-Glu-Glu-Glu-Lys--OH (Leu-enkephalin-(Lys-Glu)₃;

(SEQ ID NO: 100)
H-Tyr-Gly-Gly-Phe-Leu-(Dpr)₆-OH (Leu-enkephalin-(Dpr)₆-OH);

(SEQ ID NO: 101)
H-Lys₆-Tyr-Gly-Gly-Phe-Leu-OH (H-Lys₆-Leu-enkephalin);

(SEQ ID NO: 11)
H-Tyr-Gly-Gly-Phe-Leu-Lys₆-OH (H-Leu-enkephalin-Lys₆);

(SEQ ID NO: 102)
H-Lys₆-Tyr-Gly-Gly-Phe-Leu-Lys₆-OH (H-Lys₆-Leu-enkephalin-Lys₆-OH);

(SEQ ID NO: 103)
Glu-His-Trp-Ser-Tyr-Gly-Leu-Arg-Pro-Gly-(Lys)₆-OH (GnRH-Lys₆-OH);

(SEQ ID NO: 104)
Glu-His-Trp-Ser-Tyr-Gly-Leu-Arg-Pro-Gly-(Lys-

Glu)₃-OH (GnRH-(Lys-Glu)₃-OH);
and
                                        (SEQ ID NO: 105)
H-Ser-Val-Ser-Glu-Ile-Gln-Leu-Met-His-Asn-Leu-Gly- Lys-His-Leu-Asn-Ser-Met-Glu-Arg-Val-Glu-Trp-Leu- Arg-Lys-Lys-Leu-Gln-Asp-Val-His-Asn-Phe-(Lys- Glu)₃-OH (PTH 1-34 human-(Lys-Glu)₃-OH).
```

As explained above, the peptide sequence Z is the part of the peptide conjugate responsible for introducing of a certain structure into the molecule, which will render the compound more stable towards protease-catalysed degradation. Therefore, the present invention also relates to the use of a stabilising peptide sequence Z as defined above for the preparation of a pharmacologically active peptide conjugate as defined above.

As mentioned previously, the routes of administration of pharmacologically active peptides have thus far been rather limited due to the fast biodegradation by proteases such as chymotrypsin, trypsin, carboxypeptidase A, pepsin, leucine aminopeptidase, etc. Thus, the requirements to the pharmacologically active peptide conjugates suitable for the demanding purpose is that on the one hand, the peptide conjugate should, at least to some extend, be able to resist protease-catalysed hydrolysis, and one the other hand, the peptide conjugate should still, at least to some extend, be able to exert the desired pharmaceutical effect normally provided by the free peptide X.

On this basis, in vitro assays have been developed which give an assessment of the capacity of a peptide conjugate to exert the desired properties. Such assays, as well as the results thereof, are illustrated in the examples. These types of assays are excellent preliminary tests which can be easily performed by the person skilled in the art to assess the suitability of any given peptide conjugate prepared according to the principles disclosed herein.

Thus, the tendency of the pharmacologically active peptide conjugates of the invention to resist protease-catalysed hydrolysis can be measured directly by the in vitro enzyme assays shown in the examples. The tendency of the peptide conjugate to resist degradation can for example be expressed as a pseudo-first-order rate constant and/or as the half-life of said peptide conjugates, which can then be compared to the corresponding values of the free peptide X.

As will be apparent from the examples provided herein, it has been found that it is possible to obtain a remarkable increase in the half-life ($t_{1/2}$) of a pharmacologically active peptide sequence by conjugating the peptide (X) in question with a stabilising peptide sequence (Z) according to the invention.

Thus, in a preferred embodiment of the invention, the ratio between the half-life of the peptide conjugate in question in the "Hydrolysis in enzyme solution test," as defined herein, and the half-life of the corresponding free peptide (X), in the "Hydrolysis in enzyme solution test," is at least about 2, preferably at least about 3, such as at least about 5, more preferably at least about 10, especially at least about 20, such as at least about 50, e.g., at least about 100, when using carboxypeptidase A or leucine aminopeptidase.

Although the proteases carboxypeptidase A and leucine aminopeptidase have been used in the tests described herein, it is envisaged that the ability of the peptide conjugates to resist protease degradation may also be tested in identical or similar test systems using other endo- or exopeptidases, such as trypsin, or mixtures of such peptidases, e.g., artificial gastric juice.

Furthermore, the ability of the peptide conjugates of the invention to exert the desired pharmaceutical effect was tested in various in vitro and in vivo assay procedures disclosed herein. Thus, preferred peptide conjugates are such conjugates, which exert some pharmaceutical effect, preferably a similar and in some cases even an enhanced pharmaceutical effect compared to the pharmacologically active free peptide (X).

As will be understood from examples provided herein, the peptide conjugates of the invention are able to "survive" various proteolytic barriers present in the gastrointestinal environment. Thus, as demonstrated in the examples herein, it is possible to administer a pharmacologically active peptide conjugate (e.g., orally) as some fraction of the administered peptide conjugate (e.g., at least 1%, 2%, 5%, 10%, 15%, 20%, 25%, 30%, 35%, 40%, 45%, 50%, 55%, 60%, 65%, 70%, 75%, 80%, 85%, 90%, 95% or even at least 99% of the total amount peptide conjugate administered) is able to enter the blood stream. Therefore, especially interesting peptide conjugates of the invention are such compounds which when administered orally in a pharmacologically effective dose (which of course depends on the actual illness or disorder to be treated and the actual peptide or peptide conjugate selected for said treatment) is present in the blood stream in a therapeutically or prophylactically effective concentration after a period of from about 0.1 min to 24 hrs., 0.1 min to 5 hours, e.g., after a period of from about 0.5 min to 3 hours, such as from about 1 min to 2 hours, preferably after a period from about 3 min to 1 hour, such as from about 5 min to 1 hour, e.g., from about 10 min to 1 hour, 1 min.-16 hrs, 0.1 min-12 hrs. Therapeutically relevant concentrations of said peptide conjugates will, of course, depend on the actual illness or disorder to be treated, and such therapeutically relevant concentrations will be known to the person skilled in the art.

Moreover, the peptide conjugates of the invention are surprisingly stable in e.g., blood serum and plasma. Thus, preferred peptide conjugates of the invention are such compounds which have a half-life in human or mice serum or plasma (optionally containing a buffer to secure a certain pH, e.g., a pH at 7.4) at 37° C. of at least about 10 minutes, such as at least about 15 min, e.g., at least about 0.5 h, preferably at least about 1 h, such as at least about 2 h, e.g., at least about 3 h, more preferably at least about 4 h, such as at least about 5 h, e.g., at least about 6 h, in particular at least about 12 h, such as at least about 24 h, e.g., at least about 36 h. Especially preferred is where the ratio of half-life of said peptide conjugate and the half-life of the corresponding pharmacologically active peptide sequence, X, in plasma or serum is at least about 2, preferably at least about 3, such as at least about 5, more preferably at least about 7, such as at least about 9, e.g., at least about 10.

Compositions

The invention also concerns a composition comprising a pharmacologically active peptide conjugate as defined above in combination with a pharmaceutically acceptable carrier.

Such compositions may be in a form adapted to oral, subcutaneous, parenteral (intravenous, intraperitoneal), intramuscular, rectal, epidural, intratracheal, intranasal, dermal, vaginal, buccal, ocularly, direct brain or pulmonary administration, preferably in a form adapted to oral administration, and such compositions may be prepared in a manner well-known to the person skilled in the art, e.g., as generally described in "Remington's Pharmaceutical Sciences," 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker. The compositions may appear in conventional forms, for example, capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene and water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g.

A typical tablet which may be prepared by conventional tabletting techniques may contain:

(1) Core: active compound (as free compound or salt thereof) 100 mg; colloidal silicon dioxide (Aerosil) 1.5 mg; cellulose, microcryst. (Avicel) 70 mg; modified cellulose gum (Ac-Di-Sol) 7.5 mg; magnesium stearate.

(2) Coating: HPMC approx. 9 mg; *Mywacett 9-40 T approx. 0.9 mg; *acylated monoglyceride used as plasticizer for film coating.

If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a conjugate of the present invention dissolved or suspended in a liquid carrier, in particular, an aqueous carrier, for aerosol application. The carrier may contain additives such as solubilizing agents, e.g., propylene glycol, surfactants such as bile acid salts or polyoxyethylene higher alcohol ethers, absorption enhancers such as lecithin (phosphatidylcholine) or cyclodextrin, or preservatives such as parabines.

The composition may also be in a form suited for local or systemic injection or infusion and may, as such, be formulated with sterile water or an isotonic saline or glucose solution. The compositions may be sterilized by conventional sterilization techniques, which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

The invention also concerns a pharmacologically active peptide conjugate as defined above for use in therapy, and the use of a pharmacologically active peptide conjugate as defined above for the manufacture of a pharmaceutical composition for use in therapy, e.g., in the treatment of disorders in the central nervous system, in vaccine therapy, and in the treatment of HIV, cancer, diabetes, incontinence, hypertension, amnesia, Alzheimer's disease, fever, depression, sex hormone regulation, eating, schizophrenia, osteoporosis and insomnia, and as analgesics and contraceptives, and such indications known to be treated by therapy comprising administration of pharmacologically active peptides.

In specific embodiments, a conjugate comprising enkephalin and Z may be used to inhibit neurons from transmitting pain impulses, a conjugate comprising growth hormone releasing hormone or growth hormone releasing peptide and Z may be used to stimulate the release of growth hormone, for use in stimulating the release of growth hormone, a conjugate comprising EMP-1 (SEQ ID NO: 117) and Z may be used to increase hemoglobin levels a conjugate comprising parathyroid hormone and Z may be used to treat or prevent bone loss, a conjugate comprising glucagon-like peptide-1 and Z may be used in the treatment of diabetes, a conjugate comprising delta sleep inducing peptide and Z may be used for treating sleep disorders and a conjugate comprising gonadotropin releasing hormone (SEQ ID NO: 115) and Z may be used to regulate sex hormones.

As mentioned above, a major obstacle to the application of peptides as clinically useful drugs is their poor delivery characteristics since most peptides are rapidly metabolised by proteolysis at most routes of administration. Consequently, a very interesting prospect of the present invention is that it is possible to prepare pharmacologically active peptide conjugates for the treatment of mammals, such as humans, which are stabilised towards degradation by proteases and, at the same time, are able to exert a pharmaceutical effect in the environment in which the free peptide (X) will exhibit a pharmaceutical action. Accordingly, the present invention also relates to the use of a pharmacologically active peptide conjugate as defined above for the manufacture of a pharmaceutical composition for the treatment or prophylaxis of a condition or disorder, where the peptide sequence X, when not bound to Z, is able to interact with a receptor (or a receptor system) involved with the condition or disorder in question, and where the interaction between X, when not bound to Z, and the receptor (or receptor system) has a therapeutic or prophylactic effect on the condition or disorder. Thus, it should be understood that a peptide conjugate of the present invention may substitute the corresponding free peptide (X) in e.g., therapies where the free peptide X is administrated intravenous since the peptide conjugates of the invention may be administered in a more convenient way, e.g., orally, as said peptide conjugates are able to overcome proteolytic barriers prevailing in the body. In a similar way, the peptide conjugates of the invention may be used in therapies where it has not previously been possible to use the corresponding free peptide (X) as X has been readily degraded in or secreted from the body.

Preparation of Conjugates

The peptide conjugates of the invention may be prepared by methods known per se in the art. Thus, the peptide sequences X and Z may be prepared by standard peptide-preparation techniques such as solution synthesis or Merrifield-type solid phase synthesis.

In one possible synthesis strategy, the peptide conjugates of the invention may be prepared by solid phase synthesis by first constructing the peptide sequence Z using well-known standard protection, coupling and deprotection procedures, thereafter sequentially coupling the pharmacologically active sequence X on Z in a manner similar to the construction of Z, and finally cleaving off the entire peptide conjugate from the carrier. This strategy yields a peptide conjugate, wherein the stabilising peptide sequence Z is covalently bound to the pharmacologically active peptide X at the C-terminal carbonyl function of X. If the desired peptide conjugate, however, is a peptide conjugate, wherein two stabilising sequences Z are covalently and independently bound to both the C- and the N-terminal of the pharmacologically active peptide X, the above strategy is also applicable but, as will be understood by the person skilled in the art, before cleaving the off the C-terminal bound peptide conjugate from the solid support, it is necessary to sequentially couple the second stabilising peptide sequence Z to the N-terminal of X in a manner similar to the procedure described above. This strategy may also be used to attach Z to the carbonyl function on the side chain of Glu or Asp.

A possible strategy for the preparation of peptide conjugates, wherein the stabilising peptide sequence Z is covalently bound to the N-terminal nitrogen atom or covalently bound to the nitrogen atom on the side chain of Lys, Arg or His of X is analogous with the method described above, i.e. said peptide conjugates may be prepared by solid phase synthesis by first constructing the pharmacologically active peptide sequence X using well-known standard protection, coupling and deprotection procedures, thereafter sequentially coupling the stabilising peptide sequence Z on X in a manner similar to the construction of X, and finally cleaving off the entire peptide conjugate from the carrier.

Another possible strategy is to prepare one or both of the two sequences X and Z (or parts thereof) separately by solution synthesis, solid phase synthesis, recombinant techniques, or enzymatic synthesis, followed by coupling of the two sequences by well-known segment condensation procedures, either in solution or using solid phase techniques or a combination thereof. In one embodiment, X may be prepared by recombinant DNA methods and Z may be prepared by solid phase synthesis. The conjugation of X and Z may be carried out by using chemical ligation. This technique allows for the assembling of totally unprotected peptide segments in a highly specific manner (Liu et al., 1996, J. Am. Chem. Soc. 118:307-312 and Dawson et al., 1996, 226:776). The conjugation can also be performed by protease-catalysed peptide bond formation, which offers a highly specific technique to combine totally unprotected peptide segments via a peptide bond (W. Kullmann, 1987, Enzymatic Peptide Synthesis, CRC Press, Boca Raton, Fla., pp. 41-59.

Side chain derivatization of Lys, Arg, His, Trp, Ser, thr, Cys, Tyr, Asp and Glu with the stabilising peptide sequence, Z can be carried out by traditional convergent peptide synthesis using suitable orthogonal protecting schemes as known in the art, or by using the equally well known general solid phase method with suitable orthogonal removable side chain protection.

Furthermore, it is envisaged that a combination of the above-mentioned strategies may be especially applicable where a modified peptide sequence, e.g., from a pharmacologically active peptide comprising isosteric bonds such as reduced peptide bonds or N-alkylated peptide bonds, is to be coupled to a peptide sequence Z. In this case, it may be advantageous to prepare the immobilised fragment of Z by successive coupling of amino acids, and then couple a complete pharmacologically active peptide sequence X (prepared in solution or fully or partially using solid phase techniques or by means of recombinant techniques) to the fragment.

Examples of suitable solid support materials (SSM) are e.g., functionalised resins such as polystyrene, polyacrylamide, polydimethylacrylamide, polyethyleneglycol, cellulose, polyethylene, polyethyleneglycol grafted on polystyrene, latex, dynabeads, etc.

It should be understood that it may be necessary or desirable that the C-terminal amino acid of the peptide sequence Z or the C-terminal amino acid of the pharmacologically active peptide X is attached to the solid support material by means of a common linker such as 2,4-dimethoxy-4'-hydroxy-benzophenone, 4-(4-hydroxy-methyl-3-methoxyphenoxy)-butyric acid, 4-hydroxy-methylbenzoic acid, 4-hydroxymethylphenoxyacetic acid, 3-(4-hydroxymethylphenoxy)propionic acid, and p-[(R,S)-a[1-(9H-fluoren-9-yl)methoxyformamido]-2,4-dimethoxybenzyl]-phenoxy-acetic acid.

The peptide conjugates of the invention may be cleaved from the solid support material by means of an acid such as trifluoracetic acid, trifluoromethanesulfonic acid, hydrogen bromide, hydrogen chloride, hydrogen fluoride, etc. optionally in combination with one or more "scavengers" suitable for the purpose, e.g., ethanedithiol, triisopropylsilane, phenol, thioanisole, etc., or the peptide conjugate of the invention may be cleaved from the solid support by means of a base such as ammonia, hydrazine, an alkoxide, such as sodium ethoxide, an hydroxide, such as sodium hydroxide, etc.

Thus, the present invention also relates to a method for the preparation of a pharmacologically active peptide conjugate, wherein Z is covalently bound to X at the C-terminal function of X (X—Z), comprising the steps of:

(a) coupling an N-α-protected amino acid in the carboxyl activated form, or an N-α-protected dipeptide in the C-terminal activated form to an immobilised peptide sequence H-Z-SSM, thereby forming an immobilised N-α-protected peptide fragment, (b) removing the N-α-protecting group, thereby forming an immobilised peptide fragment having an unprotected N-terminal end, (c) coupling an additional N-α-protected amino acid in the carboxyl activated form, or an additional N-α-protected dipeptide in the C-terminal activated form to the N-terminal end of the immobilised peptide fragment, and repeating the removal/coupling step procedure in step (b) and (c) until the desired peptide sequence X is obtained, and then (d) cleaving off the peptide conjugate from the solid support material.

In a further aspect the present invention also relates to a method for the preparation of a pharmacologically active peptide conjugate, wherein Z is covalently bound to the N-terminal nitrogen atom of X (Z—X), comprising the steps of:

(a) coupling an N-α-protected amino acid, or an N-α-protected dipeptide to a solid support material (SSM), thereby forming an immobilised N-α-protected amino acid, or an immobilised N-α-protected dipeptide fragment, (b) removing the N-α-protecting group, thereby forming an immobilised amino acid or peptide fragment having an unprotected N-terminal end, (c) coupling an additional N-α-protected amino acid in the carboxyl activated form, or an additional N-α-protected dipeptide in the C-terminal activated form to the N-terminal end of the immobilised amino acid or peptide fragment, and repeating the removal/coupling step procedure in step (b) and (c) until the desired peptide sequence X is obtained, (d) coupling an additional N-α-protected amino acid in the carboxyl activated form, or an additional N-α-protected dipeptide in the C-terminal activated form to the N-terminal end of the immobilised peptide fragment, and repeating the removal/coupling step procedure in step (b) and (d) until the desired peptide sequence Z is obtained, and then (e) cleaving off the peptide conjugate from the solid support material.

In a still further aspect the present invention relates to a method for the preparation of a pharmacologically active peptide conjugate, wherein a first sequence (Z) is covalently bound to X at the C-terminal function of X and a second sequence (Z) is covalently bound to the N-terminal nitrogen atom of X (Z—X—Z), comprising the steps of:

(a) coupling an N-α-protected amino acid in the carboxyl activated form, or an N-α-protected dipeptide in the C-terminal activated form to an immobilised peptide sequence H-Z-SSM, thereby forming an immobilised N-α-protected peptide fragment, (b) removing the N-α-protecting group, thereby forming an immobilised peptide fragment having an unprotected N-terminal end, (c) coupling an additional N-α-protected amino acid in the carboxyl activated form, or an additional N-α-protected dipeptide in the C-terminal activated form to the N-terminal end of the immobilised peptide fragment, and repeating the removal/coupling step procedure in step (b) and (c) until the desired peptide sequence X is obtained, and then (d) coupling an additional N-α-protected amino acid in the carboxyl activated form, or an additional N-α-protected dipeptide in the C-terminal activated form to the N-terminal end of the immobilised peptide fragment, and repeating the removal/coupling step procedure in step (b) and (d) until the desired peptide sequence Z is obtained, and then (e) cleaving off the peptide conjugate from the solid support material.

The coupling, removal and cleavage steps are performed by methods known to the person skilled in the art taking into consideration the protection strategy and the selected solid phase material. In general, however, it is believed that the Boc (tertbutyloxycarbonyl) as well as the Fmoc (9-fluorenylmethyloxycarbonyl) protection strategies are applicable and that peptide bonds may be formed using the various activation procedures known to the person skilled in the art, e.g., by reacting a C-terminal activated derivative (acid halide, acid anhydride, activated ester e.g., HObt-ester, etc.) of the appropriate amino acid or peptide with the amino group of the relevant amino acid or peptide as known to a person skilled in peptide chemistry.

Furthermore, it may be necessary or desirable to include side-chain protection groups when using amino acid residues carrying functional groups, which are reactive under the prevailing conditions. The necessary protection scheme will be known to the person skilled in the art (see e.g., M. Bodanszky and A. Bodanszky, "The Practice of Peptide Synthesis," 2. Ed, Springer-Verlag, 1994, J. Jones, "The Chemical Synthesis of Peptides," Clarendon Press, 1991, and Dryland et al., 1986, J. Chem. Soc., Perkin Trans. 1:125-137).

The peptide conjugates may also be prepared by means of recombinant DNA-technology using general methods and principles known to the person skilled in the art. A nucleic acid sequence encoding the conjugate may be prepared synthetically by established standard methods, e.g., the phosphoamidite method described by S. L. Beaucage and M. H. Caruthers, Tetrahedron Letters 22, 1981, pp. 1859-1869, or the method described by Matthes et al., EMBO Journal 3, 1984, pp. 801-805. According to the phosphoamidite method, oligonucleotides are synthesized, e.g., in an automatic DNA synthesizer, purified, annealed, ligated and cloned in suitable vectors.

The techniques used to isolate or clone a nucleic acid sequence encoding the pharmacologically active peptide X are known in the art and include isolation from genomic DNA, preparation from cDNA, or a combination thereof. The cloning of the nucleic acid sequences of the present invention from such genomic DNA can be effected, e.g., by using the well-known polymerase chain reaction (PCR) or antibody screening of expression libraries to detect cloned DNA fragments with shared structural features. See, e.g., Innis et al., 1990, A Guide to Methods and Application, Academic Press, New York. Other nucleic acid amplification procedures such as ligase chain reaction (LCR), ligated activated transcription (LAT) and nucleic acid sequence-based amplification (NASBA) may be used. It can then be ligated to a nucleic acid sequence encoding Z.

The nucleic acid sequence encoding the conjugate is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

In the vector, the nucleic acid sequence encoding the conjugate of the present invention should be operably connected to a suitable promoter sequence. The promoter may be any nucleic acid sequence, which shows transcriptional activity in the host cell of choice and may be derived from genes encoding proteins either homologous or heterologous to the host cell. Examples of suitable promoters for directing the transcription of the nucleic acid sequence encoding said conjugate in mammalian cells are the SV 40 promoter (Subramani et al., Mol. Cell. Biol. 1, 1981, pp. 854-864), the MT-1 (metallothionein gene) promoter (Palmiter et al., Science 222, 1983, pp. 809-814) or the adenovirus 2 major late promoter, a Rous sarcoma virus (RSV) promoter, cytomegalovirus (CMV) promoter (Boshart et al., 1981, Cell 41:521-530) and a bovine papilloma virus promoter (BPV). A suitable promoter for use in insect cells is the polyhedrin promoter (Vasuvedan et al., FEBS Lett. 311, 1992, pp. 7-11).

Examples of suitable promoters for directing the transcription of the nucleic acid sequence encoding the conjugate, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, Proceedings of the National Academy of Sciences USA 75:3727-3731), as well as the tac promoter (DeBoer et al., 1983, Proceedings of the National Academy of Sciences USA 80:21 25). Further promoters are described in "Useful proteins from recombinant bacteria" in Scientific American, 1980, 242:74-94; and in Sambrook et al., 1989, supra.

Examples of suitable promoters for directing the transcription of the nucleic acid sequence encoding the conjugate in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral a amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8:423-488.

The nucleic acid sequence encoding said conjugate may also be operably connected to a suitable terminator, such as the human growth hormone terminator (Palmiter et al., op. cit.). Preferred terminators for filamentous fungal host cells are obtained from the genes encoding *Aspergillus oryzae* TAKA amylase, *Aspergillus niger glucoamylase, Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C(CYC1), or *Saccharomyces cerevisiae* glyceraldehyde-3-phosphate dehydrogenase. Other useful terminators for yeast host cells are described by Romanos et al., 1992, supra.

The vector may further comprise elements such as polyadenylation signals (e.g., from SV 40 or the adenovirus 5 Elb region), transcriptional enhancer sequences (e.g., the SV 40 enhancer) and translational enhancer sequences (e.g., the ones encoding adenovirus VA RNAs). Furthermore, preferred polyadenylation sequences for filamentous fungal host cells are obtained from the genes encoding *Aspergillus oryzae* TAKA amylase, *Aspergillus niger glucoamylase, Aspergillus nidulans* anthranilate synthase, and *Aspergillus niger* alpha-glucosidase. Useful polyadenylation sequences for yeast host cells are described by Guo and Sherman, 1995, Molecular Cellular Biology 15:5983-5990.

The recombinant expression vector may further comprise a DNA sequence enabling the vector to replicate in the host cell in question. Examples of such a sequence (when the host cell is a mammalian cell) are the SV 40 or polyoma origin of replication. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation to make its function temperature-sensitive in the host cell (see, e.g., Ehrlich, 1978, Proc. Natl. Acad. Sci. USA 75:1433).

The vector may also comprise a selectable marker, e.g., a gene the product of which complements a defect in the host cell, such as the gene coding for dihydrofolate reductase (DHFR) or one which confers resistance to a drug, e.g., neomycin, geneticin, ampicillin, or hygromycin. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by cotransformation, e.g., as described in WO 91/17243, where the selectable marker is on a separate vector.

The procedures used to ligate the nucleic acid sequences coding for the conjugate, the promoter, and the terminator, respectively, and to insert them into suitable vectors containing the information necessary for replication, are well known to persons skilled in the art (cf., for instance, Sambrook et al., op. cit.).

The host cell into which the expression vector is introduced may be any cell which is capable of producing the conjugate and is may be a eukaryotic cell, such as invertebrate (insect) cells or vertebrate cells, e.g., *Xenopus laevis* oocytes or mammalian cells, in particular insect and mammalian cells. Examples of suitable mammalian cell lines are the COS (e.g., ATCC CRL 1650), BHK (e.g., ATCC CRL 1632, ATCC CCL 10) or CHO (e.g., ATCC CCL 61) cell lines.

Methods for transfecting mammalian cells and expressing DNA sequences introduced in the cells are described in e.g., Kaufman and Sharp, 1982, J. Mol. Biol. 159:601-621; Southern and Berg, 1982, J. Mol. Appl. Genet. 1:327-341; Loyter et al., 1982, Proc. Natl. Acad. Sci. USA 79:422-426; Wigler et al., 1978, Cell 14:725; Corsaro and Pearson, 1981, Somatic Cell Genetics 7:603, Graham and van der Eb, 1973, Virology 52:456; Fraley et al., 1980, JBC 225:10431; Capecchi, 1980, Cell 22:479; Wiberg et al., 1983, NAR 11:7287; and Neumann et al., 1982, EMBO J. 1:841-845.

The host cell may also be a unicellular pathogen, e.g., a prokaryote, or a non-unicellular pathogen, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulars, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. The transformation of a bacterial host cell may, for instance, be effected by protoplast transformation (see, e.g., Chang and Cohen, 1979, Molecular General Genetics 168:111-115), by using competent cells (see, e.g., Young and Spizizin, 1961, Journal of Bacteriology 81:823-829, or Dubnar and Davidoff Abelson, 1971, Journal of Molecular Biology 56:209-221), by electroporation (see, e.g., Shigekawa and Dower, 1988, Biotechniques 6:742-751), or by conjugation (see, e.g., Koehler and Thorne, 1987, Journal of Bacteriology 169:5771-5278).

The host cell may be a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., *Neurospora, Eupenicillium* (=*Penicillium*), *Emericella* (=*Aspergillus*), *Eurotium* (=*Aspergillus*), and the true yeasts listed above. Examples of Basidiomycota include mushrooms, rusts, and smuts. Representative groups of Chytridiomycota include, e.g., *Allomyces, Blastocladiella, Coelomomyces,* and aquatic fungi. Representative groups of Oomycota include, e.g., Saprolegniomycetous aquatic fungi (water molds) such as *Achlya*. Examples of mitosporic fungi include *Aspergillus, Penicillium, Candida,* and *Alternaria*. Representative groups of Zygomycota include, e.g., *Rhizopus* and *Mucor*. The fungal host cell may also be a yeast cell. "Yeast" as used herein includes ascosporogenous yeast (Endomycetales), basidiosporogenous yeast, and yeast belonging to the Fungi Imperfecti (Blastomycetes). The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g., in catalogues of the American Type Culture Collection).

The conjugate produced by the cells may then be recovered from the culture medium by conventional procedures including separating the host cells from the medium by centrifugation or filtration, precipitating the proteinaceous components of the supernatant or filtrate by means of a salt, e.g., ammonium sulphate, purification by a variety of chromatographic procedures, e.g., ion exchange chromatography, affinity chromatography, or the like.

The invention is further illustrated by the following examples.

EXAMPLES

Peptide Synthesis

General Procedures

Apparatus and Synthetic Strategy

Peptides were synthesized batchwise in a polyethylene vessel equipped with a polypropylene filter for filtration using 9-fluorenylmethyloxycarbonyl (Fmoc) as the N-α-amino protecting group and suitable common protection groups for side-chain functionalities (Dryland et al., 1986, J. Chem. Soc., Perkin Trans. 1:125-137).

Solvents

Solvent DMF (N,N-dimethylformamide, Riedel de-Häen, Germany) was purified by passing it through a column packed with a strong cation exchange resin (Lewatit S 100 MB/H strong acid, Bayer AG Leverkusen, Germany) and analysed for free amines prior to use by addition of 3,4-dihydro-3-hydroxy-4-oxo-1,2,3-benzotriazine (Dhbt-OH) giving rise to a yellow colour (Dhbt-O-anion) if free amines are present. Solvent DCM (dichloromethane, analytical grade, Riedel de-Häen, Germany) was used directly without purification.

Amino Acids

Fmoc-protected amino acids were purchased from MilliGen (UK) and from PerSeptive Biosystems GmbH Hamburg, Germany in suitable side-chain protected forms. Non-protein amino acids FmocOrn(Boc)-OH, Fmoc-2-D-Nal-OH, Fmoc-D-Phe-OH, Fmoc-Aib-OH were purchased from Bachem (Switzerland) and FmocDbu(Boc)-OH, FmocDpr(Boc)-OH from Neosystem, France.

Linker (4-hydroxymethylphenoxy)acetic acid (HMPA), Novabiochem, Switzerland was coupled to the resin either as a preformed or in situ generated 1-hydroxybenzotriazole (HObt) ester by means of DIC.

Coupling Reagents

Coupling reagent diisopropylcarbodiimide (DIC) was purchased from (Riedel de-Häen, Germany) and distilled prior to use, dicyclohexylcarbodiimide (DCC) was purchased from Merck-Schuchardt, München, Germany, and purified by distillation.

Solid Supports

Peptides synthesized according to the Fmoc-strategy were synthesized on the following types of solid support using 0.05 M or higher concentrations of Fmoc-protected activated amino acid in DMF. 1) PEG-PS (polyethyleneglycol grafted on polystyrene; 2) NovaSyn TG resin, 0.29 mmol/g, Novabiochem, Switzerland); 3) TentaGel S resins 0.22-0.31 mmol/g (TentaGel-S—$NH_2$; TentaGel S-Ram, TentaGel S PHB-Lys(Boc)Fmoc, TentaGel S RAM-Lys(Boc)Fmoc; Rapp polymere, Germany).

Catalysts and Other Reagents

Diisopropylethylamine (DIEA) was purchased from Aldrich, Germany, and ethylenediamine from Fluka, piperidine and pyridine from Riedel-de Häen, Frankfurt, Germany. 4-(N,N-dimethylamino)pyridine (DMAP) was purchased from Fluka, Switzerland and used as a catalyst in coupling reactions involving symmetrical anhydrides. Ethanedithiol was purchased from Riedel-de Häen, Frankfurt, Germany. 3,4-dihydro-3-hydroxy-4-oxo-1,2,3-benzotriazine (Dhbt-OH) and 1-hydroxybenzotriazole (HObt) were obtained from Fluka, Switzerland.

Enzymes

Carboxypeptidase A (EC 3.4.17.1) type I from bovine pancreas, leucine aminopeptidase (EC 3.4.11.1) type III-CP from porcine kidney, α-chymotrypsin (EC 4.4.21.1) from bovine pancreas, and pepsin A (EC 3.4.23.1) from porcine stomach mucosa bovine pancreas were obtained from Sigma, UK.

Coupling Procedures

The first amino acid was coupled as a symmetrical anhydride in DMF generated from the appropriate N-α-protected amino acid by means of DIC or DCC. The following amino acids were coupled as preformed HObt esters made from appropriate N-α-protected amino acids and HObt by means of DIC in DMF. Acylations were checked by the ninhydrin test performed at 80° C. in order to prevent Fmoc deprotection during the test (Larsen, B. D. and Holm, A., 1994, Int. J. Peptide Protein Res. 43:1-9).

Coupling as HObt-ester

Method a. 3 eq. N-α-amino protected amino acid was dissolved in DMF together with 3 eq. HObt and 3 eq DIC. The solution was left at r.t. for 10 minutes and then added to the resin, which had been washed with a solution of 0.2% Dhbt-OH in DMF prior to the addition of the preactivated amino acid.

Method b. 3 eq. N-α-amino protected amino acid was dissolved in DMF together with 3 eq. Hobt. 3 eq. DIC were added just prior to use. The final solution was added to the resin.

Preformed Symmetrical Anhydride 6 eq. N-α-amino protected amino acid was dissolved in DCM and cooled to 0° C. DCC or DIC (3 eq.) was added and the reaction continued for 10 min. The solvent was removed in vacuo and the residue dissolved in DMF. The DMF-solution was filtered in case of using DCC and immediately added to the resin followed by 0.1 eq. of DMAP.

Estimation of the Coupling Yield of the First N-α-amino Protected Amino Acid 3-5 mg dry Fmoc-protected peptide-resin was treated with 5 ml 20% piperidine in DMF for 10 min at r.t. and the UV absorption for the dibenzofulvene-piperidine adduct was estimated at 301 nm. The yield was determined using a calculated etinction coefficient $\epsilon_{301}$ based on a Fmoc-Ala-OH standard.

Deprotection of the N-α-amino Fmoc Protecting Group

Deprotection of the Fmoc group was performed by treatment with 20% piperidine in DMF (1×5 and 1×10 min.), followed by wash with DMF until no yellow colour (Dhbt-O—) could be detected after addition of Dhbt-OH to the drained DMF.

Cleavage of Peptide from Resin with Acid

Method a. Peptides were cleaved from the resins by treatment with 95% trifluoroacetic acid (TFA, Riedel-de Häen, Frankfurt, Germany)-water v/v or with 95% TFA and 5% ethanedithiol v/v at r.t. for 2 h. The filtered resins were washed with 95% TFA-water and filtrates and washings evaporated under reduced pressure. The residue was washed with ether and freeze-dried from acetic acid-water. The crude freeze-dried product was analysed by high-performance liquid chromatography (HPLC) and identified by mass spectrometry (MS).

Method b. Peptides were cleaved from the resins by treatment with 95% trifluoroacetic acid (TFA, Riedel-de Häen, Frankfurt, Germany)-water v/v or with 95% TFA and 5% ethanedithiol v/v at r.t. for 2 h. The filtered resins were washed with 95% TFA-water and filtrates and washings were diluted by adding 10% acetic acid. The resulting mixture was extracted 3 times with ether and finally freeze-dried. The crude freeze-dried product was analysed by high-performance liquid chromatography (HPLC) and identified by mass spectrometry (MS).

Method c. Peptides were cleaved from the resins by treatment with 95% trifluoroacetic acid and 5% triisopropylsilane (Sigma) v/v at r.t. for 2 h. The filtered resins were washed with 95% TFA-water and filtrates and washings evaporated under reduced pressure. The residue was washed with ether and freeze-dried from acetic acid-water. The crude freeze-dried product was analysed by high-performance liquid chromatography (HPLC) and identified by mass spectrometry (MS).

Disulfide Bond Formation

The crude Acm protected peptide was dissolved in methanol/water 4:1 and pH adjusted to 3.33 (by adding conc. acetic acid) and the concentration of the peptide was approximately $10^{-3}$ M. 10-eq iodine dissolved in methanol (20 mg/ml) was added to the peptide solution in one portion. The reaction proceeded for 4-5 days at $-18$ to $-20°$ C. and was followed by HPLC. The reaction mixture was then diluted by adding one extra volume water, and extracted 3 times with chloroform or tetrachlormethane. The clear water solution was then freeze-dried and the product was purified by preparative HPLC as described above.

Batchwise Peptide Synthesis on PEG-PS

NovaSyn TG resin (250 mg, 0.27-0.29 mmol/g) was placed in a polyethylene vessel equipped with a polypropylene filter for filtration. The resin was swelled in DMF (5 ml), and treated with 20% piperidine in DMF to secure the presence of non-protonated amino groups on the resin. The resin was drained and washed with DMF until no yellow colour could be detected after addition of Dhbt-OH to the drained DMF. HMPA (3 eq.) was coupled as a preformed HObt-ester as described above and the coupling was continued for 24 h. The resin was drained and washed with DMF (5×5 ml, 5 min each) and the acylation checked by the ninhydrin test. The first amino acid was coupled as a preformed symmetrical anhydride as described above. The coupling yields of the first Fmoc-protected amino acids were estimated as described above. It was in all cases better than 60%. The following amino acids according to the sequence were coupled as preformed Fmoc-protected, and if necessary side-chain protected, HObt esters (3 eq.) as described above. The couplings were continued for 3 h, unless otherwise specified. The resin was drained and washed with DMF (5×5 ml, 5 min each) in order to remove excess reagent. All acylations were checked by the ninhydrin test performed at 80° C. After completion of the synthesis, the peptide-resin was washed with DMF (3×5 ml, 5 min each), DCM (3×5 ml, 1 min each) and finally diethyl ether (3×5 ml, 1 min each) and dried in vacuo over night.

Batchwise Peptide Synthesis on TentaGel S—$NH_2$

TentaGel S—$NH_2$ resin (100-500 mg, 0.22-0.31 mmol/g) was placed in a polyethylene vessel equipped with a polypropylene filter for filtration. The resin was swelled in DMF (5-10 ml), and treated with 20% piperidine in DMF to secure the presence of non-protonated amino groups on the resin. The resin was drained and washed with DMF until no yellow colour could be detected after addition of Dhbt-OH to the drained DMF. HMPA (3 eq.) was coupled as an HObt-ester generated in situ by means of DIC as described above and the coupling was continued for 24 h. The resin was drained and washed with DMF (4×5-10 ml, 2 min each) and the acylation checked by the ninhydrin test. The first amino acid was coupled as a preformed symmetrical anhydride as described above. The coupling yields of the first Fmoc-protected amino acids were estimated as described above. It was in all cases better than 60%. The following amino acids according to the sequence were coupled as Fmoc-protected HObt esters (3 eq.) generated in situ by means of DIC as described above. The couplings were continued for 3 h, unless otherwise specified. The resin was drained and washed with DMF (4×5-10 ml, 2 min each) in order to remove excess reagent. All acylations were checked by the ninhydrin test performed at 80° C. After completion of the synthesis, the peptide-resin was washed with DMF (3×5-10 ml, 5 min each), DCM (3×5-10 ml, 1 min each) and finally diethyl ether (3×5-10 ml, 1 min each) and dried in vacuo.

Batchwise Peptide Synthesis on TentaGel S-RAM

TentaGel S-RAM resin (100-1000 mg, 0.22-0.31 mmol/g) was placed in a polyethylene vessel equipped with a polypropylene filter for filtration. The resin was swelled in DMF (5-10 ml), and the Fmoc group was removed according to the procedure described above. The following amino acids according to the sequence were coupled as Fmoc-protected HObt esters (3 eq.) generated in situ by means of DIC as described above. The couplings were continued for 3 h, unless otherwise specified. The resin was drained and washed with DMF (4×5-10 ml, 2 min each) in order to remove excess reagent. All acylations were checked by the ninhydrin test performed at 80° C. After completion of the synthesis, the peptide-resin was washed with DMF (3×5-10 ml, 5 min each), DCM (3×5-10 ml, 1 min each) and finally diethyl ether (3×5-10 ml, 1 min each) and dried in vacuo.

HPLC Conditions

Isocratic HPLC analysis was preformed on a Shimadzu system consisting of an LC-6A pump, an MERCK HITACHI L-4000 UV detector operated at 215 nm and a Rheodyne 7125 injection valve with a 20 µl loop. The column used for isocratic analysis was a Spherisorb ODS-2 (100×3 mm; 5-□m particles) (MicroLab, Aarhus, Denmark). HPLC analysis using gradients was performed on a MERCK-HITACHI L-6200 Intelligent pump, an MERCK HITACHI L-4000 UV detector operated at 215 nm and a Rheodyne 7125 injection valve with a 20 µl loop, or on a Waters 600 E instrument equipped with a Waters 996 photodiode array detector. The columns used were a Rescorce™ RPC 1 ml (Waters) or a LiChroCART 125-4, LiChrospher 100 RP-18 (5 µm) (Merck). Buffer A was 0.1 vol % TFA in water and buffer B 90 vol % acetonitrile, 9.9 vol % water and 0.1 vol % TFA. The buffers were pumped through the columns at a flow rate of 1.3-1.5 ml/min using either of the following gradients for peptide analysis 1) Linear gradient from 0%-100% B (30 min) or 2) 0% B (2 min) linear gradient from 0-50% B (23 min) 50-100% B (5 min). For Preparative HPLC, purification was performed on a Waters 600 E instrument equipped with a Waters 996 photodiode array detector. The column used was a Waters Delta-Pak C-18 15 µm, 100 Å, 25×100 mm. Gradient 2) was used with a flow rate of 9 ml/min.

Mass Spectroscopy

Mass spectra were obtained on a Finnigan Mat LCQ instrument equipped with an electrospray (ESI) probe (ES-MS) and on a TofSpec E, Fisons Instrument (MALDI-TOF) using β-cyano-p-hydroxycinnamic acid as matrix.

Example 1

Peptide Synthesis of H-Tyr-Gly-Gly-Phe-Leu-$Glu_6$-OH (Leu-enkephalin-$Glu_6$-OH) (SEQ ID NO: 10) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" until finishing the peptide probe Glu$_6$ (residues 6-12 of SEQ ID NO: 10). The following amino acids forming the Leu-enkephalin sequence were coupled as preformed Fmoc-protected, if necessary side-chain protected, HObt esters (3 eq.) in DMF (5 ml) generated by means of DIC. Before each of the last five couplings, the resin was washed with a solution of Dhbt-OH (80 mg in 25 ml) in order to follow the disappearance of the yellow colour as the coupling reaction proceeded. When the yellow colour was no longer visible, the couplings were interrupted by washing the resin with DMF (5×5 ml, 5 min each). The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to method a. The crude freeze-dried product was analysed by HPLC and the purity was found to be better than 90%. The identity of the peptide was confirmed by ES-MS. Yield 76%.

Example 2

Peptide Synthesis of H-Tyr-Gly-Gly-Phe-Leu-Lys$_6$-OH (Leu-enkephalin-Lys$_6$-OH) (SEQ ID NO: 11) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" until finishing the peptide probe Lys$_6$ (SEQ ID NO: 62). The following amino acids forming the Leu-enkephalin sequence were coupled as preformed Fmoc-protected HObt esters (3 eq.) in DMF (5 ml) generated by means of DIC. Before each of the last five couplings, the resin was washed with a solution of Dhbt-OH (80 mg in 25 ml), in order to follow the disappearance of the yellow colour as the coupling reaction proceed. When the yellow colour was no longer visible, the couplings were interrupted by washing the resin with DMF (5×5 ml, 5 min each). The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method a. The crude freeze-dried product was analysed by HPLC and the purity was found to be better than 98%. The identity of the peptide was confirmed by ES-MS. Yield 84%.

Example 3

Peptide Synthesis of H-Lys$_6$-Tyr-Gly-Gly-Phe-Leu-OH(H-Lys$_6$-Leu-enkephalin) (SEQ ID NO: 101) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" and the first amino acid leucine was coupled as described under coupling procedures. The following amino acids forming the H-Lys$_6$-enkephalin sequence (SEQ ID NO: 101) were coupled as preformed Fmoc-protected HObt esters (3 eq.) in DMF (5 ml) generated by means of DIC and the couplings were continued for at least 2 hours. The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin as described above using 95% TFA and 5% water (v/v) as cleavage reagent and freeze-dried from acetic acid. The crude freeze-dried product was analysed by HPLC and found to be homogeneous without deletion and Fmoc-protected sequences. The purity was found to be better than 98% and the identity of the peptide conjugate was confirmed by ES-MS. Yield 89%.

Example 4

Peptide Synthesis of H-Lys$_6$-Tyr-Gly-Gly-Phe-Leu-Lys$_6$-OH(H-Lys$_6$-Leu-enkephalin-Lys$_6$-OH) (SEQ ID NO: 102) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" until finishing the peptide probe Lys$_6$ (SEQ ID NO: 62). The following amino acids forming the H-Lys$_6$-enkephalin sequence (SEQ ID NO: 101) were coupled as preformed Fmoc-protected HObt esters (3 eq.) in DMF (5 ml) generated by means of DIC and the couplings were continued for at least 2 hours. The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method a. The crude freeze-dried product was analysed by HPLC and the purity was found to be better than 98%. The identity of the peptide was confirmed by ES-MS. Yield 90%.

Example 5

Peptide Synthesis of H-Tyr-Gly-Gly-Phe-Leu-Lys-Lys-Glu-Glu-Glu-Lys-OH (Leu-enkephalin-Lys-Lys-Glu-Glu-Glu-Lys-OH) (SEQ ID NO: 97) on TentaGel S—PHB-Lys(Boc)Fmoc Dry TentaGel S—PHB-Lys(Boc)Fmoc resin (0.22 mmol/g, 500 mg) was placed in a polyethylene vessel equipped with a polypropylene filter for filtration and swelled for two hours in DMF (5 ml). The Fmoc group on the first lysine was removed as described above and the synthesis was continued until finishing the peptide sequence as described under "Batchwise peptide synthesis on TentaGel S—PHB-Lys(Boc)Fmoc." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried peptide was purified by preparative HPLC using the procedure described above. The purified product was found to be homogeneous and the purity was found to be better than 90%. The identity of the peptide was confirmed by ES-MS. Yield 60%.

Example 6

Peptide Synthesis of H-Tyr-Gly-Gly-Phe-Leu-Lys-Glu-Glu-Glu-Glu-Lys-OH (Leu-enkephalin-Lys-Glu-Glu-Glu-Glu-Lys-OH) (SEQ ID NO: 98) on TentaGel S—PHB-Lys(Boc)Fmoc Dry TentaGel S-PHB-Lys(Boc)Fmoc resin (0.22 mmol/g, 500 mg) was placed in a polyethylene vessel equipped with a polypropylene filter for filtration and swelled for two hours in DMF (5 ml). The Fmoc group on the first lysine was removed as described above. The synthesis was continued until finishing the peptide sequence as described under "Batchwise peptide synthesis on TentaGel S—PHB-Lys(Boc)Fmoc." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze dried from acetic acid. The crude freeze-dried peptide was purified by preparative HPLC using the procedure described above. The purified product was found to be homogeneous and the purity was found to be better than 98%. The identity of the peptide was confirmed by ES-MS. Yield 65%.

Example 7

Peptide Synthesis of H-Tyr-Gly-Gly-Phe-Leu-(Orn)$_6$-OH (Leu-enkephalin-(Orn)$_6$-OH) (SEQ ID NO: 106) on TentaGel S—NH$_2$ Dry TentaGel S—NH$_2$ resin (0.31 mmol/g, 500 mg) was placed in a polyethylene vessel equipped with a polypropylene filter for filtration and swelled for two hours in DMF (5 ml). The peptide according to the sequence was assembled as described under "Batchwise peptide synthesis on TentaGel S resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was oxidized in order to make the disulfide bond according to the procedure described above. The crude cyclized peptide was purified by preparative HPLC using the procedure described above. The purified product was found to be homogeneous and the purity was found to be better than 90%. The identity of the peptide was confirmed by ES-MS. Yield 20%.

Example 8

Peptide Synthesis of H-Tyr-Gly-Gly-Phe-Leu-(Dbu)$_6$-OH (Leu-enkephalin-(Dbu)$_6$-OH) (SEQ ID NO: 107) on TentaGel S—NH$_2$ Dry TentaGel S—NH$_2$ resin (0.31 mmol/g, 500 mg) was placed in a polyethylene vessel equipped with a polypropylene filter for filtration and swelled for two hours in DMF (5 ml). The peptide according to the sequence was assembled as described under "Batchwise peptide synthesis on TentaGel S resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was oxidized in order to make the disulfide bond according to the procedure described above. The crude cyclized peptide was purified by preparative HPLC using the procedure described above. The purified product was found to be homogeneous and the purity was found to be better than 90%. The identity of the peptide was confirmed by ES-MS. Yield 22%.

Example 9

Peptide Synthesis of H-Tyr-Gly-Gly-Phe-Leu-(Dpr)$_6$-OH (Leu-enkephalin-(Dpr)$_6$-OH) (SEQ ID NO: 108) on TentaGel S—NH$_2$ Dry TentaGel S—NH$_2$ resin (0.31 mmol/g, 500 mg) was placed in a polyethylene vessel equipped with a polypropylene filter for filtration and swelled for two hours in DMF (5 ml). The peptide according to the sequence was assembled as described under "Batchwise peptide synthesis on TentaGel S resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude peptide was purified by preparative HPLC using the procedure described above. The purified product was found to be homogeneous and the purity was found to be better than 98%. The identity of the peptide was confirmed by ES-MS. Yield 22%.

Example 10

Peptide Synthesis of H-Tyr-Gly-Gly-Phe-Leu-Lys$_{10}$-OH (Leu-enkephalin-Lys$_{10}$-OH) (SEQ ID NO: 109) on TentaGel S—PHB-Lys(Boc)Fmoc Dry TentaGel S—PHB-Lys(Boc)Fmoc resin (0.22 mmol/g, 500 mg) was placed in a polyethylene vessel equipped with a polypropylene filter for filtration and swelled for two hours in DMF (5 ml). The Fmoc group on the first lysine was removed as described above and the synthesis was continued until finishing the peptide sequence as described under "Batchwise peptide synthesis on TentaGel S—PHB-Lys(Boc)Fmoc." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze dried from acetic acid. The crude freeze-dried peptide was purified by preparative HPLC using the procedure described above. The purified product was found to be homogeneous and the purity was found to be better than 98%. The identity of the peptide was confirmed by ES-MS. Yield 7.1%.

Example 11

Peptide Synthesis of H-Trp-Ala-Gly-Gly-Asp-Ala-Ser-Gly-Glu-Glu$_6$-OH (DSIP-Glu$_6$-OH) (SEQ ID NO: 9) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" until finishing the peptide probe Glu$_6$ (residues 10-15 of SEQ ID NO: 9). The following amino acids forming the DSIP sequence (SEQ ID NO: 110) were coupled as preformed Fmoc-protected HObt esters (3 eq.) in DMF (5 ml) generated by means of DIC. Before each of the last nine couplings, the resin was washed with a solution of Dhbt-OH (80 mg in 25 ml), in order to follow the disappearance of the yellow colour as the coupling reaction proceeds. When the yellow colour was no longer visible, the couplings were interrupted by washing the resin with DMF (5×5 ml, 5 min each). The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each), and dried in vacuo.

The peptide was cleaved from the resin according to Method a. The crude freeze-dried product was analysed by HPLC and the purity was found to be better than 98%. The identity of the peptide was confirmed by ES-MS. Yield 80%.

Example 12

Peptide Synthesis of H-Trp-Ala-Gly-Gly-Asp-Ala-Ser-Gly-Glu-(Lys-Glu)$_3$-OH (DSIP-(Lys-Glu)$_3$-OH) (SEQ ID NO: 8) on NovaSyn TentaGel Dry NovaSyn TG resin (0.29 mmol/g, 250 mg) was placed in a polyethylene vessel equipped with a polypropylene filter for filtration and treated as described under "batchwise peptide synthesis on PEG-PS" until finishing the peptide probe (LysGlu)$_3$ (SEQ ID NO: 84). The following amino acids forming the DSIP sequence (SEQ ID NO: 110) were coupled as preformed Fmoc-protected HObt esters (3 eq.) in DMF (5 ml) generated by means of DIC. Before each of the last nine couplings, the resin was washed with a solution of Dhbt-OH (80 mg in 25 ml), in order to follow the disappearance of the yellow colour as the coupling reaction proceeds. When the yellow colour was no longer visible, the couplings were interrupted by washing the resin with DMF (5×5 ml, 5 min each). The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each), and dried in vacuo.

The peptide was cleaved from the resin according to Method a. The crude freeze-dried product was analysed by HPLC and the purity was found to be better than 98%. The identity of the peptide was confirmed by ES-MS. Yield 91%.

Example 13

Peptide Synthesis of H-Trp-Ala-Gly-Gly-Asp-Ala-Ser-Gly-Glu-OH (SEQ ID NO: 110) (DSIP) on NovaSyn TentaGel (Reference)

Dry NovaSyn TG resin (0.29 mmol/g, 250 mg) was placed in a polyethylene vessel equipped with a polypropylene filter for filtration and treated as described under "Batchwise peptide synthesis on PEG-PS." The first amino acid was coupled as a preformed symmetrical anhydride as described above. The coupling yields of the first Fmoc-protected amino acids were estimated as described above. The yields were in all cases better than 60%. The following amino acids forming the DSIP sequence (SEQ ID NO: 110) were coupled as preformed Fmoc-protected HObt esters (3 eq.) in DMF (5 ml) generated by means of DIC. Before each of the last eight couplings, the resin was washed with a solution of Dhbt-OH (80 mg in 25 ml), in order to follow the disappearance of the yellow colour as the coupling reaction proceeds. When the yellow colour was no longer visible, the couplings were interrupted by washing the resin with DMF (5×5 ml, 5 min each). The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each), and dried in vacuo.

The peptide was cleaved from the resin according to Method a. The crude freeze-dried product was analysed by HPLC and the purity was found to be better than 98%. The identity of the peptide was confirmed by ES-MS. Yield 78%.

Example 14

Peptide Synthesis of H-Arg-Pro-Lys-Pro-Gln-Gln-Phe-Phe-Gly-Leu-Met-Lys$_6$-OH (Substance P-Lys$_6$-OH) (SEQ ID NO: 111) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" until finishing the peptide probe Lys$_6$ (SEQ ID NO: 62). The following amino acids forming the Substance P sequence (SEQ ID NO: 112) were coupled as preformed Fmoc-protected HObt esters (3 eq.) in DMF (5 ml) generated by means of DIC and the couplings were continued for at least 2 hours. The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method a. The crude freeze-dried product was analysed by HPLC and the purity was found to be better than 98%. The identity of the peptide was confirmed by ES-MS. Yield 80%.

Example 15

Peptide Synthesis of H-Arg-Pro-Lys-Pro-Gln-Gln-Phe-Phe-Gly-Leu-Met-NH$_2$ (Substance-P—NH$_2$) (SEQ ID NO: 112) on TentaGel S-RAM Dry TentaGel S-RAM resin (0.25 mmol/g, 500 mg) was placed in a polyethylene vessel equipped with a polypropylene filter for filtration and swelled for two hours in DMF (5 ml). The Fmoc group was removed according to the procedure described above, and the peptide according to the sequence was assembled as described under "Batchwise peptide synthesis on TentaGel S-RAM resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude peptide was purified by preparative HPLC using the procedure described above. The purified product was found to be homogeneous and the purity was found to be better than 98%. The identity of the peptide was confirmed by ES-MS. Yield 12.3%.

Example 16

Peptide Synthesis of H-Arg-Pro-Lys-Pro-Gln-Gln-Phe-Phe-Gly-Leu-Met-Lys$_6$-NH$_2$ (Substance-P-Lys$_6$-NH$_2$) (SEQ ID NO: 111) on TentaGel S-RAM-Lys (Boc)Fmoc Dry TentaGel S-RAM-Lys(Boc)Fmoc resin (0.22 mmol/g, 500 mg) was placed in a polyethylene vessel equipped with a polypropylene filter for filtration and swelled for two hours in DMF (5 ml). The Fmoc group on the first lysine was removed as described above and the synthesis was continued until finishing the peptide sequence as described under "Batchwise peptide synthesis on TentaGel S-Ram-Lys(Boc)Fmoc." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was purified by preparative HPLC using the procedure described above. The purified product was found to be homogeneous and the purity was found to be better than 98%. The identity of the peptide was confirmed by ES-MS. Yield 17.2%.

Example 17

Peptide Synthesis of H-(Lys)$_6$-Arg-Pro-Lys-Pro-Gln-Gln-Phe-Phe-Gly-Leu-Met-NH$_2$ (K$_6$-Substance-P—NH$_2$) (SEQ ID NO: 113) on TentaGel S-RAM Dry TentaGel S-RAM resin (0.25 mmol/g, 500 mg) was placed in a polyethylene vessel equipped with a polypropylene filter for filtration and swelled for two hours in DMF (5 ml). The Fmoc group was removed according to the procedure described above, and the peptide according to the sequence was assembled as described under "Batchwise peptide synthesis on TentaGel S-RAM resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude peptide was purified by preparative HPLC using the procedure described above. The purified product was found to be homogeneous and the purity was found to be better than 98%. The identity of the peptide was confirmed by ES-MS. Yield 10.3%.

Example 18

Peptide Synthesis of H-Aib-His-2-D-Nal-D-Phe-Lys-(Lys)$_6$-NH$_2$ (GHRP-(Lys)$_6$-NH$_2$) (SEQ ID NO: 96) on TentaGel S-RAM-Lys(Boc)Fmoc Dry TentaGel S-RAM-Lys(Boc)Fmoc resin (0.22 mmol/g, 500 mg) was placed in a polyethylene vessel equipped with a polypropylene filter for filtration and swelled for two hours in DMF (5 ml). The Fmoc group on the first lysine was removed as described above and the synthesis was continued until finishing the peptide sequence as described under "Batchwise peptide synthesis on TentaGel S-Ram-Lys(Boc)Fmoc." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was purified by preparative HPLC using the procedure described above. The purified product was found to be homogeneous and the purity was found to be better than 90%. The identity of the peptide was confirmed by ES-MS. Yield 35%.

Example 19

Peptide Synthesis of H-Aib-His-2-D-Nal-D-Phe-Lys-NH$_2$ (GHRP—NH$_2$) on TentaGel S-RAM Dry TentaGel S-RAM resin (0.25 mmol/g, 500 mg) was placed in a polyethylene vessel equipped with a polypropylene filter for filtration and swelled for two hours in DMF (5 ml). The Fmoc group was removed according to the procedure described above, and the peptide according to the sequence was assembled as described under "Batchwise peptide synthesis on TentaGel S-RAM resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was found to be homogeneous and the purity was found to be better than 95%. The identity of the peptide was confirmed by ES-MS. Yield 21%.

Example 20

Peptide Synthesis of H-(Lys)$_6$-Aib-His-2-D-Nal-D-Phe-Lys-NH$_2$ (K$_6$-GHRP—NH$_2$) (SEQ ID NO: 114) on TentaGel S-RAM Dry TentaGel S-RAM resin (0.25 mmol/g, 500 mg) was placed in a polyethylene vessel equipped with a polypropylene filter for filtration and swelled for two hours in DMF (5 ml). The Fmoc group was removed according to the procedure described above, and the peptide according to the sequence was assembled as described under "Batchwise peptide synthesis on TentaGel S-RAM resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was found to be homogeneous and the purity was found to be better than 95%. The identity of the peptide was confirmed by ES-MS. Yield 19%.

Example 21

Peptide Synthesis of Glu-His-Trp-Ser-Tyr-Gly-Leu-Arg-Pro-Gly-Lys$_6$-OH (GnRH-Lys$_6$-OH) (SEQ ID NO: 103) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" until finishing the peptide probe Lys$_6$ (SEQ ID NO: 62). The following amino acids forming the GnRH sequence (SEQ ID NO: 115) were coupled as preformed Fmoc-protected HObt esters (3 eq.) in DMF (5 ml) generated by means of DIC and the couplings were continued for at least 2 hours. The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method c. The crude freeze-dried product was analysed by HPLC and it was found to contain the target peptide together with some impurities. The crude product was purified by preparative reverse-phase HPLC. The purity was found to be better than 98% and the identity of the peptide conjugate was confirmed by ES-MS. Yield 37%.

Example 22

Peptide Synthesis of pGlu-His-Trp-Ser-Tyr-Gly-Leu-Arg-Pro-Gly-(Lys-Glu)$_3$-OH (GnRH-(Lys-Glu)$_3$-OH) (SEQ ID NO: 104) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" until finishing the peptide probe (Lys-Glu)$_3$ (SEQ ID NO: 84). The following amino acids forming the GnRH sequence (SEQ ID NO: 115) were coupled as preformed Fmoc-protected HObt esters (3 eq.) in DMF (5 ml) generated by means of DIC and the couplings were continued for at least 2 hours. The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method c. The crude freeze-dried product was analysed by HPLC and it was found to contain the target peptide together with some impurities. The crude product was purified by preparative reverse-phase HPLC. The purity was found to be better than 98% and the identity of the peptide conjugate was confirmed by ES-MS. Yield 43%.

Example 23

Peptide Synthesis of pGlu-His-Trp-Ser-Tyr-Gly-Leu-Arg-Pro-Gly-NH$_2$ (GnRH—NH$_2$) (SEQ ID NO: 115) on TentaGel S-RAM Dry TentaGel S-RAM resin (0.25 mmol/g, 500 mg) was placed in a polyethylene vessel equipped with a polypropylene filter for filtration and swelled for two hours in DMF (5 ml). The Fmoc group was removed according to the procedure described above, and the peptide according to the sequence was assembled as described under "Batchwise peptide synthesis on TentaGel S-RAM resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was found to be homogeneous and the purity was found to be better than 95%. The identity of the peptide was confirmed by ES-MS. Yield 28%.

Example 24

Peptide Synthesis of H-(Lys)$_6$-Gln-His-Trp-Ser-Tyr-Gly-Leu-Arg-Pro-Gly-NH$_2$ (K$_6$-GnRH—NH$_2$) (SEQ ID NO: 116) on TentaGel S-RAM Dry TentaGel S-RAM resin (0.25 mmol/g, 500 mg) was placed in a polyethylene vessel equipped with a polypropylene filter for filtration and swelled for two hours in DMF (5 ml). The Fmoc group was removed according to the procedure described above, and the peptide according to the sequence was assembled as described under "Batchwise peptide synthesis on TentaGel S-RAM resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was found to be homogeneous and the purity was found to be better than 95%. The identity of the peptide was confirmed by ES-MS. Yield 20%.

Example 25

Peptide Synthesis of H-Gly-Gly-Thr-Tyr-Ser-Cys-His-Phe-Gly-Pro-Leu-Thr-Trp-Val-Cys-Lys-Pro-Gln-Gly-Gly-OH (EMP-1-OH) (SEQ ID NO: 117) on TentaGel S—NH$_2$ Dry TentaGel S—NH$_2$ resin (0.31 mmol/g, 500 mg) was placed in a polyethylene vessel equipped with a polypropylene filter for filtration and swelled for two hours in DMF (5 ml). The peptide according to the sequence was assembled as described under "Batchwise peptide synthesis on TentaGel S resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was oxidized without further purification, in order to make the disulfide bond according to the procedure described above. The crude cyclized peptide was purified by preparative HPLC using the procedure described above. The purified product was found to be homogeneous and the purity was found to be better than 98%. The identity of the peptide was confirmed by ES-MS. Yield 22%.

Example 26

Peptide Synthesis of H-Gly-Gly-Thr-Tyr-Ser-Cys-His-Phe-Gly-Pro-Leu-Thr-Trp-Val-Cys-Lys-Pro-Gln-Gly-Gly-Lys$_6$-OH (EMP-1-Lys$_6$-OH) (SEQ ID NO. 93) on TentaGel S—PHB-Lys(Boc)

Dry TentaGel S—PHB-Lys(Boc)Fmoc resin (0.22 mmol/g, 500 mg) was placed in a polyethylene vessel equipped with a polypropylene filter for filtration and swelled for two hours in DMF (5 ml). The Fmoc group on the first lysine was removed as described above and the synthesis was continued until finishing the peptide sequence as described under "Batchwise peptide synthesis on TentaGel S—PHB-Lys(Boc)Fmoc." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was oxidised without further purification in order to make the disulphide bond according to the procedure described above. The crude cyclized peptide was purified by preparative HPLC using the procedure described above. The purified product was found to be homogeneous and the purity was found to be better than 98%. The identity of the peptide was confirmed by ES-MS. Yield 27%.

Example 27

Peptide Synthesis of H-(Lys)$_6$-Gly-Gly-Thr-Tyr-Ser-Cys-His-Phe-Gly-Pro-Leu-hr-Trp-Val-Cys-Lys-Pro-Gln-Gly-Gly-OH (K$_6$-EMP-1-OH) (SEQ ID NO: 94) on TentaGel S—NH$_2$ Dry TentaGel S—NH$_2$ resin (0.31 mmol/g, 500 mg) was placed in a polyethylene vessel equipped with a polypropylene filter for filtration and swelled for two hours in DMF (5 ml). The peptide according to the sequence was assembled as described under "Batchwise peptide synthesis on TentaGel S resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was oxidized without further purification, in order to make the disulfide bond according to the procedure described above. The crude cyclized peptide was purified by preparative HPLC using the procedure described above. The purified product was found to be homogeneous and the purity was found to be better than 98%. The identity of the peptide was confirmed by ES-MS. Yield 12%.

Example 28

Peptide Synthesis of H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-OH (GLP-1-(7-36)(Human)-OH) (SEQ ID NO: 118) on TentaGel S—NH$_2$ Dry TentaGel S—NH$_2$ resin (0.31 mmol/g, 500 mg) was placed in a polyethylene vessel equipped with a polypropylene filter for filtration and swelled for two hours in DMF (5 ml). The peptide according to the sequence was assembled as described under "Batchwise peptide synthesis on TentaGel S resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried peptide was purified twice by preparative HPLC using the procedure described above. The purified product was found to be homogeneous and the purity was found to be better than 98%. The identity of the peptide was confirmed by ES-MS. Yield 8.7%.

Example 29

Peptide Synthesis of H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Lys$_6$-OH (GLP-1-(7-36)(Human)-Lys$_6$-OH) (SEQ ID NO: 92) on TentaGel S—PHB-Lys(Boc)Fmoc Dry TentaGel S—PHB-Lys(Boc)Fmoc resin (0.22 mmol/g, 500 mg) was placed in a polyethylene vessel equipped with a polypropylene filter for filtration and swelled for two hours in DMF (5 ml). The Fmoc group on the first lysine was removed as described above and the synthesis was continued until finishing the peptide sequence as described under "Batchwise peptide synthesis on TentaGel S—PHB-Lys (Boc)Fmoc." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was purified twice by preparative HPLC using the procedure described above. The purified product was found to be homogeneous and the purity was found to be better than 98%. The identity of the peptide was confirmed by ES-MS. Yield 11%.

Example 30

Peptide Synthesis of H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH (PTH(1-34)(Human)-OH) (SEQ ID NO: 119) on TentaGel S—NH$_2$ Dry TentaGel S—NH$_2$ resin (0.31 mmol/g, 500 mg) was placed in a polyethylene vessel equipped with a polypropylene filter for filtration and swelled for two hours in DMF (5 ml). The peptide according to the sequence was assembled as described under "Batchwise peptide synthesis on TentaGel S resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried peptide was purified twice by preparative HPLC using the procedure described above. The purified product was found to be homogeneous and the purity was found to be better than 98%. The identity of the peptide was confirmed by ES-MS. Yield 6.1%.

Example 31

Peptide Synthesis of H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-Lys$_6$-OH (PTH(1-34)(Human)-Lys$_6$-OH) (SEQ ID NO: 91) on TentaGel S—PHB-Lys(Boc)Fmoc Dry TentaGel S—PHB-Lys(Boc)Fmoc resin (0.22 mmol/g, 500 mg) was placed in a polyethylene vessel equipped with a polypropylene filter for filtration and swelled for two hours in DMF (5 ml). The Fmoc group on the first lysine was removed as described above. And the synthesis was continued until finishing the peptide sequence as described under "Batchwise peptide synthesis on TentaGel S—PHB-Lys (Boc)Fmoc." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was purified twice by preparative HPLC using the procedure described above. The purified product was found to be homogeneous and the purity was found to be better than 98%. The identity of the peptide was confirmed by ES-MS. Yield 5.3%.

Example 32

Peptide Synthesis of H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-(Lys-Glu)$_3$-OH (PTH 1-34 human-(Lys-Glu)$_3$-OH) (SEQ ID NO: 105) on NovaSyn TentaGel Dry NovaSyn TG resin (0.29 mmol/g, 250 mg) was placed in a polyethylene vessel equipped with a polypropylene filter for filtration and treated as described under "Batchwise peptide synthesis on PEG-PS" until finishing the peptide probe (Lys-Glu)$_3$(SEQ ID NO: 84). The following amino acids forming the PTH sequence (SEQ ID NO: 119) were coupled as preformed Fmoc-protected HObt esters (3 eq.) in DMF (5 ml) generated by means of DIC and the couplings were continued for at least 2 hours. The acylations were then checked by the ninhydrin test performed at 80° C. as earlier described. After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method c. The crude freeze-dried product was analysed by HPLC and it was found to contain the target peptide together with impurities. The crude product was purified by preparative reverse-phase HPLC. The purity was found to be better than 98% and the identity of the peptide conjugate was confirmed by ES-MS. Yield 28%.

Example 33

Peptide Synthesis of H-(Lys)$_6$-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH (Lys$_6$-PTH(1-34)(Human)-OH) (SEQ ID NO: 90) on TentaGel S—NH$_2$ Dry TentaGel S—NH$_2$ resin (0.31 mmol/g, 500 mg) was placed in a polyethylene vessel equipped with a polypropylene filter for filtration and swelled for two hours in DMF (5 ml). The peptide according to the sequence was assembled as described under "Batchwise peptide synthesis on TentaGel S resins." After completion of the synthesis, the peptide-resin was washed with DMF (3×5 ml, 1 min each), DCM (3×5 ml, 1 min each), diethyl ether (3×5 ml, 1 min each) and dried in vacuo.

The peptide was cleaved from the resin according to Method b as described above and freeze-dried from acetic acid. The crude freeze-dried product was purified twice by preparative HPLC using the procedure described above. The purified product was found to be homogeneous and the purity was found to be better than 90%. The identity of the peptide was confirmed by ES-MS. Yield 6.2%.

In Vitro Kinetic Measurements

HPLC: Gradient HPLC analysis of samples from in vitro kinetic measurements performed as described below was performed using a Hewlett Packard HP 1100 HPLC system consisting of a HP 1100 Binary Pump, a HP1100 Autosampler, a HP1100 Column Thermostat and a HP 1100 Variable Wavelength Detector. A Merck LiChroCART column (125×4 mm I.D.) and a LiChroCART precolumn (4×4 mm I.D.) packed with Lichrospher RP-18 (5 µm particles) was used. The column was kept at 25° C. or 75° C. and the column effluent was measured by UV detection at 215 nm. Separation of the peptide conjugates or the native peptides from degradation products and constituents of the reaction solutions was accomplished using gradient elution of the column with mixtures of mobile phase A (0.1 vol % TFA in water) and mobile phase B (0.085 vol % TFA in acetonitrile) at a flow rate of 1 ml/min. The following linear gradients used are shown in Table 1 below:

TABLE 1

| HPLC Gradient | Peptide/Peptide Conjugate |
|---|---|
| 25-40% B in 15 minutes | H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH (PTH(1-34)(Human)-OH) (SEQ ID NO: 119) |
| 25-40% B in 15 minutes | H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-(Lys)$_6$-OH (PTH(1-34)(Human)-(Lys)$_6$-OH) (SEQ ID NO: 91) |
| 25-40% B in 15 minutes | H-(Lys)$_6$-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH ((Lys)$_6$-PTH(1-34)(Human)-OH) (SEQ ID NO: 90) |
| 25-50% B in 15 minutes | H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-OH (GLP-1(7-36)(Human)-OH) (SEQ ID NO: 118) |
| 25-50% B in 15 minutes | H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-(Lys)$_6$-OH (GLP-1(7-36)(Human)-(Lys)$_6$-OH) (SEQ ID NO. 92) |
| 5-50% B in 15 minutes | H-Gly-Gly-Thr-Tyr-Ser-Cys-His-Phe-Gly-Pro-Leu-Thr-Trp-Val-Cys-Lys-Pro-Gln-Gly-Gly-OH (EMP-1-OH) (SEQ ID NO: 117) |
| 5-50% B in 15 minutes | H-Gly-Gly-Thr-Tyr-Ser-Cys-His-Phe-Gly-Pro-Leu-Thr-Trp-Val-Cys-Lys-Pro-Gln-Gly-Gly-(Lys)$_6$-OH (EMP-1-(Lys)$_6$-OH) (SEQ ID NO: 93) |
| 10-50% B in 15 minutes | H-(Lys)$_6$-Gly-Gly-Thr-Tyr-Ser-Cys-His-Phe-Gly-Pro-Leu-Thr-Trp-Val-Cys-Lys-Pro-Gln-Gly-Gly-OH ((Lys)$_6$-EMP-1-OH) (SEQ ID NO: 94) |
| 10-50% B in 15 minutes | H-(Lys)$_6$-Gly-Gly-Thr-Tyr-Ser-Cys-His-Phe-Gly-Pro-Leu-Thr-Trp-Val-Cys-Lys-Pro-Gln-Gly-Gly-(Lys)$_6$-OH ((Lys)$_6$-EMP-1-(Lys)$_6$-OH) (SEQ ID NO: 95) |

TABLE 1-continued

| HPLC Gradient | Peptide/Peptide Conjugate |
|---|---|
| 5-40% B in 15 minutes | H-Arg-Pro-Lys-Pro-Gln-Gln-Phe-Phe-Gly-Leu-Met-$NH_2$ (Substance P-$NH_2$) (SEQ ID NO: 112) |
| 5-40% B in 15 minutes | H-Arg-Pro-Lys-Pro-Gln-Gln-Phe-Phe-Gly-Leu-Met-$(Lys)_6$-$NH_2$ (Substance P-$(Lys)_6$-$NH_2$) (SEQ ID NO: 111) |
| 25-40% B in 15 minutes | H-$(Lys)_6$-Arg-Pro-Lys-Pro-Gln-Gln-Phe-Phe-Gly-Leu-Met-$NH_2$ (($Lys)_6$-Substance P-$NH_2$) (SEQ ID NO: 113) |
| 40-100% B in 15 minutes | H-Trp-Ala-Gly-Gly-Asp-Ala-Ser-Gly-Glu-OH (DSIP) (SEQ ID NO: 110) |
| 40-100% B in 15 minutes | H-Trp-Ala-Gly-Gly-Asp-Ala-Ser-Gly-Glu-$(Lys-Glu)_3$-OH (DSIP-$(Lys-Glu)_3$-OH) (SEQ ID NO: 8) |
| 5-30% B in 15 minutes | H-Tyr-Gly-Gly-Phe-Leu-OH (Leu-Enkephalin) (SEQ ID NO: 12) |
| 5-30% B in 15 minutes | H-Tyr-Gly-Gly-Phe-Leu-$(Lys)_6$-OH (Leu-Enkephalin-$(Lys)_6$-OH) (SEQ ID NO: 11) |
| 10-35% B in 15 minutes | H-$(Lys)_6$-Tyr-Gly-Gly-Phe-Leu-OH (($Lys)_6$-Leu-Enkephalin-OH) (SEQ ID NO: 101) |
| 10-35% B in 15 minutes | H-$(Lys)_6$-Tyr-Gly-Gly-Phe-Leu-$(Lys)_6$-OH (($Lys)_6$-Leu-Enkephalin-$(Lys)_6$-OH) (SEQ ID NO: 102) |
| 5-30% B in 15 minutes | H-Tyr-Gly-Gly-Phe-Leu-$(Lys)_{10}$-OH (Leu-Enkephalin-$(Lys)_{10}$-OH) (SEQ ID NO: 109) |
| 5-30% B in 15 minutes | H-Tyr-Gly-Gly-Phe-Leu-$(Orn)_6$-OH (Leu-Enkephalin-$(Orn)_6$-OH) (SEQ ID NO: 106) |
| 5-30% B in 15 minutes | H-Tyr-Gly-Gly-Phe-Leu-$(Dbu)_6$-OH (Leu-Enkephalin-$(Dbu)_6$-OH) (SEQ ID NO: 107) |
| 5-30% B in 15 minutes | H-Tyr-Gly-Gly-Phe-Leu-$(Dpr)_6$-OH (Leu-Enkephalin-$(Dpr)_6$-OH) (SEQ ID NO: 108) |
| 5-30% B in 15 minutes | H-Tyr-Gly-Gly-Phe-Leu-Lys($Glu)_4$-Lys-OH (Leu-Enkephalin-Lys-$(Glu)_4$-Lys-OH) (SEQ ID NO: 98) |
| 5-30% B in 15 minutes | H-Tyr-Gly-Gly-Phe-Leu-Lys-$(Glu)_3$-$(Lys)_2$-OH (Leu-Enkephalin-Lys-$(Glu)_3$-$(Lys)_2$-OH) (SEQ ID NO: 120) |

Hydrolysis Kinetics in Enzyme Solution

The degradation of the peptide conjugate and the corresponding native peptide were studied at 37° C. in a 50 mM phosphate buffer solution at pH 7.4 containing leucine aminopeptidase (25 U/ml) or carboxypeptidase A (1 or 25 U/ml). Experiments were initiated by addition of an aliquot (100 µl) of a stock solution (1 mg/ml) of the peptide conjugate or the native peptide to 900 µl preheated enzyme solution giving a final concentration of ~0.1 mg/ml ($10^{-5}$-$10^{-4}$ M) of the peptide conjugate or the native peptide. The peptide/enzyme solution was kept at 37° C. using a SHT200D block heater from Stuart Scientific. At appropriate time intervals, samples of 100 µl were withdrawn from the peptide/enzyme solution, mixed thoroughly with 20 µl 25% TFA in acetonitrile in order to stop the enzymatic degradation process and analysed by HPLC as described above. Half-lives ($t_{1/2}$) for the peptide conjugate and the corresponding native peptide in the enzyme solutions were calculated from plots of the natural logarithm to the concentration of the residual peptide (HPLC peak heights) against time using the formula $t_{1/2} = 1/k_{obs} \times \ln(2)$, where $k_{obs}$ is the apparent first-order rate constant for the observed degradation.

H-Ser-Val-Ser-Glu-Ile-Gln-Leu-Met-His-Asn-Leu-Gly-Lys-His-Leu-Asn-Ser- Met-Glu-Arg-Val-Glu-Trp-Leu-Arg-Lys-Lys-Leu-Gln-Asp-Val-His-Asn-Phe- OH (PTH(1-34)(Human)-OH) (SEQ ID NO: 119)

Hydrolysis Kinetics in Leucine Aminopeptidase

The degradation of H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH (SEQ ID NO: 119) (~2.4×$10^{-5}$ M) in 50 mM phosphate buffer solutions of pH 7.4 containing leucine aminopeptidase (25 U/ml) was studied as described above. The pseudo first-order rate constant for the degradation was estimated to 2.1× $10^{-3}$ $min^{-1}$ and the corresponding half-life calculated to 330 min as previously described.

Hydrolysis Kinetics in Carboxypeptidase A

The degradation of H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH (SEQ ID NO: 119) (~2.4×$10^{-5}$ M) in 50 mM phosphate buffer solutions of pH 7.4 containing carboxypeptidase A (1 U/ml) was studied as described above. The pseudo first-order rate constant for the degradation was estimated to 5.2 $min^{-1}$ and the corresponding half-life calculated to 0.13 min as previously described.

H-Ser-Val-Ser-Glu-Ile-Gln-Leu-Met-His-Asn-Leu-Gly-Lys-His-Leu-Asn-Ser- Met-Glu-Arg-Val-Glu-Trp-Leu-Arg-Lys-Lys-Leu-Gln-Asp-Val-His-Asn-Phe- $(Lys)_6$-OH (PTH (1-34)(Human)-$(Lys)_6$-OH) (SEQ ID NO: 91)

Hydrolysis Kinetics in Leucine Aminopeptidase

The degradation of H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-(Lys)$_6$-OH (SEQ ID NO: 91) (~2.0×10$^{-5}$ M) in 50 mM phosphate buffer solutions of pH 7.4 containing leucine aminopeptidase (25 U/ml) was studied as described above. The pseudo first-order rate constant for the degradation was estimated to 1.2×10$^{-3}$ min$^{-1}$ and the corresponding half-life calculated to 578 min as previously described.

Hydrolysis Kinetics in Carboxypeptidase A

The degradation of H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-(Lys)$_6$-OH (SEQ ID NO: 91) (~2.0×10$^{-5}$ M) in 50 mM phosphate buffer solutions of pH 7.4 containing carboxypeptidase A (1 U/ml) was studied as described above. The pseudo first-order rate constant for the degradation was estimated to 1.5×10$^{-2}$ min$^{-1}$ and the corresponding half-life calculated to 47 min as previously described.

H-(Lys)$_6$-Ser-Val-Ser-Glu-Ile-Gln-Leu-Met-His-Asn-Leu-Gly-Lys-His-Leu- Asn-Ser-Met-Glu-Arg-Val-Glu-Trp-Leu-Arg-Lys-Lys-Leu-Gln-Asp-Val-His- Asn-Phe-OH ((Lys)$_6$-PTH(1-34)(Human)-OH) (SEQ ID NO: 90)

Hydrolysis Kinetics in Leucine Aminopeptidase

The degradation of H-(Lys)$_6$-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-OH (SEQ ID NO: 90) (~2.0×10$^{-5}$ M) in 50 mM phosphate buffer solutions of pH 7.4 containing leucine aminopeptidase (25 U/ml) was studied as described above. The pseudo first-order rate constant for the degradation was estimated to 3.5×10$^{-3}$ min$^{-1}$ and the corresponding half-life calculated to 198 min as previously described.

H-His-Ala-Glu-Gly-Thr-Phe-Thr-Ser-Asp-Val-Ser-Ser-Tyr-Leu-Glu-Gly- Gln-Ala-Ala-Lys-Glu-Phe-Ile-Ala-Trp-Leu-Val-Lys-Gly-Arg-OH (GLP-1(7-36)(Human)-OH) (SEQ ID NO: 118)

Hydrolysis Kinetics in Leucine Aminopeptidase

The degradation of H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-OH (SEQ ID NO: 118) (~3.0×10$^{-5}$ M) in 50 mM phosphate buffer solutions of pH 7.4 containing leucine aminopeptidase (25 U/ml) was studied as described above. The pseudo first-order rate constant for the degradation was estimated to 3.1×10$^{-2}$ min$^{-1}$ and the corresponding half-life calculated to 22 min as previously described.

Hydrolysis Kinetics in Carboxypeptidase A

The degradation of H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-OH (SEQ ID NO: 118) (~3.0×10$^{-5}$ M) in 50 mM phosphate buffer solutions of pH 7.4 containing carboxypeptidase A (1 U/ml) was studied as described above. The pseudo first-order rate constant for the degradation was estimated to 4.7×10$^{-3}$ min$^{-1}$ and the corresponding half-life calculated to 148 min as previously described.

H-His-Ala-Glu-Gly-Thr-Phe-Thr-Ser-Asp-Val-Ser-Ser-Tyr-Leu-Glu-Gly- Gln-Ala-Ala-Lys-Glu-Phe-Ile-Ala-Trp-Leu-Val-Lys-Gly-Arg-(Lys)$_6$-OH (GLP-1(7-36)(Human)-(Lys)$_6$-OH) (SEQ ID NO: 92)

Hydrolysis Kinetics in Leucine Aminopeptidase

The degradation of H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-(Lys)$_6$-OH (SEQ ID NO: 92) (~2.5×10$^{-5}$ M) in 50 mM phosphate buffer solutions of pH 7.4 containing leucine aminopeptidase (25 U/ml) was studied as described above. The pseudo first-order rate constant for the degradation was estimated to 1.3×10$^{-2}$ min$^{-1}$ and the corresponding half-life calculated to 53 min as previously described.

Hydrolysis Kinetics in Carboxypeptidase A

The degradation of H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-(Lys)$_6$-OH (SEQ ID NO: 92) (~2.5×10$^{-5}$ M) in 50 mM phosphate buffer solutions of pH 7.4 containing carboxypeptidase A (1 U/ml) was studied as described above. The pseudo first-order rate constant for the degradation was estimated to 8×10$^{-3}$ min$^{-1}$ and the corresponding half-life calculated to 87 as previously described.

H-Gly-Gly-Thr-Tyr-Ser-Cys-His-Phe-Gly-Pro-Leu-Thr-Trp-Val-Cys-Lys- Pro-Gln-Gly-Gly-OH (EMP-1-OH) (SEQ ID NO: 117)

Hydrolysis Kinetics in Leucine Aminopeptidase

The degradation of H-Gly-Gly-Thr-Tyr-Ser-Cys-His-Phe-Gly-Pro-Leu-Thr-Trp-Val-Cys-Lys-Pro-Gln-Gly-Gly-OH (SEQ ID NO: 117) (~4.8×10$^{-5}$ M) in 50 mM phosphate buffer solutions of pH 7.4 containing leucine aminopeptidase (25 U/ml) was studied as described above. The pseudo first-order rate constant for the degradation was estimated to 1.5×10$^{-3}$ min$^{-1}$ and the corresponding half-life calculated to 462 min as previously described.

Hydrolysis Kinetics in Carboxypeptidase A

The degradation of H-Gly-Gly-Thr-Tyr-Ser-Cys-His-Phe-Gly-Pro-Leu-Thr-Trp-Val-Cys-Lys-Pro-Gln-Gly-Gly-OH (SEQ ID NO: 117) (~4.8×10$^{-5}$ M) in 50 mM phosphate buffer solutions of pH 7.4 containing carboxypeptidase A (1 U/ml) was studied as described above. A half-life of more than 50 hours was estimated for the degradation.

H-Gly-Gly-Thr-Tyr-Ser-Cys-His-Phe-Gly-Pro-Leu-Thr-Trp-Val-Cys-Lys- Pro-Gln-Gly-Gly-(Lys)$_6$-OH (EMP-1-OH) (SEQ ID NO: 93)

Hydrolysis Kinetics in Leucine Aminopeptidase

The degradation of H-Gly-Gly-Thr-Tyr-Ser-Cys-His-Phe-Gly-Pro-Leu-Thr-Trp-Val-Cys-Lys-Pro-Gln-Gly-Gly-(Lys)$_6$-OH (SEQ ID NO: 93) (~3.5×10$^{-5}$ M) in 50 mM phosphate buffer solutions of pH 7.4 containing leucine aminopeptidase (25 U/ml) was studied as described above. A half-life of more than 100 hours was estimated for the degradation.

Hydrolysis Kinetics in Carboxypeptidase A

The degradation of H-Gly-Gly-Thr-Tyr-Ser-Cys-His-Phe-Gly-Pro-Leu-Thr-Trp-Val-Cys-Lys-Pro-Gln-Gly-Gly-(Lys)$_6$-OH (SEQ ID NO: 93) (~3.5×10$^{-5}$ M) in 50 mM phosphate buffer solutions of pH 7.4 containing carboxypeptidase A (1 U/ml) was studied as described above. A half-life of more than 20 hours was estimated for the degradation.

H-(Lys)$_6$-Gly-Gly-Thr-Tyr-Ser-Cys-His-Phe-Gly-Pro-Leu-Thr-Trp-Val-Cys- Lys-Pro-Gln-Gly-Gly-OH ((Lys)$_6$-EMP-1-OH) (SEQ ID NO: 94)

Hydrolysis Kinetics in Leucine Aminopeptidase

The degradation of H-(Lys)$_6$-Gly-Gly-Thr-Tyr-Ser-Cys-His-Phe-Gly-Pro-Leu-Thr-Trp-Val-Cys-Lys-Pro-Gln-Gly-Gly-OH (SEQ ID NO: 94) (~3.5×10$^{-5}$ M) in 50 mM phosphate buffer solutions of pH 7.4 containing leucine aminopeptidase (25 U/ml) was studied as described above. A half-life of more than 24 hours was estimated for the degradation.

H-(Lys)$_6$-Gly-Gly-Thr-Tyr-Ser-Cys-His-Phe-Gly-Pro-Leu-Thr-Trp-Val-Cys- Lys-Pro-Gln-Gly-Gly-(Lys)$_6$-OH ((Lys)$_6$-EMP-1-OH) (SEQ ID NO: 95)

Hydrolysis Kinetics in Leucine Aminopeptidase

The degradation of H-(Lys)$_6$-Gly-Gly-Thr-Tyr-Ser-Cys-His-Phe-Gly-Pro-Leu-Thr-Trp-Val-Cys-Lys-Pro-Gln-Gly-Gly-(Lys)$_6$-OH (SEQ ID NO: 95) (~2.8×10$^{-5}$ M) in 50 mM phosphate buffer solutions of pH 7.4 containing leucine aminopeptidase (25 U/ml) was studied as described above. A half-life of more than 100 hours was estimated for the degradation.

H-Arg-Pro-Lys-Pro-Gln-Gln-Phe-Phe-Pro-Met-Leu-NH$_2$ (Substance P) (SEQ ID NO: 112)

Hydrolysis Kinetics in Leucine Aminopeptidase

The degradation of H-Arg-Pro-Lys-Pro-Gln-Gln-Phe-Phe-Gly-Leu-Met-NH$_2$ (SEQ ID NO: 112) (~7.4×10$^{-5}$ M) in 50 mM phosphate buffer solutions of pH 7.4 containing leucine aminopeptidase (25 U/ml) was studied as described above. The pseudo first-order rate constant for the degradation was estimated to 4.5×10$^{-2}$ min$^{-1}$ and the corresponding half-life calculated to 16 min as previously described.

Hydrolysis Kinetics in Carboxypeptidase A

The degradation of H-Arg-Pro-Lys-Pro-Gln-Gln-Phe-Phe-Gly-Leu-Met-NH$_2$ (SEQ ID NO: 112) (~7.4×10$^{-5}$ M) in 50 mM phosphate buffer solutions of pH 7.4 containing carboxypeptidase A (1 U/ml) was studied as described above. The pseudo first-order rate constant for the degradation was estimated to 2.0×10$^{-2}$ min$^{-1}$ and the corresponding half-life calculated to 35 min as previously described.

H-Arg-Pro-Lys-Pro-Gln-Gln-Phe-Phe-Gly-Leu-Met-(Lys)$_6$-NH$_2$ (Substance P-(Lys)$_6$-NH$_2$) (SEQ ID NO: 111)

Hydrolysis Kinetics in Leucine Aminopeptidase

The degradation of H-Arg-Pro-Lys-Pro-Gln-Gln-Phe-Phe-Gly-Leu-Met-(Lys)$_6$-NH$_2$ (SEQ ID NO: 111) (~4.7×10$^{-5}$ M) in 50 mM phosphate buffer solutions of pH 7.4 containing leucine aminopeptidase (25 U/ml) was studied as described above. The pseudo first-order rate constant for the degradation was estimated to 1.1×10$^{-2}$ min$^{-1}$ and the corresponding half-life calculated to 66 min as previously described.

Hydrolysis Kinetics in Carboxypeptidase A

The degradation of H-Arg-Pro-Lys-Pro-Gln-Gln-Phe-Phe-Gly-Leu-Met-(Lys)$_6$-NH$_2$ (SEQ ID NO: 111) (~4.7×10$^{-5}$ M) in 50 mM phosphate buffer solutions of pH 7.4 containing carboxypeptidase A (1 U/ml) was studied as described above. The pseudo first-order rate constant for the degradation was estimated to 5.5×10$^{-3}$ min$^{-1}$ and the corresponding half-life calculated to 126 min as previously described.

H-(Lys)$_6$-Arg-Pro-Lys-Pro-Gln-Gln-Phe-Phe-Gly-Leu-Met-NH$_2$ ((Lys)$_6$- Substance P-NH$_2$) (SEQ ID NO: 113)

Hydrolysis Kinetics in Leucine Aminopeptidase

The degradation of H-(Lys)$_6$-Arg-Pro-Lys-Pro-Gln-Gln-Phe-Phe-Gly-Leu-Met-NH$_2$ (SEQ ID NO: 113) (~4.7×10$^{-5}$ M) in 50 mM phosphate buffer solutions of pH 7.4 containing leucine aminopeptidase (25 U/ml) was studied as described above. The pseudo first-order rate constant for the degradation was estimated to 2×10$^{-3}$ min$^{-1}$ and the corresponding half-life calculated to 347 min as previously described.

H-Trp-Ala-Gly-Gly-Asp-Ala-Ser-Gly-Glu-(Lys-Glu)$_3$-OH (DSIP) (SEQ ID NO: 110)

Hydrolysis Kinetics in Leucine Aminopeptidase

The degradation of H-Trp-Ala-Gly-Gly-Asp-Ala-Ser-Gly-Glu-OH (SEQ ID NO: 110) (~10$^{-5}$ M) in 50 mM phosphate buffer solutions of pH 7.4 containing leucine aminopeptidase (25 U/ml) was studied as described above. The half-life was calculated to be less than 20 min.

H-Trp-Ala-Gly-Gly-Asp-Ala-Ser-Gly-Glu-(Lys-Glu)$_3$-OH (DSIP-(Lys-Glu)$_3$- OH) (SEQ ID NO: 8)

Hydrolysis Kinetics in Leucine Aminopeptidase

The degradation of H-Trp-Ala-Gly-Gly-Asp-Ala-Ser-Gly-Glu-(Lys-Glu)$_3$-OH (SEQ ID NO: 8) (~10$^{-5}$ M) in 50 mM phosphate buffer solutions of pH 7.4 containing leucine aminopeptidase (25 U/ml) was studied as described above. The pseudo first-order rate constant for the degradation was determined as described earlier and the half-life calculated to be 145 min.

H-Tyr-Gly-Gly-Phe-Leu-OH (Leu-Enkephalin) (SEQ ID NO: 12)

Hydrolysis Kinetics in Leucine Aminopeptidase

The degradation H-Tyr-Gly-Gly-Phe-Leu-OH (SEQ ID NO: 12) (~1.8×10$^{-4}$ M) in 50 mM phosphate buffer solutions of pH 7.4 containing leucine aminopeptidase (25 U/ml) was studied as described above. The pseudo first-order rate constant for the degradation was estimated to 6.8×10$^{-1}$ min$^{-1}$ and the corresponding half-life calculated to 1.0 min as previously described.

Hydrolysis Kinetics in Carboxypeptidase A

The degradation H-Tyr-Gly-Gly-Phe-Leu-OH (SEQ ID NO: 12) (~1.8×10$^{-4}$ M) in 50 mM phosphate buffer solutions of pH 7.4 containing carboxypeptidase A (1 U/ml) was studied as described above. The pseudo first-order rate constant for the degradation was estimated to 9.8×10$^{-1}$ min$^{-1}$ and the corresponding half-life calculated to 0.7 min as previously described.

H-Tyr-Gly-Gly-Phe-Leu-(Lys)$_6$-OH (Leu-Enkephalin-(Lys)$_6$-OH) (SEQ ID NO: 11)

Hydrolysis Kinetics in Leucine Aminopeptidase

The degradation H-Tyr-Gly-Gly-Phe-Leu-(Lys)$_6$-OH (SEQ ID NO: 11) (~7.5×10$^{-5}$ M) in 50 mM phosphate buffer solutions of pH 7.4 containing leucine aminopeptidase (25 U/ml) was studied as described above. The pseudo first-order rate constant for the degradation was estimated to 9.7×10$^{-3}$ min$^{-1}$ and the corresponding half-life calculated to 72 min as previously described.

Hydrolysis Kinetics in Carboxypeptidase A

The degradation H-Tyr-Gly-Gly-Phe-Leu-(Lys)$_6$-OH (SEQ ID NO: 11) (~7.5×10$^{-5}$ M) in 50 mM phosphate buffer solutions of pH 7.4 containing carboxypeptidase A (1 U/ml) was studied as described above. The pseudo first-order rate constant for the degradation was estimated to 7×10$^{-4}$ min$^{-1}$ and the corresponding half-life calculated to 990 min as previously described.

H-(Lys)$_6$-Tyr-Gly-Gly-Phe-Leu-OH ((Lys)$_6$-(Leu-Enkephalin-OH) (SEQ ID NO: 101)

Hydrolysis Kinetics in Leucine Aminopeptidase

The degradation H-(Lys)$_6$-Tyr-Gly-Gly-Phe-Leu-OH (SEQ ID NO: 101) (~7.5×10$^{-5}$ M) in 50 mM phosphate buffer solutions of pH 7.4 containing leucine aminopeptidase (25 U/ml) was studied as described above. The pseudo first-order rate constant for the degradation was estimated to 2.6×10$^{-2}$ min$^{-1}$ and the corresponding half-life calculated to 27 min as previously described.

H-(Lys)$_6$-Tyr-Gly-Gly-Phe-Leu-(Lys)$_6$-OH ((Lys)$_6$-Leu-Enkephalin-(Lys)$_6$- OH) (SEQ ID NO: 102)

Hydrolysis Kinetics in Leucine Aminopeptidase

The degradation H-(Lys)$_6$-Tyr-Gly-Gly-Phe-Leu-(Lys)$_6$-OH (SEQ ID NO: 102) (~4.8×10$^{-5}$ M) in 50 mM phosphate buffer solutions of pH 7.4 containing leucine aminopeptidase (25 U/ml) was studied as described above. A half-life of more than 100 hours was estimated for the degradation.

H-Tyr-Gly-Gly-Phe-Leu-(Lys)$_{10}$-OH (Leu-Enkephalin-(Lys)$_{10}$-OH) (SEQ ID NO: 109)
Hydrolysis Kinetics in Leucine Aminopeptidase
The degradation H-Tyr-Gly-Gly-Phe-Leu-(Lys)$_{10}$-OH (SEQ ID NO: 109) (~5.4×10$^{-5}$ M) in 50 mM phosphate buffer solutions of pH 7.4 containing leucine aminopeptidase (25 U/ml) was studied as described above. A half-life of more than 100 hours was estimated for the degradation.
Hydrolysis Kinetics in Carboxypeptidase A
The degradation H-Tyr-Gly-Gly-Phe-Leu-(Lys)$_{10}$-OH (SEQ ID NO: 109) (~5.4×10$^{-5}$ M) in 50 mM phosphate buffer solutions of pH 7.4 containing carboxypeptidase A (1 U/ml) was studied as described above. The pseudo first-order rate constant for the degradation was estimated to 3×10$^{-4}$ min$^{-1}$ and the corresponding half-life calculated to 2310 min as previously described.
H-Tyr-Gly-Gly-Phe-Leu-(Orn)$_6$-OH (Leu-Enkephalin-(Orn)$_6$-OH) (SEQ ID NO: 106)
Hydrolysis Kinetics in Leucine Aminopeptidase
The degradation H-Tyr-Gly-Gly-Phe-Leu-(Orn)$_6$-OH (SEQ ID NO: 106) (~5.7×10$^{-5}$ M) in 50 mM phosphate buffer solutions of pH 7.4 containing leucine aminopeptidase (25 U/ml) was studied as described above. The pseudo first-order rate constant for the degradation was estimated to 6.4×10$^{-3}$ min$^{-1}$ and the corresponding half-life calculated to 108 min as previously described.
Hydrolysis Kinetics in Carboxypeptidase A
The degradation H-Tyr-Gly-Gly-Phe-Leu-(Orn)$_6$-OH (SEQ ID NO: 106) (~5.7×10$^{-5}$ M) in 50 mM phosphate buffer solutions of pH 7.4 containing carboxypeptidase A (1 U/ml) was studied as described above. A half-life of more than 100 hours was estimated for the degradation.
H-Tyr-Gly-Gly-Phe-Leu-(Dbu)$_6$-OH (Leu-Enkephalin-(Dbu)$_6$-OH) (SEQ ID NO: 107)
Hydrolysis Kinetics in Leucine Aminopeptidase
The degradation H-Tyr-Gly-Gly-Phe-Leu-(Dbu)$_6$-OH (SEQ ID NO: 107) (~6.0×10$^{-5}$ M) in 50 mM phosphate buffer solutions of pH 7.4 containing leucine aminopeptidase (25 U/ml) was studied as described above. The pseudo first-order rate constant for the degradation was estimated to 2.5×10$^{-2}$ min$^{-1}$ and the corresponding half-life calculated to 28 min as previously described.
Hydrolysis Kinetics in Carboxypeptidase A
The degradation H-Tyr-Gly-Gly-Phe-Leu-(Dbu)$_6$-OH (SEQ ID NO: 107) (~6.0×10$^{-5}$ M) in 50 mM phosphate buffer solutions of pH 7.4 containing carboxypeptidase A (1 U/ml) was studied as described above. The pseudo first-order rate constant for the degradation was estimated to 5×10$^{-3}$ min$^{-1}$ and the corresponding half-life calculated to 1386 min as previously described.
H-Tyr-Gly-Gly-Phe-Leu-(Dpr)$_6$-OH (Leu-Enkephalin-(Dpr)$_6$-OH) (SEQ ID NO: 108)
Hydrolysis Kinetics in Leucine Aminopeptidase
The degradation H-Tyr-Gly-Gly-Phe-Leu-(Dpr)$_6$-OH (SEQ ID NO: 108) (~6.3×10$^{-5}$ M) in 50 mM phosphate buffer solutions of pH 7.4 containing leucine aminopeptidase (25 U/ml) was studied as described above. The pseudo first-order rate constant for the degradation was estimated to 1.7×10$^{-1}$ min$^{-1}$ and the corresponding half-life calculated to 4.2 min as previously described.
Hydrolysis Kinetics in Carboxypeptidase A
The degradation H-Tyr-Gly-Gly-Phe-Leu-(Dpr)$_6$-OH (SEQ ID NO: 108) (~6.3×10$^{-5}$ M) in 50 mM phosphate buffer solutions of pH 7.4 containing carboxypeptidase A (1 U/ml) was studied as described above. The pseudo first-order rate constant for the degradation was estimated to 2.4×10$^{-2}$ min$^{-1}$ and the corresponding half-life calculated to 29 min as previously described.
H-Tyr-Gly-Gly-Phe-Leu-Lys(Glu)$_4$-Lys-OH (Leu-Enkephalin-Lys-(Glu)$_4$- Lys-OH) (SEQ ID NO: 98)
Hydrolysis Kinetics in Leucine Aminopeptidase
The degradation H-Tyr-Gly-Gly-Phe-Leu-Lys-(Glu)$_4$-Lys-OH (SEQ ID NO: 98) (~7.5×10$^{-5}$ M) in 50 mM phosphate buffer solutions of pH 7.4 containing leucine aminopeptidase (25 U/ml) was studied as described above. The pseudo first-order rate constant for the degradation was estimated to 6.5×10$^{-2}$ min$^{-1}$ and the corresponding half-life calculated to 11 min as previously described.
Hydrolysis Kinetics in Carboxypeptidase A
The degradation H-Tyr-Gly-Gly-Phe-Leu-Lys-(Glu)$_4$-Lys-OH (SEQ ID NO: 98) (~7.5×10$^{-5}$ M) in 50 mM phosphate buffer solutions of pH 7.4 containing carboxypeptidase A (1 U/ml) was studied as described above. The pseudo first-order rate constant for the degradation was estimated to 6×10$^{-4}$ min$^{-1}$ and the corresponding half-life calculated to 1155 min as previously described.
H-Tyr-Gly-Gly-Phe-Leu-Lys-(Glu)$_3$-OH (Leu-Enkephalin-Lys-(Glu)$_3$- (Lys)$_2$-OH) (SEQ ID NO: 120)
Hydrolysis Kinetics in Leucine Aminopeptidase
The degradation H-Tyr-Gly-Gly-Phe-Leu-Lys-(Glu)$_3$-(Lys)$_2$-OH (SEQ ID NO: 120) (~7.5×10$^{-5}$ M) in 50 mM phosphate buffer solutions of pH 7.4 containing leucine aminopeptidase (25 U/ml) was studied as described above. The pseudo first-order rate constant for the degradation was estimated to 1.2×10$^{-1}$ min$^{-1}$ and the corresponding half-life calculated to 5.7 min as previously described.
Hydrolysis Kinetics in Carboxypeptidase A
The degradation H-Tyr-Gly-Gly-Phe-Leu-Lys-(Glu)$_3$-(Lys)$_2$-OH (SEQ ID NO: 120) (~7.5×10$^{-5}$ M) in 50 mM phosphate buffer solutions of pH 7.4 containing carboxypeptidase A (1 U/ml) was studied as described above. The pseudo first-order rate constant for the degradation was estimated to 8×10$^{-4}$ min$^{-1}$ and the corresponding half-life calculated to 866 min as previously described.
Studies with Enkephalin Analogues
Bioavailability of Leu-enkephalin-OH (SEQ ID NO: 12) and Leu-enkephalin-(Lys)$_6$-OH (SEQ ID NO: 11) in Mice
Male mice weighing 20-25 g were given 50 mg Leu-enkephalin-(Lys)$_6$-OH (SEQ ID NO: 11) per kg body weight i.v. or p.o. The compound was dissolved in isotonic NaCl solution. Mice treated with Leu-enkephalin-(Lys)$_6$-OH (SEQ ID NO: 11), 50 mg/kg p.o. were bled by decapitation at 0, 15, 30, 60, 90, 240, 480, 960 and 1380 minutes after dosing. Mice treated with Leu-enkephalin-(Lys)$_6$-OH (SEQ ID NO: 11), 50 mg/kg i.v. were bled by decapitation at 5, 15, 30, 60, 180, 240, 370, 720, 1080, and 1440 minutes after dosing. Animals treated with the native Leu-enkephalin-OH (SEQ ID NO: 12), 50 mg/kg p.o. or i.v. were bled by decapitation 30 min after dosing. Blood samples were centrifuged immediately (3000 g, 4° C.) and serum was isolated and used for activity determination.

The concentrations of Leu-enkephalin-OH (SEQ ID NO: 12) or Leu-enkephalin-(Lys)$_6$-OH (SEQ ID NO: 11) in serum were determined by a bioassay using the vas deferens model from mice. Experiments were carried out essentially as described by Takemori and Porthogese, 1984, *Eur. J. Pharmacol.* 104:101-104. In short: vasa deferentia were isolated from male mice weighing 20-30 g (Møllegaard breeding, DK) and suspended through two electrodes in 10 ml baths at resting tension of 1 g. The tissues were bathed with Krebs-bicarbonate solution (physiological buffer solution) maintained at 36-37° C. and continuously bubbled with 95% O$_2$ and 5% $CO_2$. The tissues were stimulated electrically (70 V, 1 ms duration; 0.1 Hz) and contractions were recorded isometrically on a chart recorder. After equilibration of the tissue for at least 20 min, drugs were added in the bath and the maximum effects were measured. Data were fitted to the equation % Inhibition=MAX×$(1-[Inh]^n/([Inh]^n+IC_{50}^n))$+baseline, where MAX is the maximum muscle contraction, [Inh] is the concentration of the inhibitor, n is the Hill slope of the curve and baseline is the muscle contraction insensitive to the compound. Thus, the calculated concentration is a reflection of inhibitory activity in the vas deferens bioassay preparation and not an exact measure of Leu-enkephalin-OH (SEQ ID NO: 12) or Leu-enkephalin-(Lys)$_6$-OH (SEQ ID NO: 11) in serum.

Values for Leu-enkephalin-OH (SEQ ID NO: 12) and Leu-enkephalin-(Lys)$_6$-OH (SEQ ID NO: 11) are mean values±S.E.M of at least 5 experiments. In assays where the concentration of Leu-enkephalin-(Lys)$_6$-OH (SEQ ID NO: 11) in serum was determined, 100 µl of serum was added to the tissue bath and the % inhibition of the response was determined. The results are shown in Table 2.

Stability of Leu-enkephalin-OH (SEQ ID NO: 12) and Leu-Enkephalin-(Lys)$_6$-OH (SEQ ID NO: 11) in Mouse Plasma at 37° C.

The stability of Leu-enkephalin-OH (SEQ ID NO: 12), Leu-Enkephalin-(Lys)$_6$-OH (SEQ ID NO: 11), Leu-Enkephalin-(Glu$_2$-Lys-Glu$_3$)—OH (SEQ ID NO: 121), Leu-Enkephalin-(Lys-Glu$_4$-Lys)-OH (SEQ ID NO: 98), Leu-Enkephalin-(ORN)$_6$—OH (SEQ ID NO: 106), Leu-Enkephalin-(DBU)$_6$—OH (SEQ ID NO: 107), Leu-Enkephalin-(DPR)$_6$—OH (SEQ ID NO: 108), and Leu-Enkephalin-(Lys)$_{10}$-OH (SEQ ID NO: 109) in mouse plasma at 37° C. was examined in the vas deferens bioassay model as described above. Prior to addition of the plasma sample, a standard dose-response curve was generated in each preparation in order to express the inhibitory activity as concentration of each test substance. Thus, the calculated concentration is a reflection of inhibitory activity in the vas deferens bioassay preparation. Dose-response data were fitted to the equation:

Response=Initial value·$(1-(conc/EC_{50}+conc))$+background,

TABLE 2

Functional activity in serum after p.o. or i.v. administration of Leu-enkephalin-(Lys)$_6$-OH in mice (n = 6-8 serum samples per time point; mean ± S.E.M.).

| p.o. administration | | i.v. administration | |
| --- | --- | --- | --- |
| Time (min) | Activity Leu-enkephalin-(Lys)$_6$-OH (nM) (SEQ ID NO: 11) | Time (min) | Activity Leu-enkephalin-(Lys)$_6$-OH (nM) (SEQ ID NO: 11) |
| 0 | 0 | 5 | 15900 ± 2400 |
| 15 | <Detection Limit | 15 | 8500 ± 1200 |
| 30 | 3000 ± 800 | 30 | 6000 ± 950 |
| 60 | 6000 ± 1300 | 60 | 1600 ± 340 |
| 90 | 10900 ± 3800 | 180 | 440 ± 110 |
| 240 | 10700 ± 230 | 240 | 2500 ± 320 |
| 480 | 5000 ± 580 | 370 | 31200 ± 8620 |
| 960 | 2800 ± 780 | 720 | <Detection Limit |
| 1380 | <Detection Limit | 1080 | <Detection Limit |
| N/A | N/A | 1440 | <Detection Limit |

N/A: Non-Applicable

Following an i.v. injection of 50 mg per kg body weight of Leu-enkephalin-(Lys)$_6$-OH (SEQ ID NO: 11), a rapid increase in activity was observed in serum already after 5 min. Then, activity declined within the following 30 min, but between 240 min (4 hrs) and 720 min (12 hrs), the activity reached a second peak level. The second peak was possibly related to enterohepatic circulation of the drug after i.v. administration. Activity in plasma was below the detection limit at 12, 18 and 24 hours after i.v. administration of Leu-enkephalin-(Lys)$_6$-OH (SEQ ID NO: 11). After p.o. administration of Leu-enkephalin-(Lys)$_6$-OH (SEQ ID NO: 11), the activity in serum reached a maximum at 90-240 min (1.5-4 hrs) and activity was detectable after 8, and 16 hrs, but not after 23 hrs. While high activities were observed at 30 min in serum samples from animals treated with Leu-enkephalin-(Lys)$_6$-OH (SEQ ID NO: 11) either p.o. or i.v., no activity was detected 30 min after p.o. or i.v. administration of the native Leu-enkephalin-OH (SEQ ID NO: 12).

These results suggest that Leu-enkephalin-(Lys)$_6$-OH (SEQ ID NO: 11), but not Leu-enkephalin-OH (SEQ ID NO: 12), is absorbed after p.o. administration and that the elimination rate in serum is substantially reduced relative to the native Leu-enkephalin (SEQ ID NO: 12) in mice.

where initial=initial helically-induced contraction force prior to addition of test substance;

conc=concentration of test substance;

$EC_{50}$=concentration of test substance that produced half maximal inhibition of electrically-induced contraction; and background=contraction force during maximal relaxation.

All enkephalin analogues were dissolved in Krebs buffer in a concentration of 1 mM. Sixty-six µl of each test substance solution (66 nmol enkephalin analog) was incubated with 600 µl plasma at 37° C. At different time points (2-120 min), 10 µl samples were withdrawn for analysis of functional activity. Functional activity of each test substance in plasma was expressed as the concentration of the test substance that elicited the same inhibition of electrically-induced contraction in the vas deferens bioassay. $T_{1/2}$ was calculated by fitting the time-concentration data to the equation:

$$conc(t)=conc(0)\cdot e^{(-ln2/T1/2)\cdot t}$$

where conc(0)=concentration at t=0. The results are shown in Table 3.

TABLE 3

$EC_{50}$ and $T_{1/2}$ values for various enkephalin analogues (n = 3-4/test substance; mean)

| Compound | $EC_{50}$ value (nM) | $T_{1/2}$ (min) |
|---|---|---|
| Leu-Enkephalin-OH (SEQ ID NO: 12) | 65 | 6.3 |
| Leu-Enkephalin-(Lys)$_6$-OH (SEQ ID NO: 11) | 160 | 18.7 |
| Leu-Enkephalin-(Glu)$_6$-OH (SEQ ID NO: 10) | 140 | ND |
| Leu-Enkephalin-(Lys-Glu)$_3$-OH (SEQ ID NO: 99) | 350 | ND |
| Leu-Enkephalin-(Lys$_2$-Glu$_3$-Lys)-OH (SEQ ID NO: 97) | 680 | ND |
| Leu-Enkephalin-(Lys-Glu$_4$-Lys)-OH (SEQ ID NO: 98) | 357 | 84.5 |
| Leu-Enkephalin-(Orn)$_6$-OH (SEQ ID NO: 106) | >20000 | ND |
| Leu-Enkephalin-(Dbu)$_6$-OH (SEQ ID NO: 107) | 20000 | ND |
| Leu-Enkephalin-(Dpr)$_6$-OH (SEQ ID NO: 100) | 200 | 19.8 |
| Leu-Enkephalin-(Lys)$_{10}$-OH (SEQ ID NO: 109) | 2500 | ND |

ND: Not determined.

These data suggest that modifications of Leu-Enkephalin-OH (SEQ ID NO: 12) increased the $EC_{50}$ value and increased the stability in mouse plasma at 37° C.

μ-Receptor Binding of Leu-enkephalin-OH Analogues (SEQ ID NO: 12)

Affinities for μ opioid receptor were determined using [$^3$H] (D-Ala$^2$,N-Me-Phe$^4$, Gly-ol$^5$) Enkephalin (DAMGO) (1 nM) as described by Christensen, 1993, Pharmacol. Toxicol. 73:344-345. In short: Bovine brains were placed on ice within minutes after the slaughter. The caudate nuclei were dissected and homogenized in 20 vol. of 0.32 M sucrose. The homogenate was centrifuged at 2000 g for 10 min. The pellet was re-suspended in 10 vol. of 50 mM Tris-HCl buffer 7.4 and stored at −20° C. until use. The synaptic membrane fraction was incubated with 1 nM of [3H]DAMGO in the presence of various concentrations of test ligand. Non-specifically bound [3H]-DAMGO was established using 1 μM naloxone. Following 15 min. incubation at 36° C. samples were filtered through Whatman GF/C filters and washed with buffer. Radioactivity was determined using conventional techniques.

As shown in Table 4 below, all compounds were active in this binding assay, indicating that modification of Leu-enkephalin-OH (SEQ ID NO: 12) affects receptor affinity.

TABLE 4

Affinity of Leu-Enkephalin-OH (SEQ ID NO: 12) analogues at μ opioid receptors measured as $^3$H-DAMGO binding ($IC_{50}$ values (mean ± SD))

| Compound | $IC_{50}$ values (nM) Time 0 hours | $IC_{50}$ values (nM) Time 18 hours |
|---|---|---|
| Leu-Enkephalin-OH (SEQ ID NO: 12) | 97 ± 9 | 80 |
| Leu-Enkephalin-(Lys)$_6$-OH (SEQ ID NO: 11) | 17 ± 7 | 32 |
| Leu-Enkephalin-(Glu)$_6$-OH (SEQ ID NO: 10) | 10,000 | 5,000 |
| Leu-Enkephalin-(Lys-Glu)$_3$-OH (SEQ ID NO: 99) | 450 ± 130 | 900 |
| Naloxone | 9.2 ± 1.0 | 7 |

The low affinity of Leu-Enkephalin-(Glu)$_6$-OH (SEQ ID NO: 10) relative to the other test substances may be due to the very low solubility of this compound. Thus, the $IC_{50}$ value of Leu-Enkephalin-(Glu)$_6$-OH (SEQ ID NO: 10) may be lower if tested in a solvent in which the compound is more soluble.

In Vivo Experiments with EMP-1-K$_6$ (SEQ ID NO. 93) in Mice

To examine the biological efficacy of peroral (p.o.) treatment with EMP-1 (SEQ ID NO: 117) and EMP-1-K$_6$ (SEQ ID NO: 93), the hematological responses of an equimolar p.o. dose (956 nmol) of EMP-1 (SEQ ID NO: 117) (2 mg) and EMP-1-K$_6$ (SEQ ID NO: 93) (2.56 mg) were examined in male mice (n=8/group). To examine the time course of the hematological responses, a 10 μl venous blood sample was collected from the retroorbital plexus on days 0, 2, and 4. Body weight (BW) and the plasma concentration of hemoglobin (P-Hgb), the hematocrit value (Hct), the red blood cell count (RBC), and the mean cell hemoglobin concentration (MCHC) were determined before (Day 0), and 2 and 4 days after administration of EMP-1 or EMP-1-K$_6$. The results are shown in Table 5.

TABLE 5

Changes in body weight and in hematological parameters 4 days after p.o. administration of 956 nmol EMP-1 or EMP-1-K$_6$. Relative changes are presented in parenthesis (mean ± SEM).

|  | EMP-1 (SEQ ID NO: 117) p.o. | EMP-1-K$_6$ (SEQ ID NO: 93) p.o. |
|---|---|---|
| BW (g) | 3.4 ± 0.2 | 3.4 ± 0.3 |
|  | (16 ± 1%) | (15 ± 2%) |
| P-hgb (mM) | +1.5 ± 0.5 | +2.4 ± 0.3* |
|  | (+8 ± 1%) | (+15 ± 2%*) |
| Hematocrit (%) | 0.3 ± 0.8 | 4.5 ± 0.9* |
|  | (0.8 ± 1.8%) | (12.3 ± 2.3%*) |
| RBC ($10^{12}$ cells/l) | 0.6 ± 0.2 | 1.0 ± 0.1* |
|  | (9 ± 3%) | (17 ± 2%*) |
| MCHC (mM) | 2.9 ± 1.5 | 0.2 ± 1.5 |
|  | (4 ± 2%) | (0 ± 2%) |

*p < 0.05 vs. EMP-1 (SEQ ID NO: 117) p.o.

These data show that the p.o. administration of 2.56 mg EMP-1-K$_6$ (SEQ ID NO: 93) produces a significantly greater increase in P-hgb, Hct, and RBC than the equimolar dose of EMP-1 (SEQ ID NO: 117) p.o. None of the compounds affected growth or MCHC. These results suggest that EMP-1-K$_6$ (SEQ ID NO: 93) is absorbed after p.o. administration and that it elicits a rapid stimulation of the erythropoiesis in mice.

Studies with Parathyroid Hormone (PTH) Analogues

General Procedures

Osteoblast retraction assay: Retraction assays were performed with osteoblast prepared from calvaria of 1-day old mice according to published protocols (Miller et al., 1976, Science 192:1340-1343). In brief, osteoblasts were seeded in serum-free minimal essential medium-α (αMEM) at a density of 3000 cells per cm$^2$ into 96-well tissue culture plates coated with 50 μg/ml of type I collagen in phosphate-buffered saline containing 0.1% bovine serum albumin (PBS). One day after plating, PTH compounds were added to a final concentration of 10 nM and incubation was carried out for 1 h. Cells were then fixed and stained with toluidine blue, and the number of retracted cells was counted by visual inspection. PTH itself is able retract some 64% of the cells compared to blanks where only 10-12% of the cells are retracted.

Enzyme immunoassay (EIA) for human PTH (1-34) (SEQ ID NO: 119): This is a standard EIA assay (EIAS(h)-6101 from Peninsula Laboratories, Inc.) Biotinylated peptide and peptide competes for binding to PTH (1-34)-antibody. Streptavidin-conjugated Horseradish Peroxidase (SA-HRP) is allowed to bind to the primary antibody/biotinylated peptide complex. 3,3',5,5'-Tetramethyl Benzidine Dihydrochloride (TMB) is allowed to react with the bound HRP. The colour intensity is used to quantification.

Specificity of the assay: hPTH(1-34)=100%; hPTH(1-38)=100%; hPTH(1-44)=0%; hPTH(39-68)=0%; hPTH(1-84)=0%; ratPTH(1-34)=0%.

The results are shown in Table 6. In the osteoblast retraction assay, hPTH(1-34) (SEQ ID NO: 119) retains approximately 89% of the activity of native, human parathyroid hormone. H-hPTH(1-34)-$K_6$—OH (SEQ ID NO: 91) and H-$K_6$—PTH(1-34)-OH (SEQ ID NO: 90) show 55 and 49%, respectively of the activity of the mother compound hPTH(1-34) (SEQ ID NO: 119). The antibody towards hPTH(1-34) (SEQ ID NO: 119) used in EIA recognises the two modifications well.

TABLE 6

| Compound/Assay | Retraction assay % Retracted cells | EIA Relative recovery % |
|---|---|---|
| Parathyroid Hormone | 63.7 | — |
| hPTH (1-34) (SEQ ID NO: 119) | 58.2 | 90.8 |
| H-hPTH(1-34)-$K_6$—OH (SEQ ID NO: 91) | 37.4 | 61.8 |
| H—$K_6$-PTH(1-34)-OH (SEQ ID NO: 90) | 34.7 | 79.1 |
| Blank | 11.8 | — |

Functional Activity of Substance P—$NH_2$ (SEQ ID NO: 112) and $(Lys)_6$-Substance P—$NH_2$ (SEQ ID NO: 113)

The functional activity of Substance P—$NH_2$ (SEQ ID NO: 112) and $(Lys)_6$-Substance P—$NH_2$ (SEQ ID NO: 113) were characterized using the guinea pig illeum. Experiments were carried out essentially as described by Kristiansen et al., 1992, Br. J. Pharmacol. 58:1150) with the modification that the illeum was not electrically stimulated. Following application of the compounds the induced contraction was measured. Dose-response data were fitted to the equation:

$$Response = Initial\ value \cdot conc/(EC_{50} + conc)$$

where initial value=initial electrically-induced contraction force prior to addition of test substance;

conc=concentration of test substance; and $EC_{50}$=concentration of test substance that produced half maximal inhibition of electrically-induced contraction.

Substance P—$NH_2$ (SEQ ID NO: 112) ($EC_{50}$=40 nM) and $(Lys)_6$-Substance P—$NH_2$ (SEQ ID NO: 113) ($EC_{50}$=5 nM) both acted as agonists at the guinea pig illeum.

Other Embodiments

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

The invention claimed is:

1. A pharmacologically active peptide conjugate having a reduced tendency towards enzymatic cleavage comprising X and Z,
   wherein X is a pharmacologically active peptide sequence selected from the group consisting of adrenocorticotropic hormone (ACTH), melanotan II, melanocyte stimulating hormone (MSH), and alpha-MSH, and
   wherein Z is a peptide sequence of 4-15 amino acid units covalently bound to X via a peptide bond to the C-terminal carbonyl function of X and/or to the N-terminal nitrogen atom of X, and wherein Z consists of residues selected from Glu, Lys, and Met, and
   wherein the ratio between the half-life of said peptide conjugate and the half-life of the corresponding pharmacologically active peptide sequence X, when treated with carboxypeptidase A or leucine aminopeptidase in about 50 mM phosphate buffer solution at about pH 7.4 at about 37° C. or in serum or plasma is at least about 2, or wherein said peptide conjugate has a half-life in human or mice serum or plasma at 37° C. of at least about 10 minutes.

2. A peptide conjugate according to claim 1, wherein Z is covalently bound to X via a peptide bond to the N-terminal nitrogen atom of X.

3. A peptide conjugate according to claim 1, wherein X is alpha-MSH.

4. A peptide conjugate according to claim 1, wherein Z consists of 4-10 amino acid units.

5. A peptide conjugate according to claim 1, wherein Z consists of 4-7 amino acid units.

6. A peptide conjugate according to claim 1, wherein Z consists of 6 amino acid units.

7. A peptide conjugate according to claim 6, wherein Z is $Lys_6$.

8. A peptide conjugate according to claim 1, wherein the amino acid units in Z are Lys.

9. A peptide conjugate according to claim 8, wherein Z is selected from the group consisting of $Lys_4$, $Lys_5$, and $Lys_6$.

10. A method for producing a peptide conjugate according to claim 1, comprising
   a) introducing a nucleic acid sequence encoding said conjugate into a host cell;
   b) culturing said host cell and
   c) isolating said conjugate from the culture.

11. A method for producing a peptide conjugate according to claim 1, comprising
   a) culturing a recombinant host cell comprising a nucleic acid sequence encoding said conjugate under conditions permitting the production of said conjugate; and
   b) isolating said conjugate from the culture.

12. A composition comprising a pharmacologically active peptide conjugate as defined in claim 1 and a pharmaceutical acceptable carrier.

13. The peptide conjugate of claim 1, wherein said pharmacologically active peptide sequence is melanotan II.

14. The peptide conjugate of claim 1, wherein X comprises at least 10 amino acid residues.

15. The composition of claim 12, wherein said composition is formulated for oral, subcutaneous, parenteral, intramuscular, rectal, epidural, intratracheal, intranasal, vaginal, buccal, ocular, direct brain, pulmonary or topical administration.

16. The composition of claim 12, wherein X comprises at least 10 amino acid residues.

17. The composition of claim 12, said composition being in a form selected from the group consisting of a capsule, a tablet, an aerosol, a solution, a suspension or a topical application.

18. The composition of claim 12, wherein Z is covalently bound to the N-terminal nitrogen atom of X.

19. The composition of claim 12, wherein X is alpha-MSH.

20. The composition of claim 12, wherein Z consists of 4-10 amino acid units.

21. The composition of claim 12, wherein Z consists of 4-7 amino acid units.

22. The composition of claim 12, wherein Z consists of 6 amino acid units.

23. The composition of claim 12, wherein the amino acid units in Z are lysine residues.

24. The composition of claim 12, wherein Z is selected from the group consisting of $Lys_4$, $Lys_5$, and $Lys_6$.

25. The composition of claim 24, wherein Z is $Lys_6$.

26. A method for the preparation of a pharmacologically active peptide conjugate (Z—X) as defined in claim 2, comprising the steps of:
   a) coupling an N-α-protected amino acid, or an N-α-protected dipeptide to a solid support material (SSM), thereby forming an immobilised N-a-protected amino acid;
   b) removing the N-α-protecting group, thereby forming an immobilised amino acid or peptide fragment having an unprotected N-terminal end;
   c) coupling an additional N-α-protected amino acid in the carboxyl activated form, or an additional N-α-protected dipeptide in the C-terminal activated form to the N-terminal end of the immobilised amino acid or peptide fragment, and repeating the removal/coupling step procedure in step b) and c) until the desired peptide sequence X is obtained, wherein X is a pharmacologically active peptide sequence selected from the group consisting of adrenocorticotropic hormone (ACTH), melanotan II, melanocyte stimulating hormone (MSH), and alpha-MSH;
   d) coupling an additional N-α-protected amino acid in the carboxyl activated form, or an additional N-α-protected dipeptide in the C-terminal activated form to the N-terminal end of the immobilised peptide fragment, and repeating the removal/coupling step procedure in step b) and d) until the desired peptide sequence Z is obtained, wherein Z is a peptide sequence of 4-15 amino acid units and consists of residues selected from Glu, Lys, and Met; and then
   e) cleaving off the peptide conjugate from the solid support material.

* * * * *

UNITED STATES PATENT AND TRADEMARK OFFICE
CERTIFICATE OF CORRECTION

| | |
|---|---|
| PATENT NO. | : 7,935,786 B2 |
| APPLICATION NO. | : 11/807159 |
| DATED | : May 3, 2011 |
| INVENTOR(S) | : Bjarne D. Larsen |

It is certified that error appears in the above-identified patent and that said Letters Patent is hereby corrected as shown below:

On the Title Page, item (56) under OTHER PUBLICATIONS, in Amendment filed Sept. 18, 2009, replace "(filed Jul. 13, 1999)." with --(filed Jul. 12, 1999).--.

Page 2, under OTHER PUBLICATIONS, in Abstract of Larsen et al., replace "*Peptides*Proceedings" with --*Peptides* Proceedings--;

Under OTHER PUBLICATIONS, in Cone et al., replace "*Recent Prog. Norm. Res.*" with --*Recent Prog. Horm. Res.*--;

Under OTHER PUBLICATIONS, in Datta et al., replace "*Neurosci. Biobehay. Rev.*" with --*Neurosci. Biobehav. Rev*--.

Page 3, under OTHER PUBLICATIONS, in Labbéet al., replace "Labbéeet al.," with --Labbé et al.,--;

Under OTHER PUBLICATIONS, in Schiöth et al., "Expression of Functional Melanocortin", replace "*Biotchem. Biophys. Res. Commun.*" with --*Biochem. Biophys. Res. Commun.*--.

In The Specification

Column 8, Line 10, replace "Xaa- Xaa-Lys-Lys-Lys (SEQ ID NO: 70)" with --Xaa-Lys-Xaa-Lys-Lys-Lys (SEQ ID NO: 70)--.

Column 10, Line 43, replace "N- an/or C-terminal" with --N- and/or C-terminal--.

Column 13, Line 17, replace "to some extend" with --to some extent--;

Line 18, replace "one the other hand" with --on the other hand--;

Signed and Sealed this
Seventeenth Day of February, 2015

Michelle K. Lee
*Deputy Director of the United States Patent and Trademark Office*

CERTIFICATE OF CORRECTION (continued)
U.S. Pat. No. 7,935,786 B2

Line 19, replace "to some extend," with --to some extent,--.

Column 24, Line 45, replace "etinction coefficient" with --extinction coefficient--.

Column 26, Line 34, replace "5-☐m" with --5-μm--.

Column 36, Line 62, replace "Cys-His-Phe-Gly-Pro-Leu-hr-Trp-Val-Cys-Lys-Pro-" with
--Cys-His-Phe-Gly-Pro-Leu-Thr-Trp-Val-Cys-Lys-Pro- --.

Column 44, Lines 37-38, replace "(EMP-1-OH)" with --(EMP-1-(Lys)$_6$-OH)--.

Column 45, Line 9, replace "H-Arg-Pro-Lys-Pro-Gln-Gln-Phe-Phe-Pro-Me-Leu-NH$_2$" with
--H-Arg-Pro-Lys-Pro-Gln-Gln-Phe-Phe-Met-Me-Leu-NH$_2$--;

Line 60, replace "H-Trp-Ala-Gly-Gly-Asp-Ala-Ser-Gly-Glu-(Lys-Glu)$_3$-OH" with
--H-Trp-Ala-Gly-Gly-Asp-Ala-Ser-Gly-Glu-OH--.

Column 48, Line 22, replace "H-Tyr-Gly-Gly-Phe-Leu-Lys-(Glu)$_3$-OH" with
--H-Tyr-Gly-Gly-Phe-Leu-Lys-(Glu)$_3$-(Lys)$_2$-OH--.